United States Patent
Yun et al.

(10) Patent No.: US 11,495,745 B2
(45) Date of Patent: Nov. 8, 2022

(54) COMPOUND AND ORGANIC LIGHT EMITTING DEVICE COMPRISING SAME

(71) Applicant: LG CHEM, LTD., Seoul (KR)

(72) Inventors: Jun Yun, Daejeon (KR); Joo Yong Yoon, Daejeon (KR); Yeon Hwan Kim, Daejeon (KR); Wanpyo Hong, Daejeon (KR)

(73) Assignee: LG CHEM, LTD., Seoul (KR)

( * ) Notice: Subject to any disclaimer, the term of this patent is extended or adjusted under 35 U.S.C. 154(b) by 487 days.

(21) Appl. No.: 16/650,156

(22) PCT Filed: Oct. 17, 2018

(86) PCT No.: PCT/KR2018/012273
§ 371 (c)(1),
(2) Date: Mar. 24, 2020

(87) PCT Pub. No.: WO2019/078620
PCT Pub. Date: Apr. 25, 2019

(65) Prior Publication Data
US 2020/0235304 A1    Jul. 23, 2020

(30) Foreign Application Priority Data

Oct. 20, 2017 (KR) .................. 10-2017-0136519
Oct. 16, 2018 (KR) .................. 10-2018-0123424

(51) Int. Cl.
*H01L 29/08* (2006.01)
*H01L 51/00* (2006.01)
(Continued)

(52) U.S. Cl.
CPC ........ *H01L 51/0054* (2013.01); *C07C 255/35* (2013.01); *C09K 11/06* (2013.01);
(Continued)

(58) Field of Classification Search
CPC ............................ H01L 51/0054; H01L 29/08
See application file for complete search history.

(56) References Cited

U.S. PATENT DOCUMENTS

2001/0046611 A1  11/2001 Kido et al.
2004/0251816 A1  12/2004 Leo et al.
(Continued)

FOREIGN PATENT DOCUMENTS

EP    1950817 A1    7/2008
JP    H04-338761    11/1992
(Continued)

OTHER PUBLICATIONS

International Search Report and the Written Opinion of PCT/KR2018/012273, dated Feb. 1, 2019.

*Primary Examiner* — Caleb E Henry
(74) *Attorney, Agent, or Firm* — Dentons US LLP

(57) ABSTRACT

Provided is a compound of Chemical Formula 1:

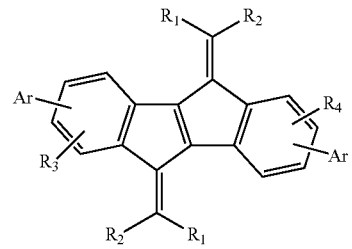

Chemical Formula 1 where $R_1$ and $R_2$ are each independently hydrogen, a substituted or unsubstituted $C_{1-60}$ alkyl, a substituted or unsubstituted $C_{1-60}$ alkoxy, a substituted or unsubstituted $C_{1-60}$
(Continued)

haloalkyl, a substituted or unsubstituted $C_{1-60}$ haloalkoxy, halogen, cyano, tri($C_{1-60}$ alkyl)silyl, a substituted or unsubstituted $C_{6-60}$ aryl, or a substituted or unsubstituted $C_{2-60}$ heteroaryl containing at least one of O, N, Si and S, $R_3$ and $R_4$ are each independently hydrogen, deuterium, a substituted or unsubstituted $C_{1-60}$ alkyl, a substituted or unsubstituted $C_{1-60}$ alkoxy, a substituted or unsubstituted $C_{1-60}$ haloalkyl, a substituted or unsubstituted $C_{1-60}$ haloalkoxy, halogen, cyano, tri($C_{1-60}$ alkyl)silyl, or a substituted or unsubstituted $C_{2-60}$ heteroaryl containing at least one of O, N, Si and S, and Ar is $C_{6-60}$ aryl, or $C_{2-60}$ heteroaryl containing at least one of O, N, Si and S, wherein the $C_{6-60}$ aryl, or $C_{2-60}$ heteroaryl is substituted with 1 to 5 substituents each selected from the group consisting of a substituted or unsubstituted $C_{1-60}$ alkyl, a substituted or unsubstituted $C_{1-60}$ alkoxy, a substituted or unsubstituted $C_{1-60}$ haloalkyl, a substituted or unsubstituted $C_{1-60}$ haloalkoxy, halogen, cyano, and tri($C_{1-60}$ alkyl)silyl, and an organic light emitting device including the same.

14 Claims, 2 Drawing Sheets

(51) Int. Cl.
*C07C 255/35* (2006.01)
*C09K 11/06* (2006.01)
*H01L 51/50* (2006.01)

(52) U.S. Cl.
CPC ........ *C07C 2603/40* (2017.05); *H01L 51/506* (2013.01); *H01L 51/5036* (2013.01); *H01L 51/5088* (2013.01)

(56) References Cited

U.S. PATENT DOCUMENTS

| | | |
|---|---|---|
| 2007/0108894 A1 | 5/2007 | Hosokawa et al. |
| 2009/0105488 A1* | 4/2009 | Cheng ............... C07F 7/081 548/440 |
| 2009/0230854 A1 | 9/2009 | Kim et al. |
| 2012/0193619 A1 | 8/2012 | Taka et al. |
| 2014/0077175 A1 | 3/2014 | Jung et al. |
| 2015/0236267 A1* | 8/2015 | Hiroaki ............ H01L 51/0061 257/40 |
| 2016/0181542 A1* | 6/2016 | Kawamura ........ C07D 209/86 585/27 |
| 2018/0309057 A1* | 10/2018 | Ikeda ............... H01L 51/0085 |
| 2018/0309081 A1* | 10/2018 | Ikeda ............... H01L 51/0073 |
| 2019/0010256 A1* | 1/2019 | Lee ..................... C08F 10/02 |

FOREIGN PATENT DOCUMENTS

| | | |
|---|---|---|
| JP | H11-251067 | 9/1999 |
| JP | 2990307 | 12/1999 |
| JP | 2010080343 | 4/2010 |
| KR | 10-20000051826 | 8/2000 |
| KR | 10-20080069190 | 7/2008 |
| KR | 10-20090098589 | 9/2009 |
| KR | 10-20140037391 | 3/2014 |
| KR | 10-20150098181 | 8/2015 |
| WO | 2003012890 | 2/2003 |
| WO | 2007058172 | 5/2007 |

* cited by examiner

[FIG. 1]
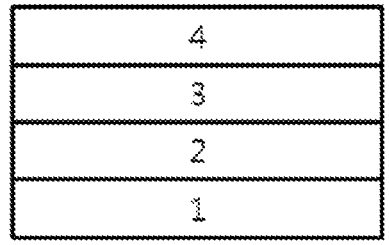
[FIG. 2]
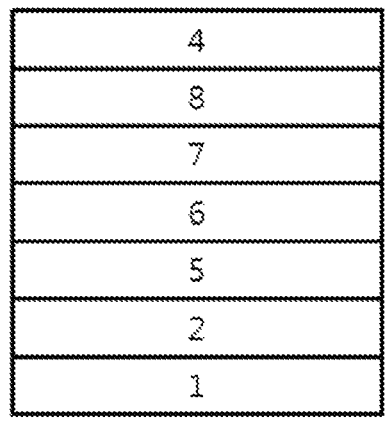
[FIG. 3]
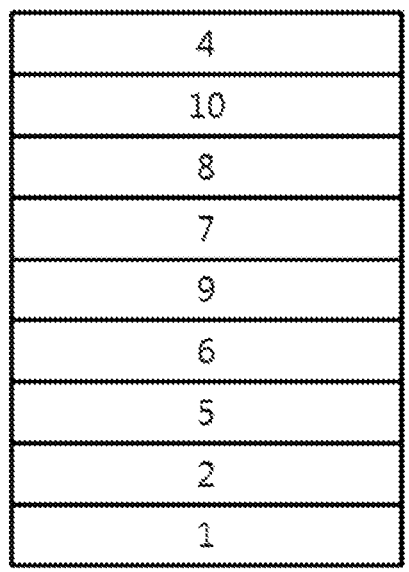

[FIG. 4]

| |
|---|
| 4 |
| 10 |
| 18 |
| 17 |
| 16 |
| 15 |
| 14 |
| 13 |
| 12 |
| 9 |
| 11 |
| 5 |
| 2 |
| 1 |

COMPOUND AND ORGANIC LIGHT EMITTING DEVICE COMPRISING SAME

CROSS-REFERENCE TO RELATED APPLICATION(S)

This application is a National Stage Application of International Application No. PCT/KR2018/012273 filed on Oct. 17, 2018, which claims priority to or the benefit of Korean Patent Application No. 10-2017-0136519 filed with the Korean Intellectual Property Office on Oct. 20, 2017 and Korean Patent Application No. 10-2018-0123424 filed with the Korean Intellectual Property Office on Oct. 16, 2018, the disclosures of which are incorporated herein by reference in their entirety.

TECHNICAL FIELD

The present invention relates to a novel compound and to an organic light emitting device comprising the same.

BACKGROUND

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer can be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for the organic materials used in the organic light emitting devices as described above.

PRIOR ART LITERATURE

Patent Literature (Patent Literature 0001) Korean Unexamined Patent Publication No. 10-2000-0051826

BRIEF DESCRIPTION

Technical Problem

It is an object of the present invention to provide a novel compound and an organic light emitting device including the same.

Technical Solution

In one aspect of the invention, there is provided a compound of Chemical Formula 1:

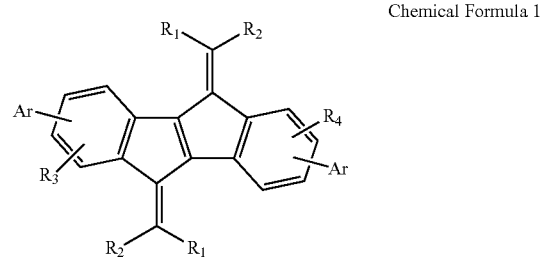

Chemical Formula 1 wherein, in Chemical Formula 1:

$R_1$ and $R_2$ are each independently hydrogen, a substituted or unsubstituted $C_{1-60}$ alkyl, a substituted or unsubstituted $C_{1-60}$ alkoxy, a substituted or unsubstituted $C_{1-60}$ haloalkyl, a substituted or unsubstituted $C_{1-60}$ haloalkoxy, halogen, cyano, tri($C_{1-60}$ alkyl)silyl, a substituted or unsubstituted $C_{6-60}$ aryl, or a substituted or unsubstituted $C_{2-60}$ heteroaryl containing at least one of O, N, Si and S;

$R_3$ and $R_4$ are each independently hydrogen, deuterium, a substituted or unsubstituted $C_{1-60}$ alkyl, a substituted or unsubstituted $C_{1-60}$ alkoxy, a substituted or unsubstituted $C_{1-60}$ haloalkyl, a substituted or unsubstituted $C_{1-60}$ haloalkoxy, halogen, cyano, tri($C_{1-60}$ alkyl)silyl, or a substituted or unsubstituted $C_{2-60}$ heteroaryl containing at least one of O, N, Si and S; and Ar is $C_{6-60}$ aryl, or $C_{2-60}$ heteroaryl containing at least one of O, N, Si and S, wherein the $C_{6-60}$ aryl, or $C_{2-60}$ heteroaryl is substituted with 1 to 5 substituents each selected from the group consisting of a substituted or unsubstituted $C_{1-60}$ alkyl, a substituted or unsubstituted $C_{1-60}$ alkoxy, a substituted or unsubstituted $C_{1-60}$ haloalkyl, a substituted or unsubstituted $C_{1-60}$ haloalkoxy, halogen, cyano, and tri($C_{1-60}$ alkyl)silyl.

In another aspect of the prevent invention, there is provided an organic light emitting device including a first electrode; a second electrode that is disposed opposite to the first electrode; and one or more organic material layers that are disposed between the first electrode and the second electrode, wherein one or more layers of the organic material layers include the compound of Chemical Formula 1.

Advantageous Effects

The compound of Chemical Formula 1 described above can be used as a material of an organic material layer of an organic light emitting device, and can improve the efficiency, achieve low driving voltage and/or improve lifetime characteristics in the organic light emitting device. In particular, the compound of Chemical Formula 1 can be used as a hole injection material, hole transport material, hole injection and transport material, light emitting material, electron transport material, or electron injection material.

BRIEF DESCRIPTION OF THE DRAWINGS

FIG. 1 shows an example of an organic light emitting device comprising a substrate 1, an anode 2, a light emitting layer 3, and a cathode 4.

FIG. 2 shows an example of an organic light emitting device comprising a substrate 1, an anode 2, a hole injection layer 5, a hole transport layer 6, a light emitting layer 7, an electron transport layer 8 and a cathode 4.

FIG. 3 shows an example of an organic light emitting device comprising a substrate 1, an anode 2, a hole injection layer 5, a hole transport layer 6, an electron blocking layer 9, a light emitting layer 7, an electron transport layer 8, an electron injection layer 10 and a cathode 4.

FIG. 4 shows an example of an organic light emitting device comprising a substrate 1, an anode 2, a hole injection layer 5, a first hole transport layer 11, an electron blocking layer 9, a first light emitting layer 12, a first electron transport layer 13, a N-type charge generating layer 14, a P-type charge generating layer 15, a second hole transport layer 16, a second light emitting layer 17, a second electron transport layer 18, an electron injection layer 10 and a cathode 4.

DETAILED DESCRIPTION

Hereinafter, embodiments of the present invention will be described in more detail to facilitate understanding of the invention.

The present invention provides a compound of Chemical Formula 1.

As used herein, the notation

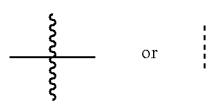

means a bond linked to another substituent group.

As used herein, the term "substituted or unsubstituted" means being unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a heterocyclic group containing at least one of N, O and S atoms, or being unsubstituted or substituted with a substituent to which two or more substituents are linked among the substituents exemplified above. For example, "the substituent to which two or more substituents are linked" can be a biphenyl group. That is, the biphenyl group can also be an aryl group and can be interpreted as a substituent to which two phenyl groups are linked.

In the present specification, the number of carbon atoms of a carbonyl group is not particularly limited, but is preferably 1 to 40. Specifically, the carbonyl group can be a compound having the following structural formulas, but is not limited thereto:

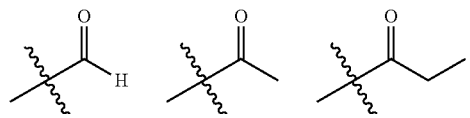

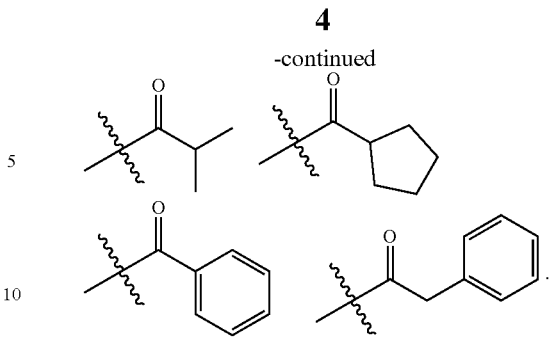

In the present specification, an ester group can have a structure in which oxygen of the ester group can be substituted by a straight-chain, branched-chain, or cyclic alkyl group having 1 to 25 carbon atoms, or an aryl group having 6 to 25 carbon atoms. Specifically, the ester group can be a compound having the following structural formulas, but is not limited thereto:

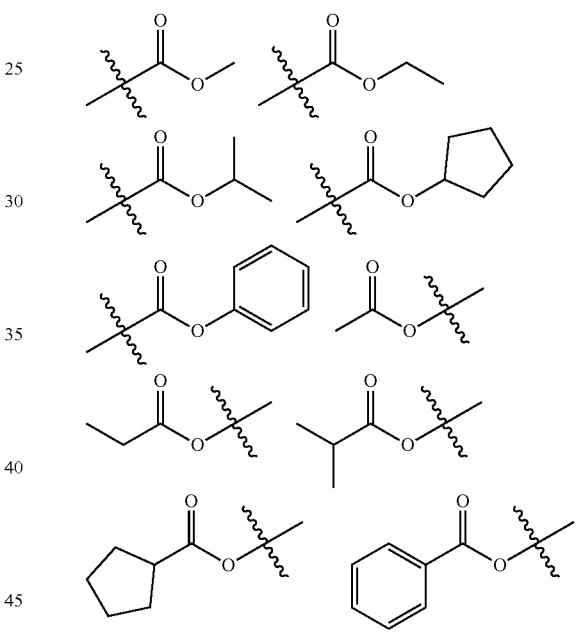

In the present specification, the number of carbon atoms of an imide group is not particularly limited, but is preferably 1 to 25. Specifically, the imide group can be a compound having the following structural formulas, but is not limited thereto:

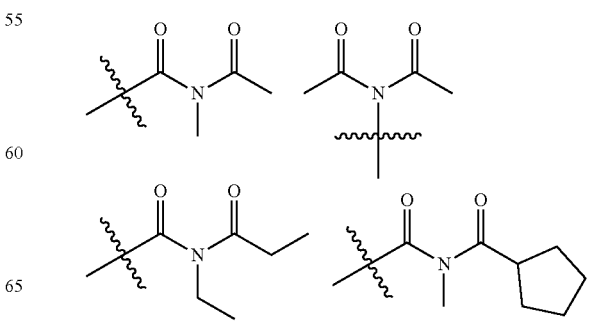

-continued

[Structure showing an amide group with methyl substituent and benzoyl group]

In the present specification, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present specification, a boron group specifically includes a trimethylboron group, a triethylboron group, a t-butyldimethylboron group, a triphenylboron group, and a phenylboron group, but is not limited thereto.

In the present specification, examples of a halogen group include fluorine, chlorine, bromine, or iodine.

In the present specification, the alkyl group can be straight-chain or branched-chain, and the number of carbon atoms thereof is not particularly limited, but is preferably 1 to 40. According to one embodiment, the number of carbon atoms of the alkyl group is 1 to 20. According to another embodiment, the number of carbon atoms of the alkyl group is 1 to 10. According to another embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentyl-methyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the alkenyl group can be straight-chain or branched-chain, and the number of carbon atoms thereof is not particularly limited, but is preferably 2 to 40. According to one embodiment, the number of carbon atoms of the alkenyl group is 2 to 20. According to another embodiment, the number of carbon atoms of the alkenyl group is 2 to 10. According to still another embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but the number of carbon atoms thereof is preferably 3 to 60. According to one embodiment, the number of carbon atoms of the cycloalkyl group is 3 to 30. According to another embodiment, the number of carbon atoms of the cycloalkyl group is 3 to 20. According to still another embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an aryl group is not particularly limited, but preferably has 6 to 60 carbon atoms, and it can be a monocyclic aryl group or a polycyclic aryl group. According to one embodiment, the number of carbon atoms of the aryl group is 6 to 30. According to one embodiment, the number of carbon atoms of the aryl group is 6 to 20. The aryl group can be a phenyl group, a biphenyl group, a terphenyl group or the like as the monocyclic aryl group, but is not limited thereto. The polycyclic aryl group includes a naphthyl group, an anthracenyl group, a phenanthryl group, a pyrenyl group, a perylenyl group, a chrysenyl group, a fluorenyl group or the like, but is not limited thereto.

In the present specification, a fluorenyl group can be substituted, and two substituent groups can be bonded to each other to form a spiro structure. In the case where the fluorenyl group is substituted,

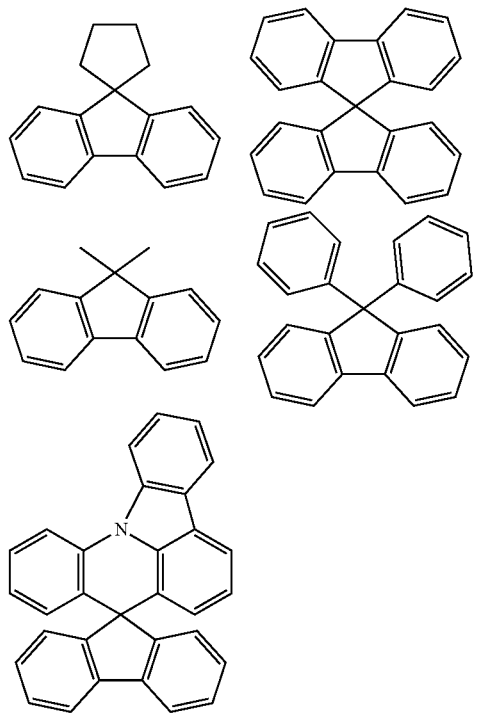

and the like can be formed. However, the structure is not limited thereto.

In the present specification, a heterocyclic group is a heterocyclic group including one or more of O, N, Si and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazol group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

In the present specification, the aryl group in the aralkyl group, the aralkenyl group, the alkylaryl group and the arylamine group is the same as the aforementioned examples of the aryl group. In the present specification, the alkyl group in the aralkyl group, the alkylaryl group and the alkylamine group is the same as the aforementioned examples of the alkyl group. In the present specification, the heteroaryl in the heteroarylamine can be applied to the aforementioned description of the heterocyclic group. In the present specification, the alkenyl group in the aralkenyl group is the same as the aforementioned examples of the alkenyl group. In the present specification, the aforementioned description of the aryl group can be applied except that the arylene is a divalent group. In the present specification, the aforementioned description of the heterocyclic group can be applied except that the heteroarylene is a divalent group. In the present specification, the aforementioned description of the aryl group or cycloalkyl group can be applied except that the hydrocarbon ring is not a monovalent group but formed by combining two substituent groups. In the present specification, the aforementioned description of the heterocyclic group can be applied, except that the heterocyclic group is not a monovalent group but formed by combining two substituent groups.

Preferably, in Chemical Formula 1, $R_1$ and $R_2$ are each independently cyano or 2,3,5,6-tetrafluoro-4-cyanophenyl.

Preferably, $R_3$ and $R_4$ are each independently hydrogen or deuterium.

Preferably, the compound of Chemical Formula 1 is one of the following Chemical Formulas 1-1, 1-2, 1-3, or 1-4:

Chemical Formula 1-1

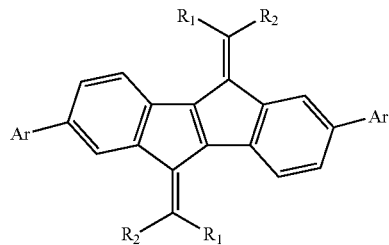

Chemical Formula 1-2

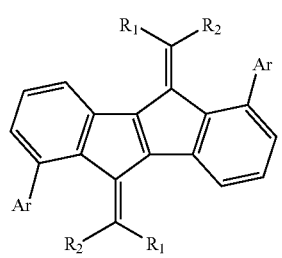

Chemical Formula 1-3

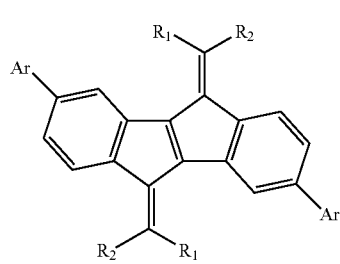

Chemical Formula 1-4

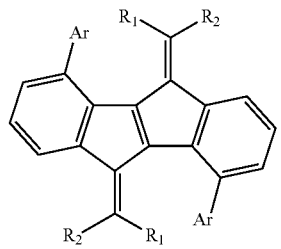

wherein, in Chemical Formulas 1-1, 1-2, 1-3 and 1-4:

$R_1$ and $R_2$ and Ar are the same as defined above.

Preferably, Ar is phenyl, wherein said phenyl is substituted with 1 to 5 substituents each selected from the group consisting of a substituted or unsubstituted $C_{1-60}$ alkyl, a substituted or unsubstituted $C_{1-60}$ alkoxy, a substituted or unsubstituted $C_{1-60}$ haloalkyl, a substituted or unsubstituted $C_{1-60}$ haloalkoxy, halogen, cyano, and tri($C_{1-60}$ alkyl)silyl.

Preferably, Ar is phenyl, wherein said phenyl is substituted with 1 to 5 substituents each selected from the group consisting of fluoro, trifluoromethyl, trifluoromethoxy, and cyano.

Preferably, Ar is any one selected from the group consisting of the following:

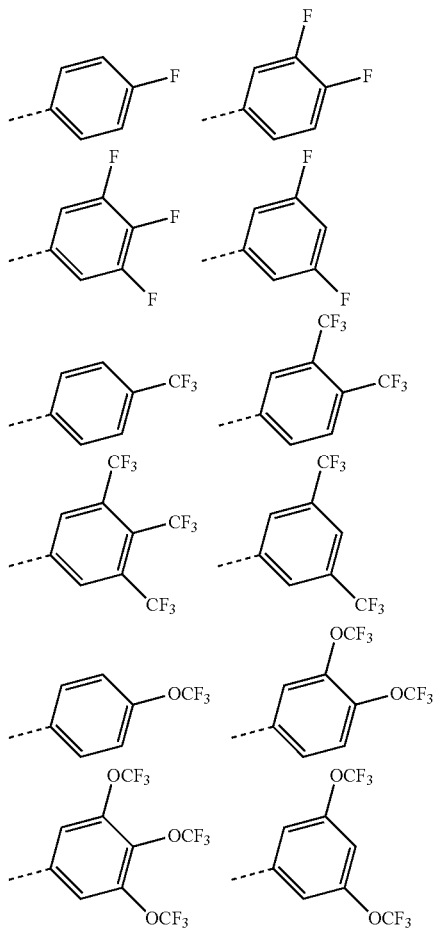

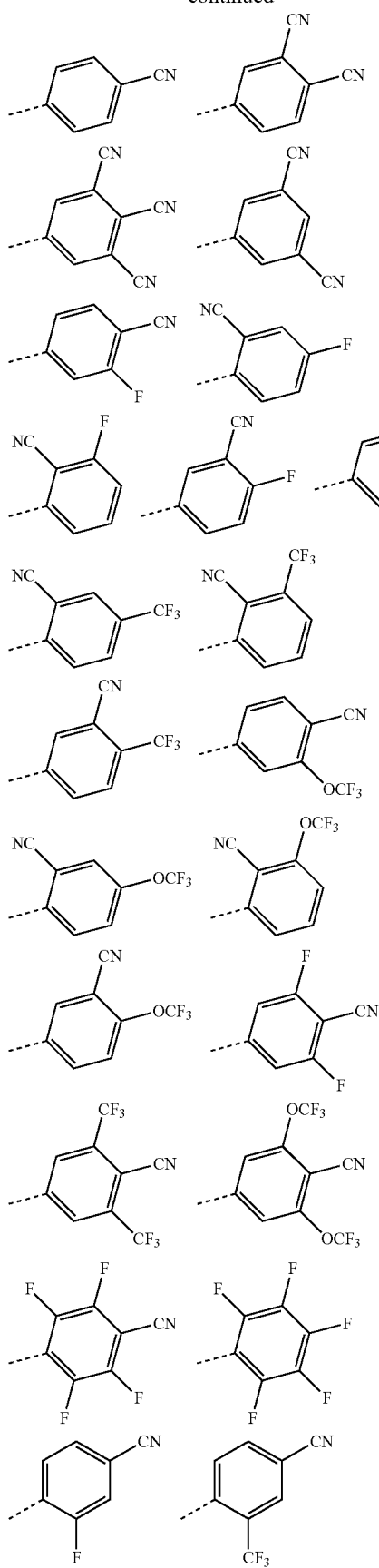
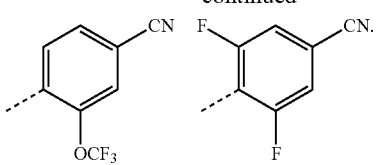
Representative examples of the compound of Chemical Formula 1 are as follows:
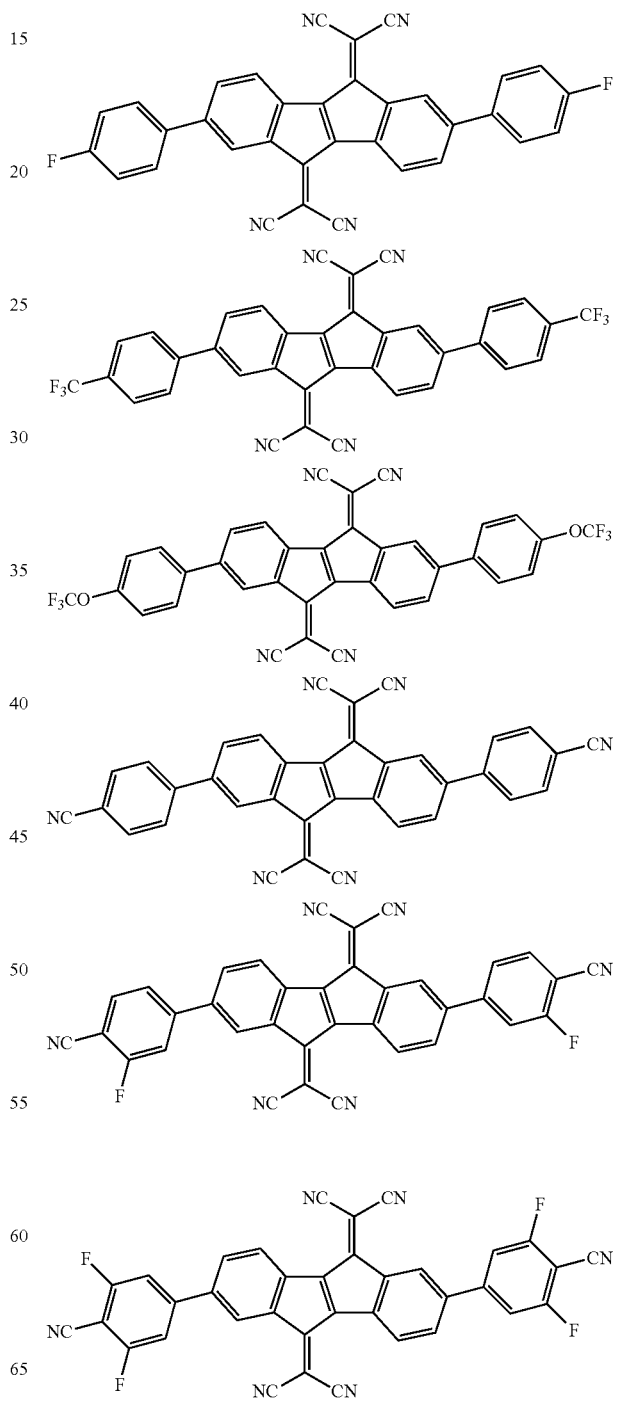

-continued
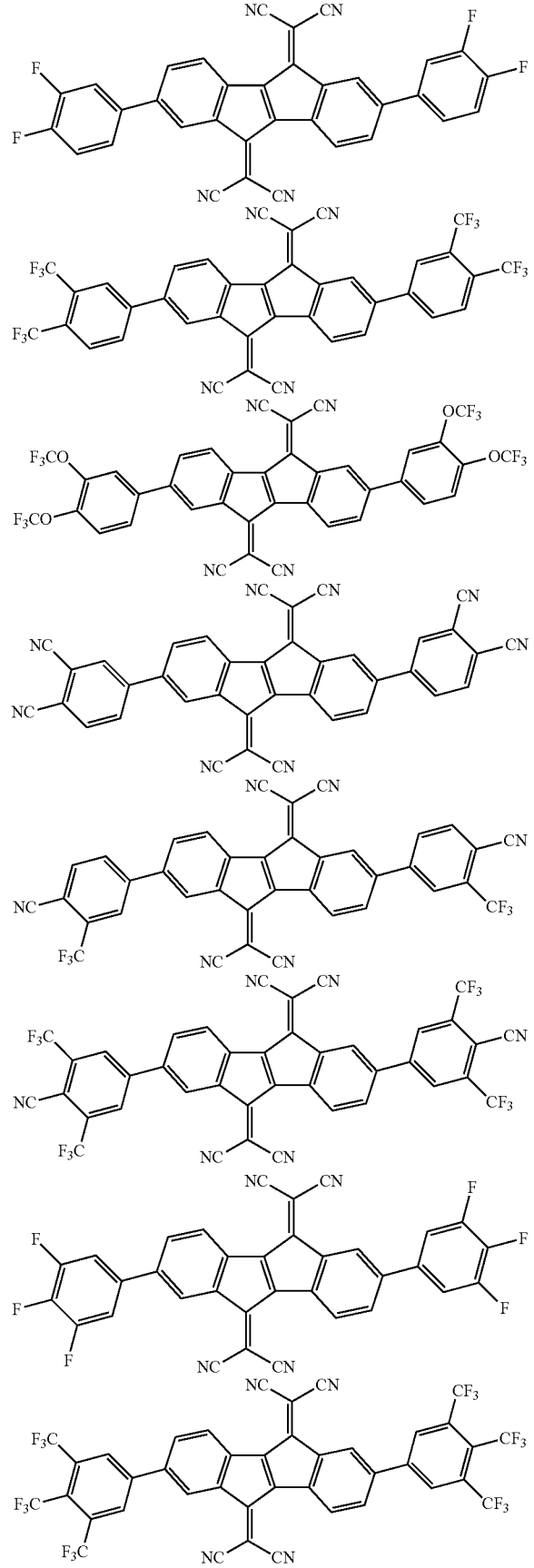
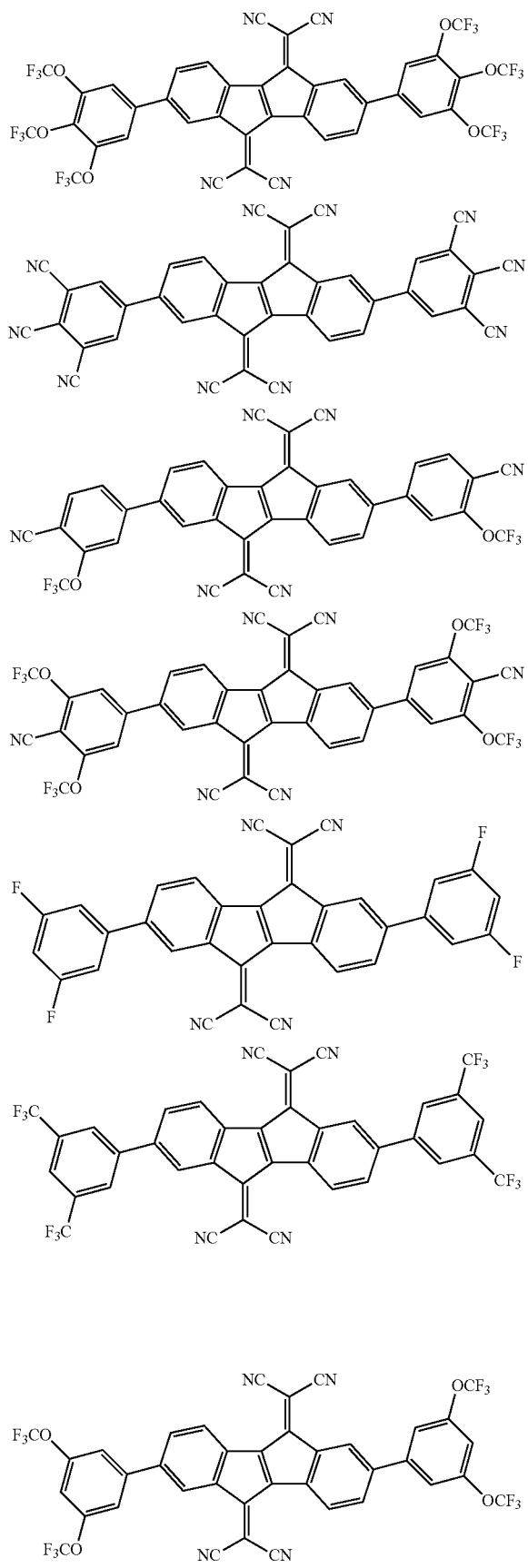

-continued
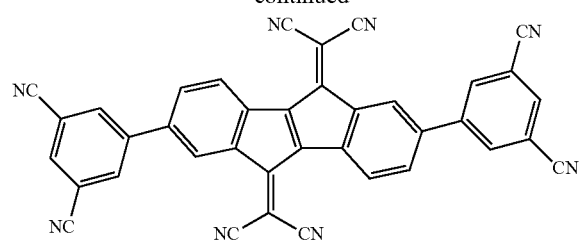
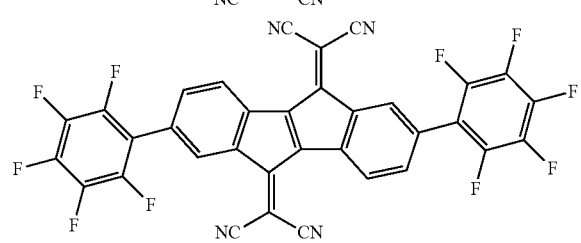
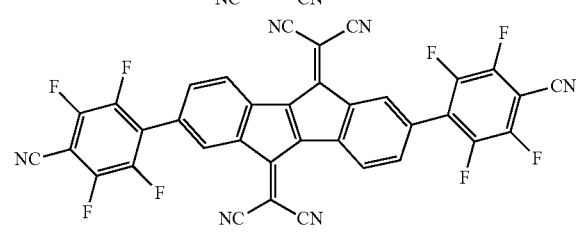
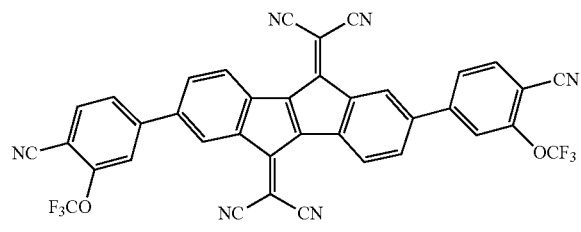
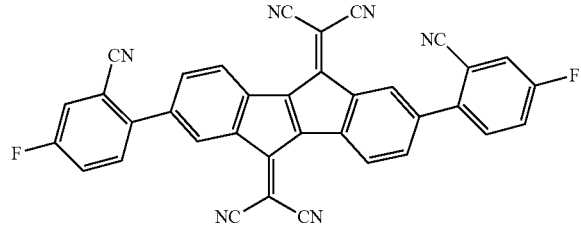
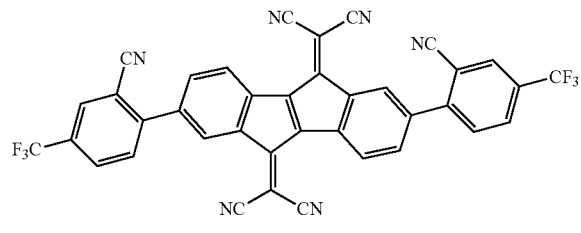
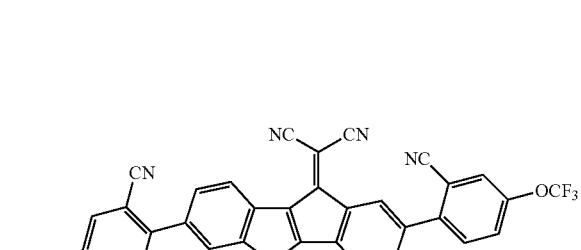
-continued
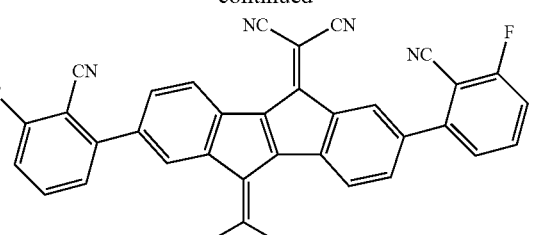
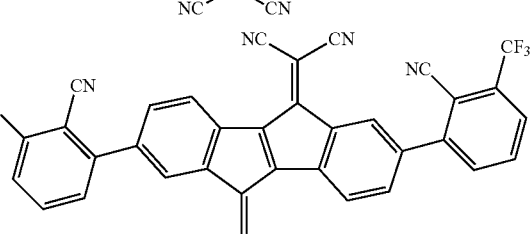
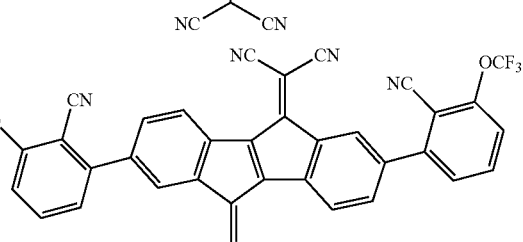
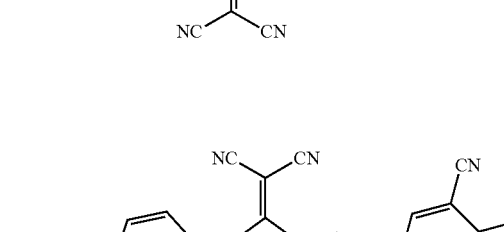
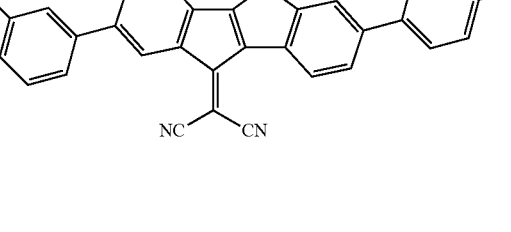
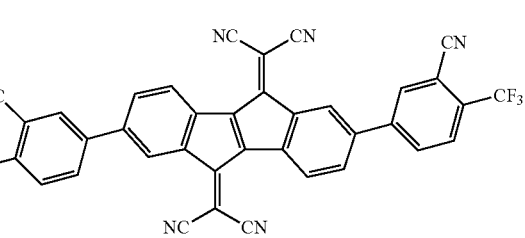
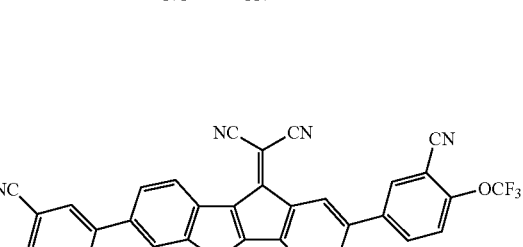

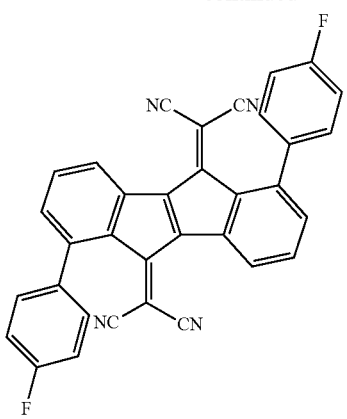
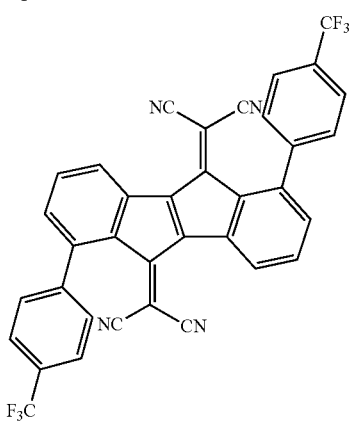
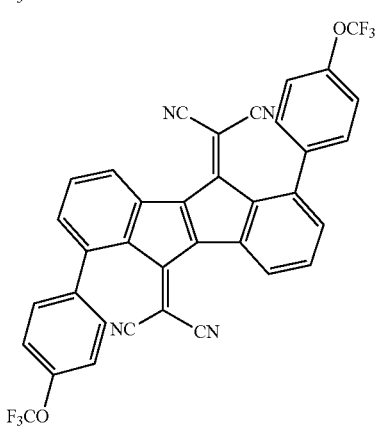
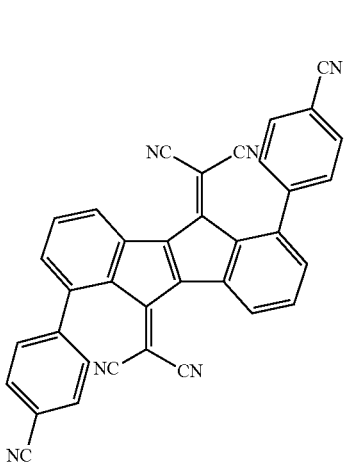
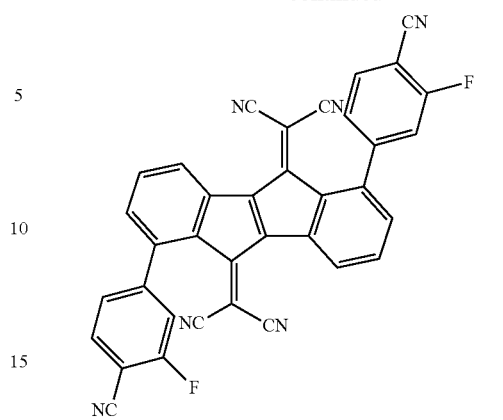
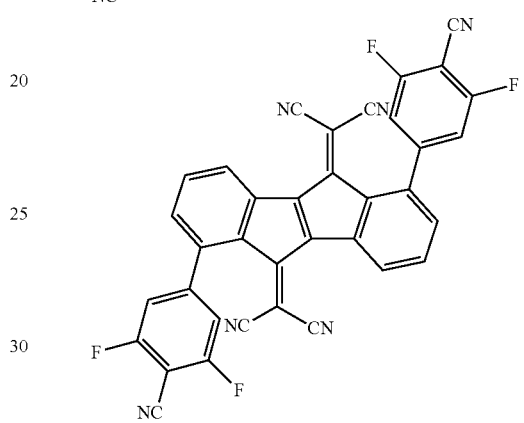
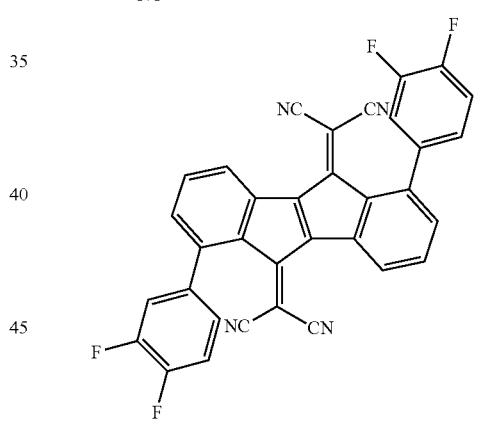
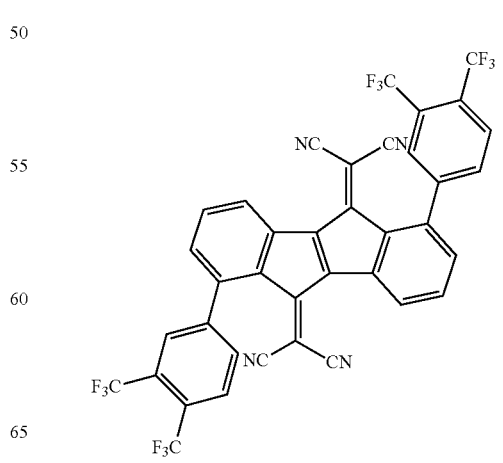

-continued
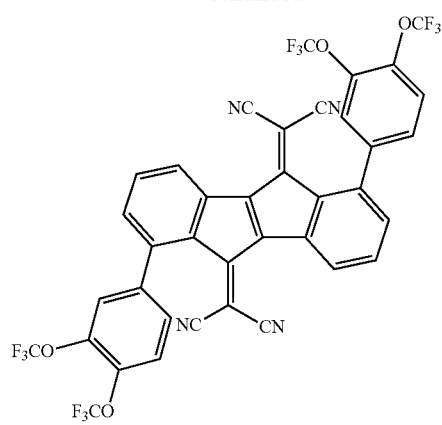
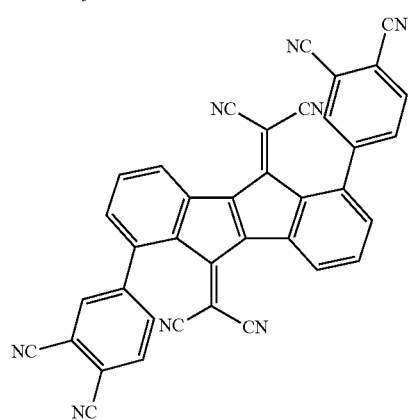
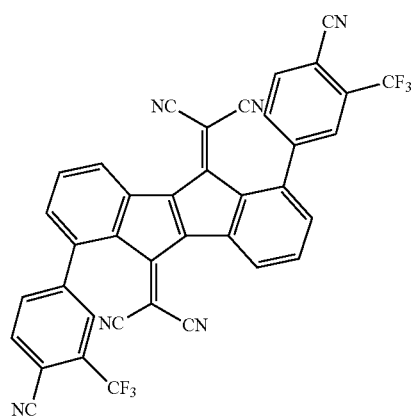
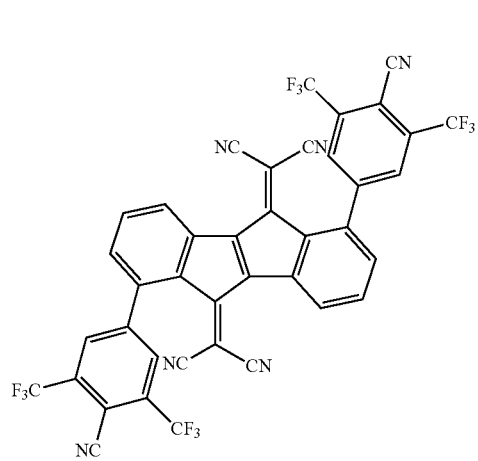
-continued
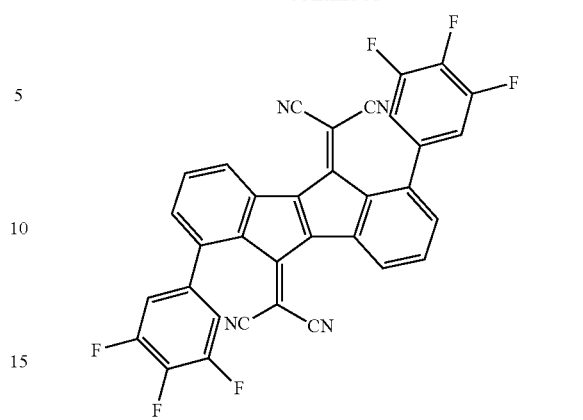
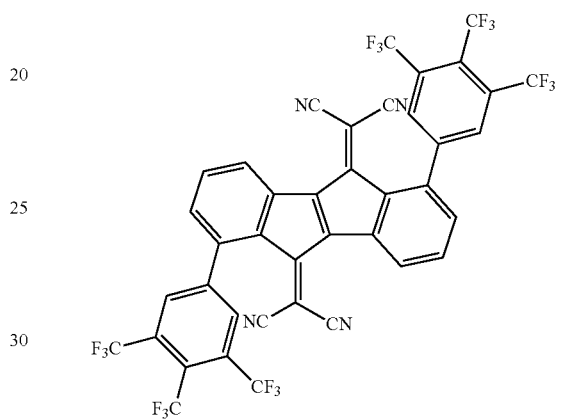
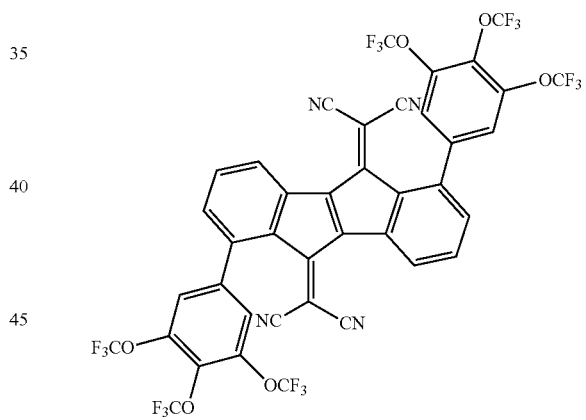
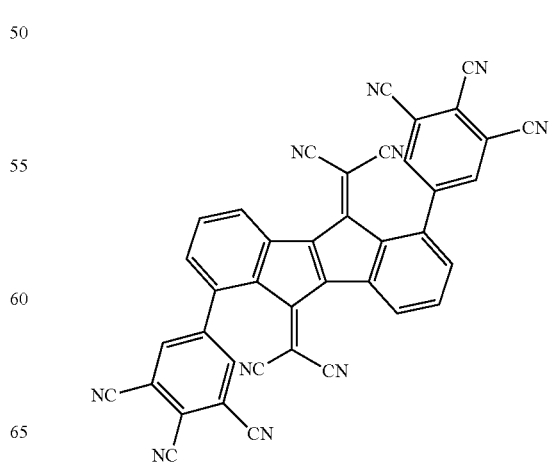

-continued
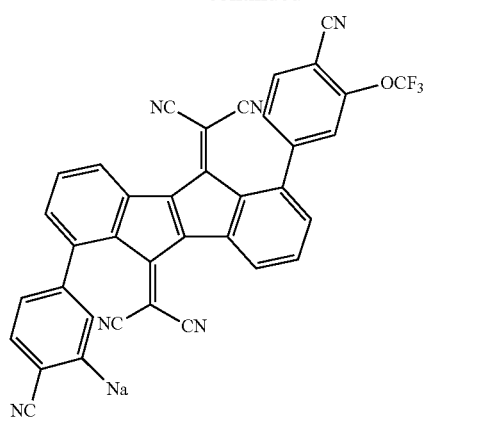
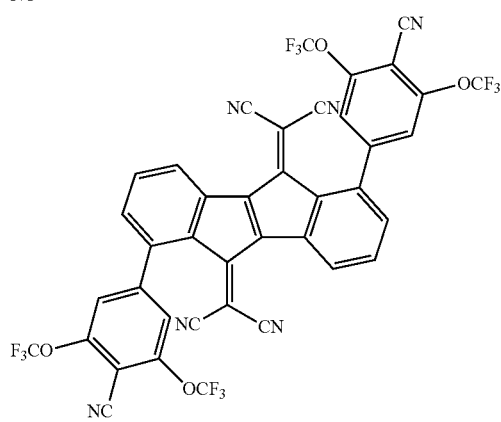
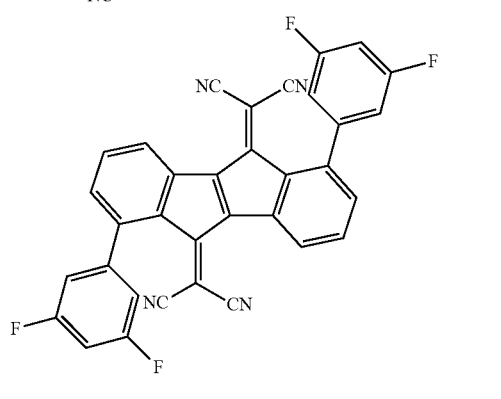
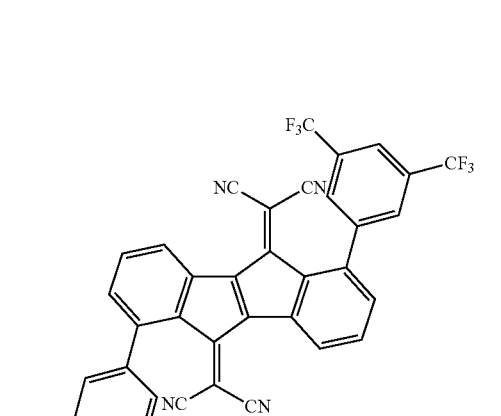
-continued
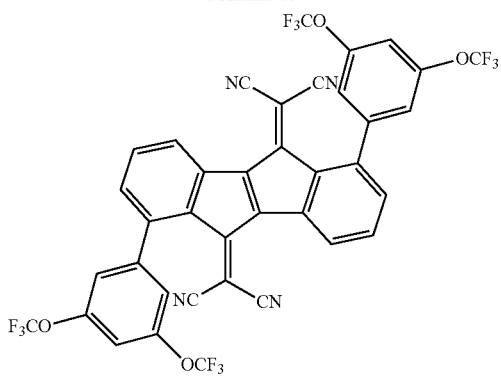
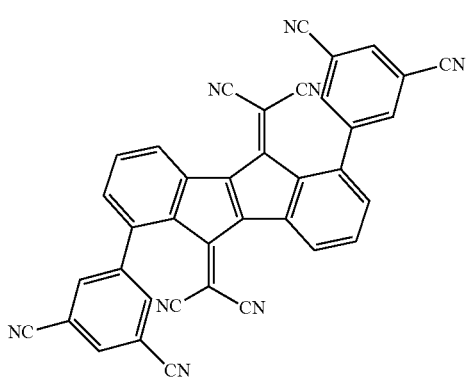
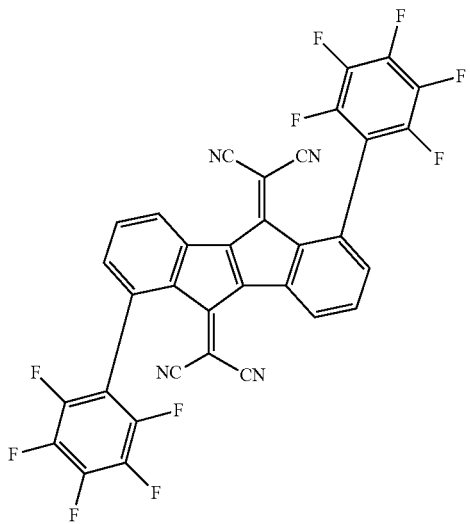

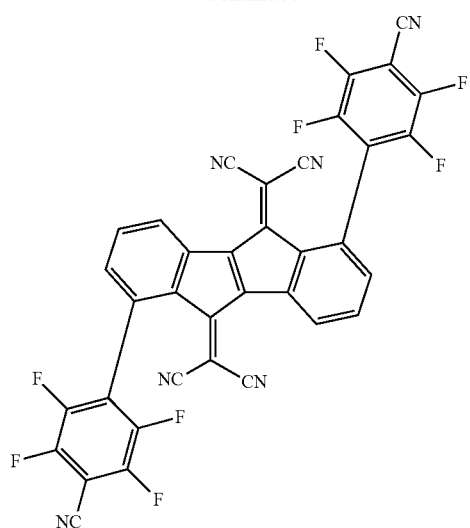 [SMILES: N#CC(C#N)=C1C2=C(C(=C(C#N)C#N)c3c2cccc3-c2c(F)c(F)c(C#N)c(F)c2F)c2cccc(-c3c(F)c(F)c(C#N)c(F)c3F)c21]
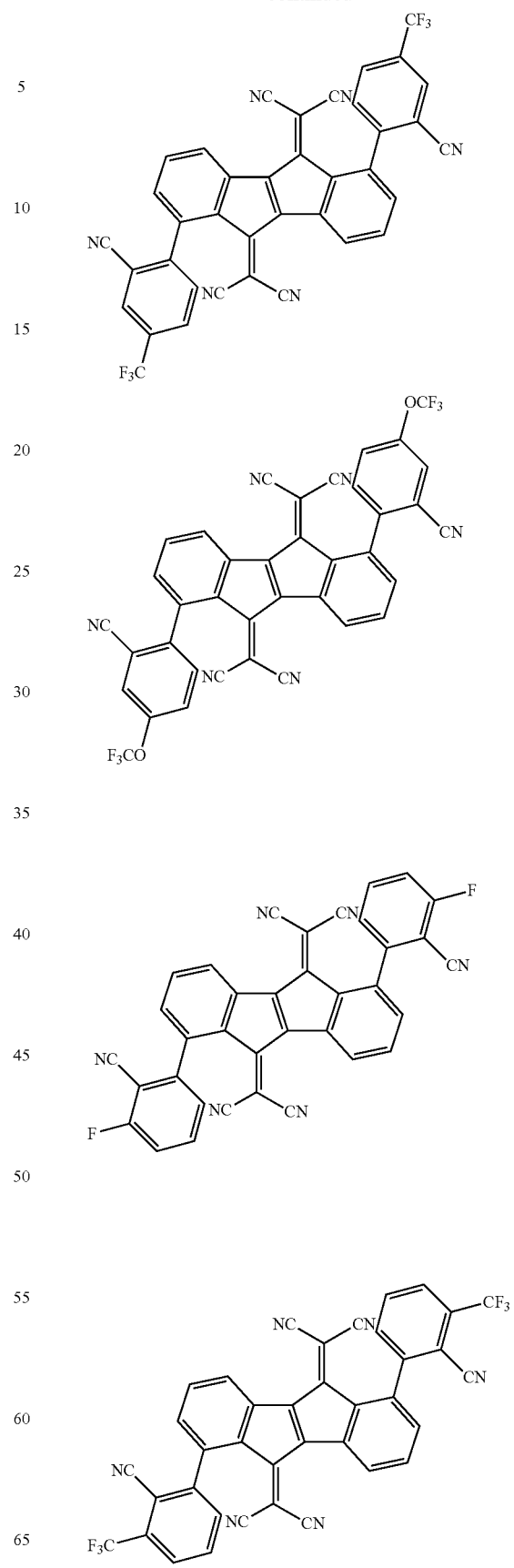

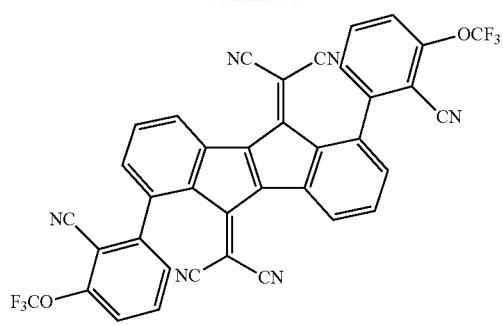
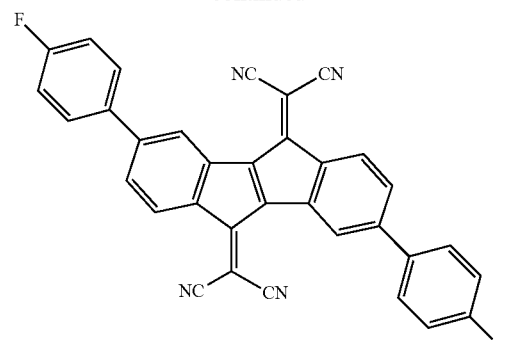
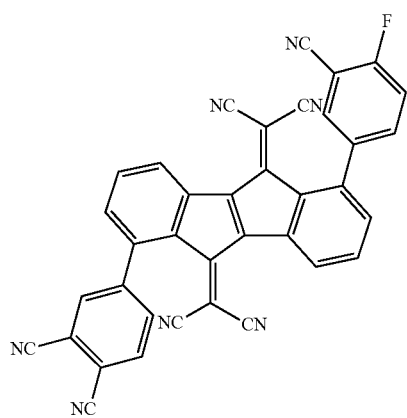
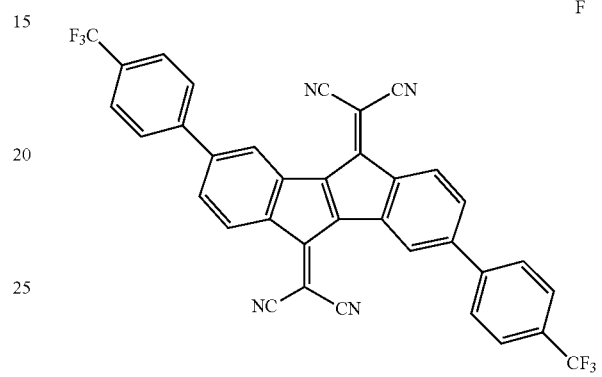
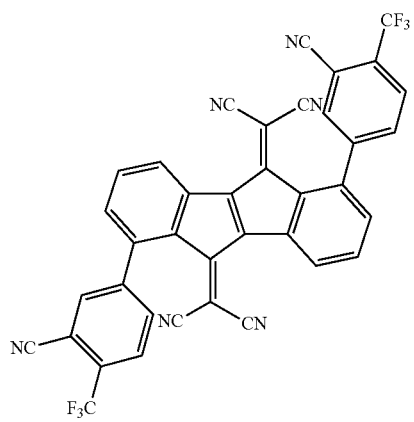
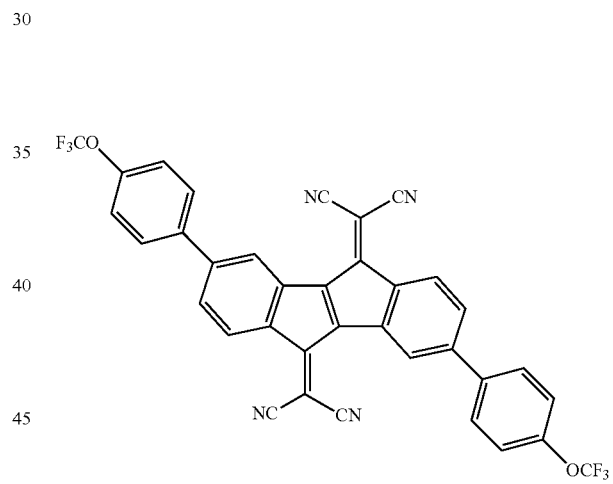
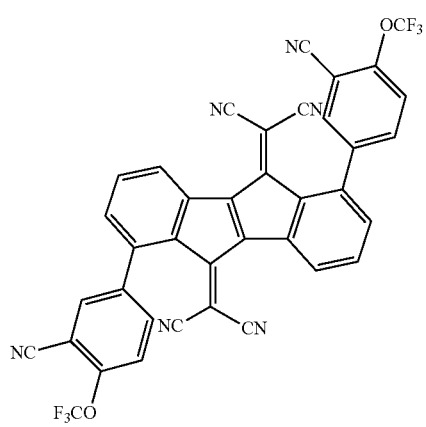
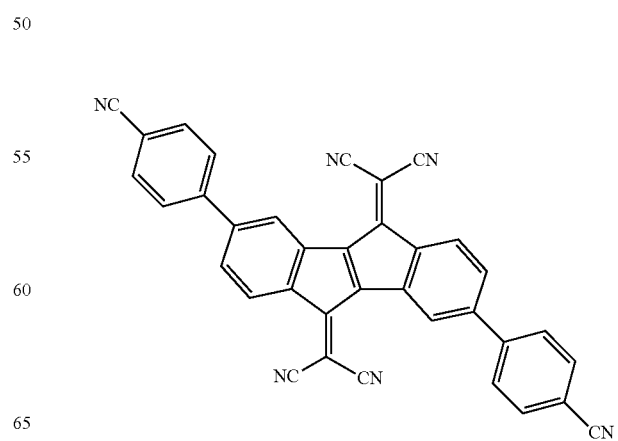

25
-continued
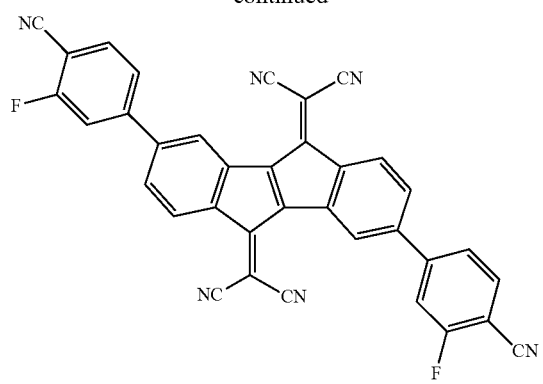
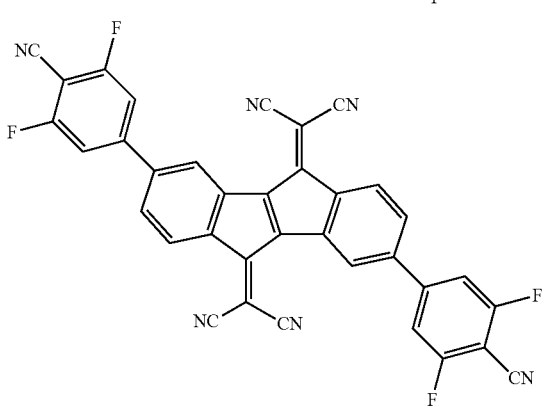
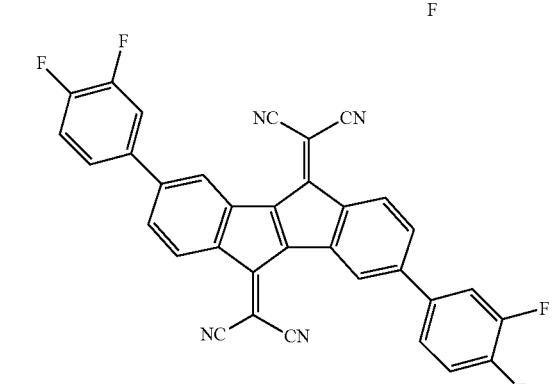
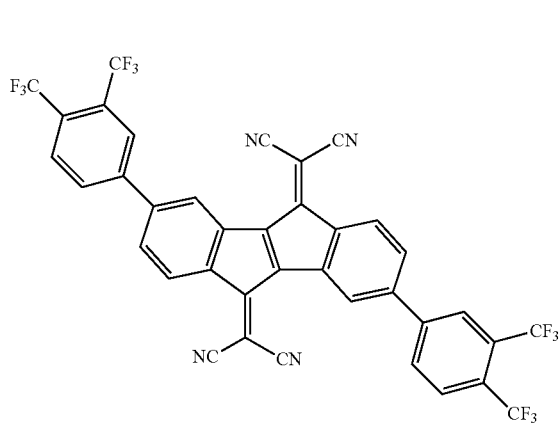
26
-continued
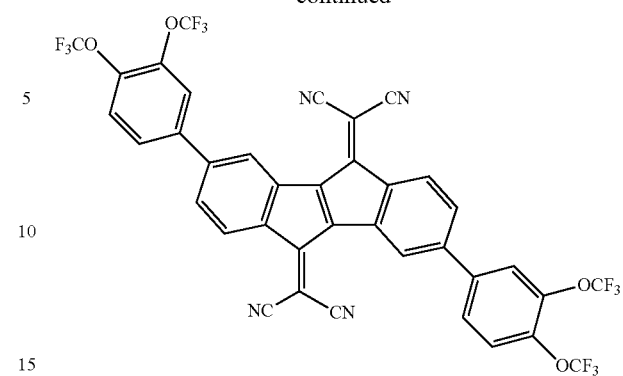
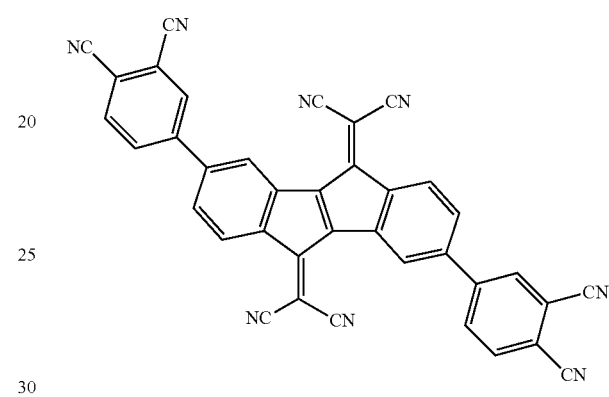
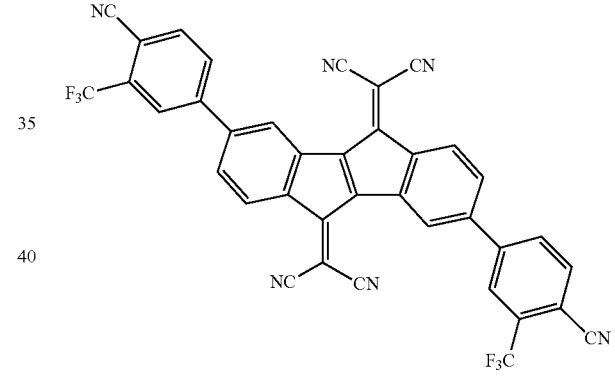
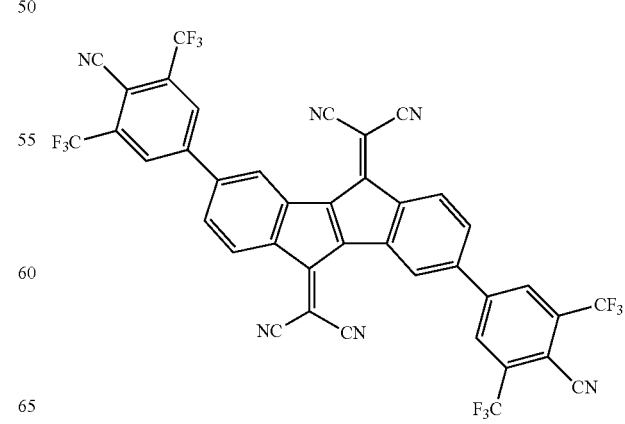

27
-continued
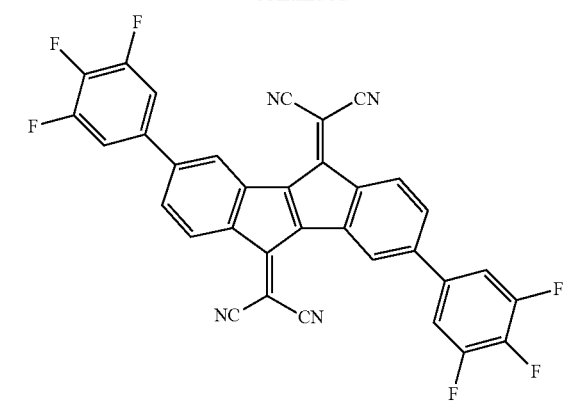
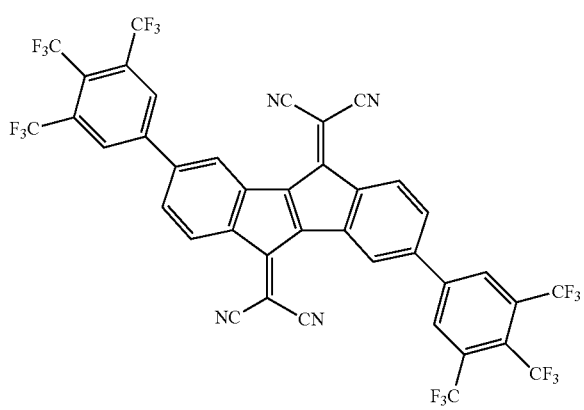
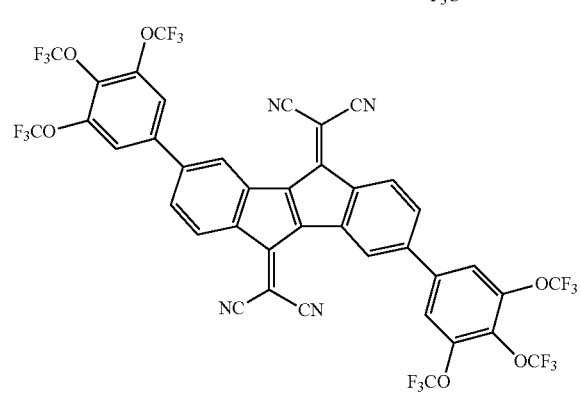
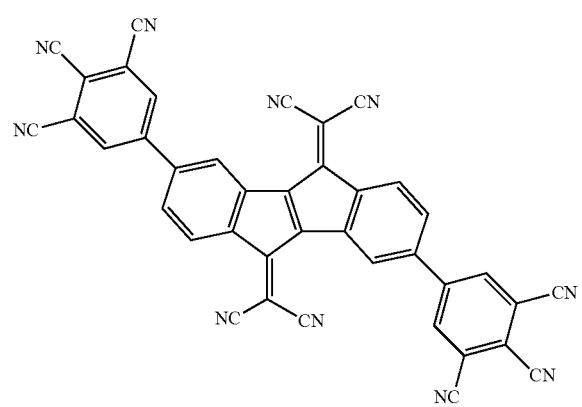
28
-continued
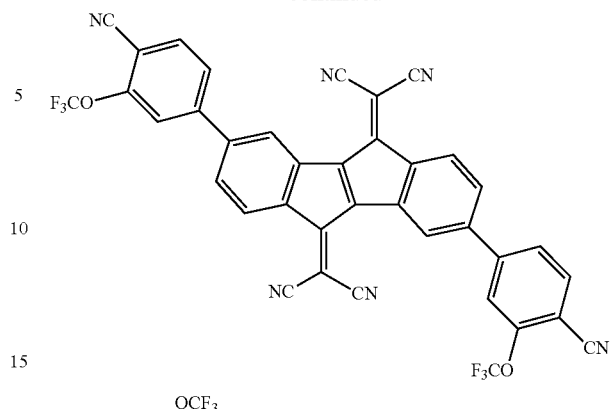
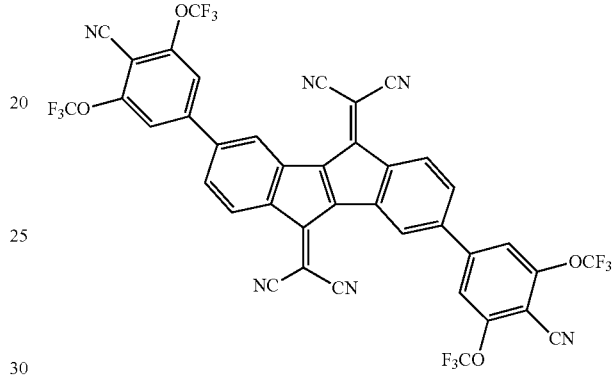
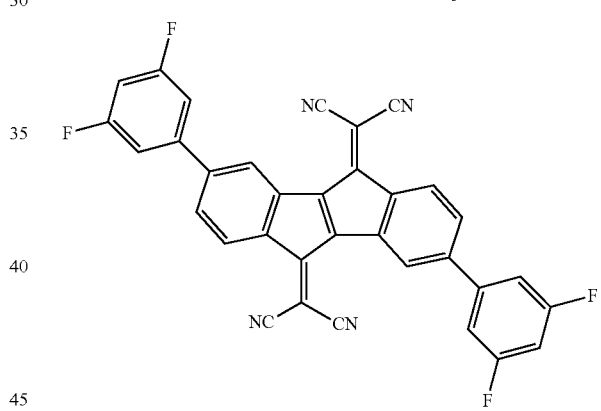
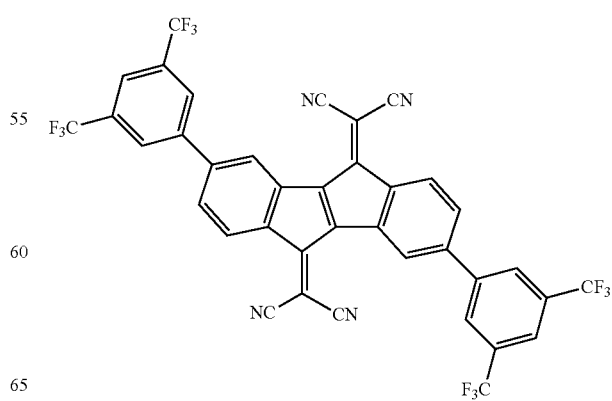

-continued
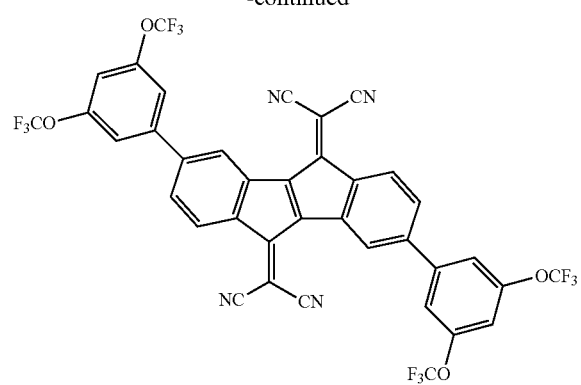
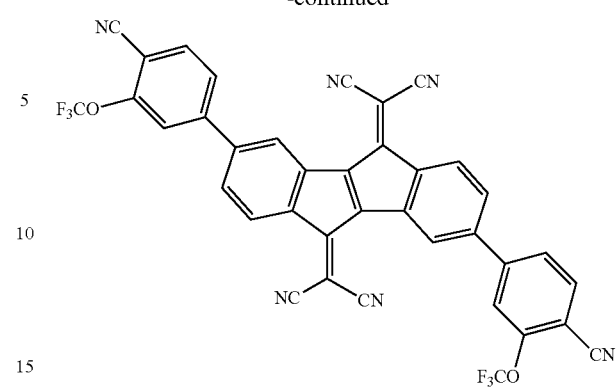
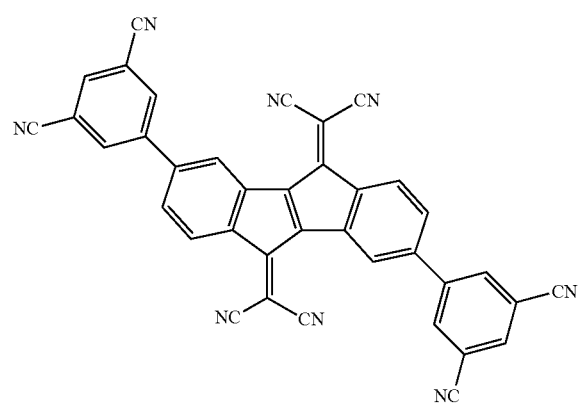
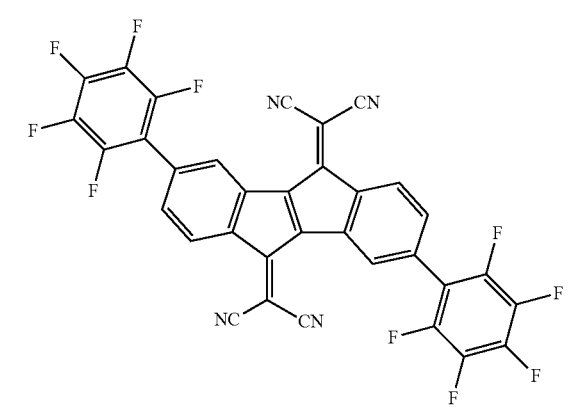
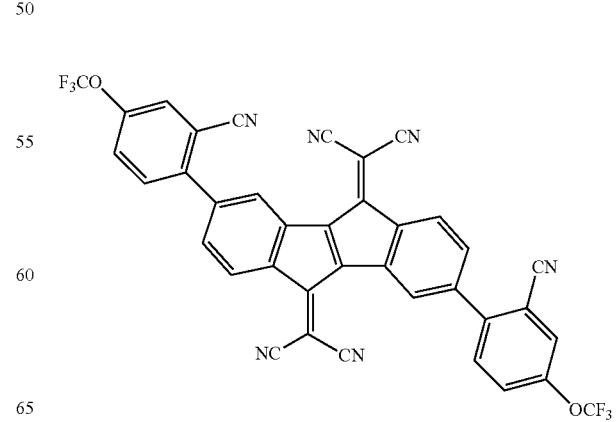
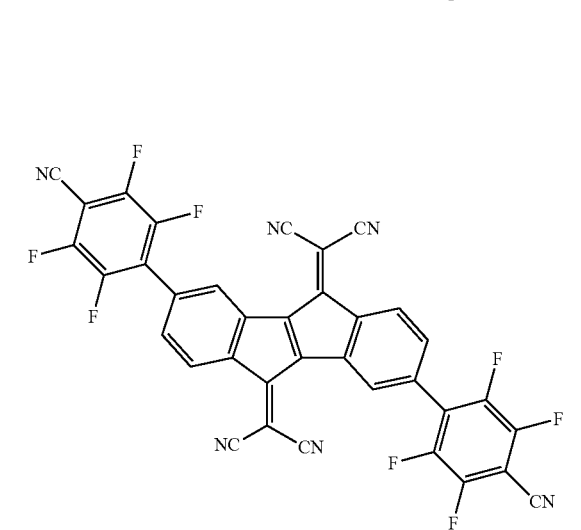

31
-continued
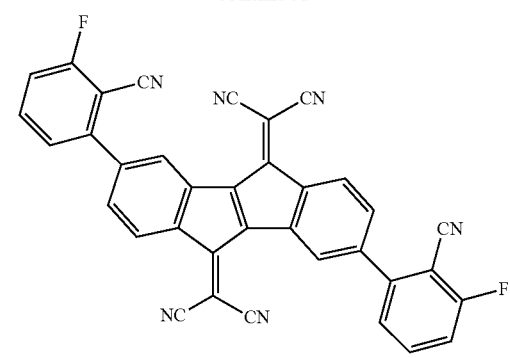
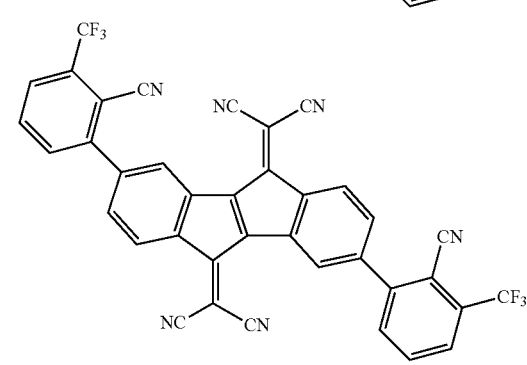
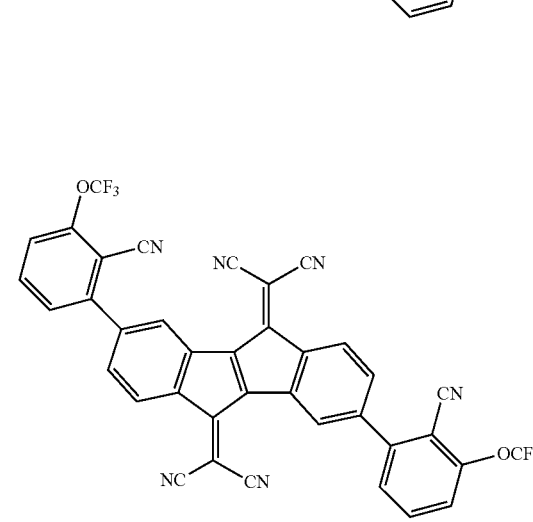
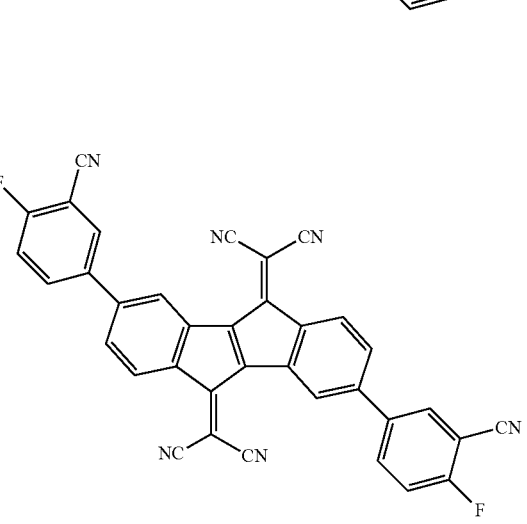
32
-continued
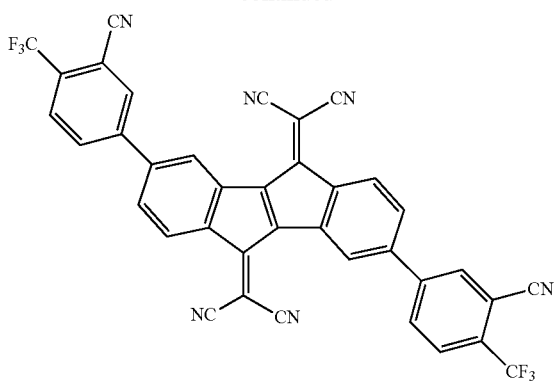
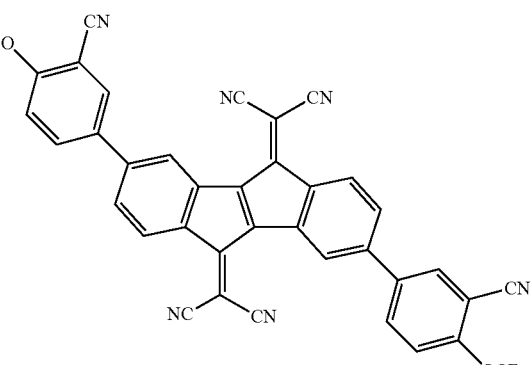
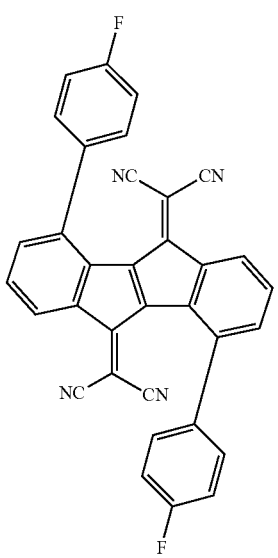

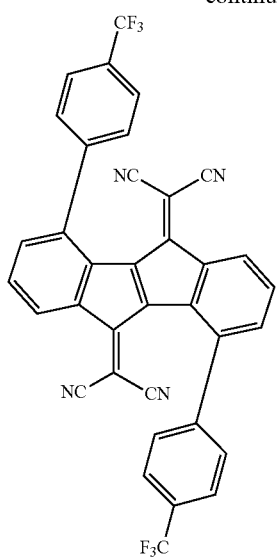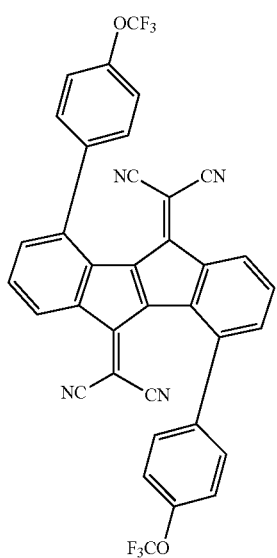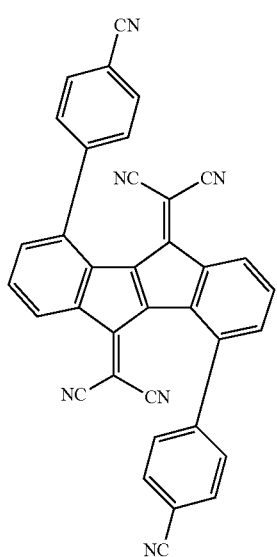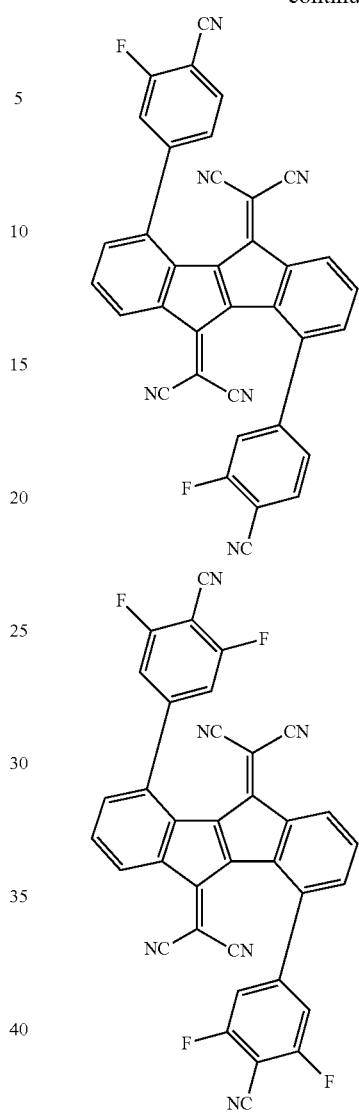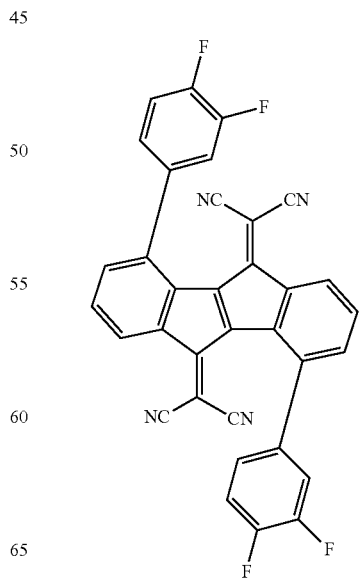

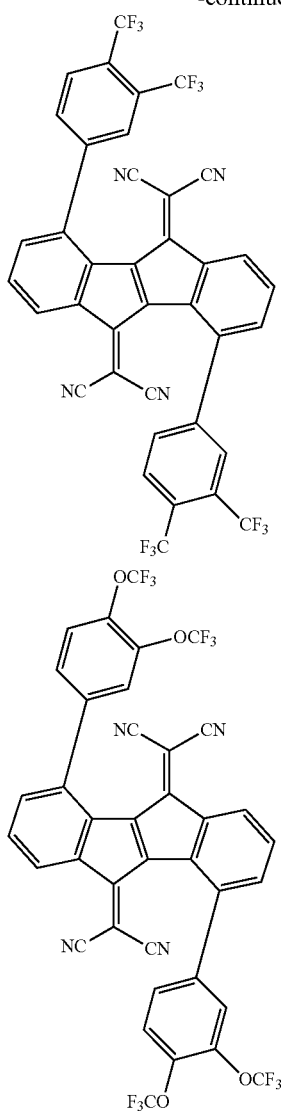
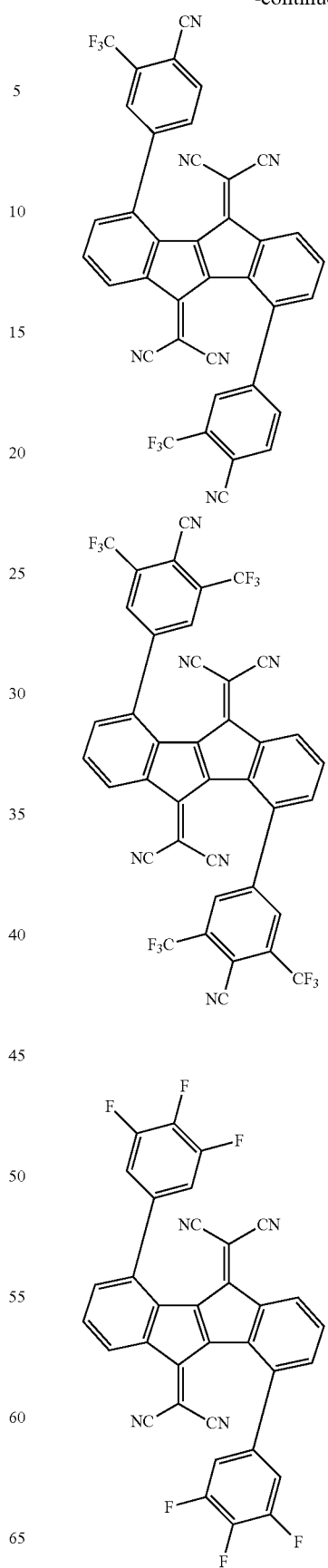

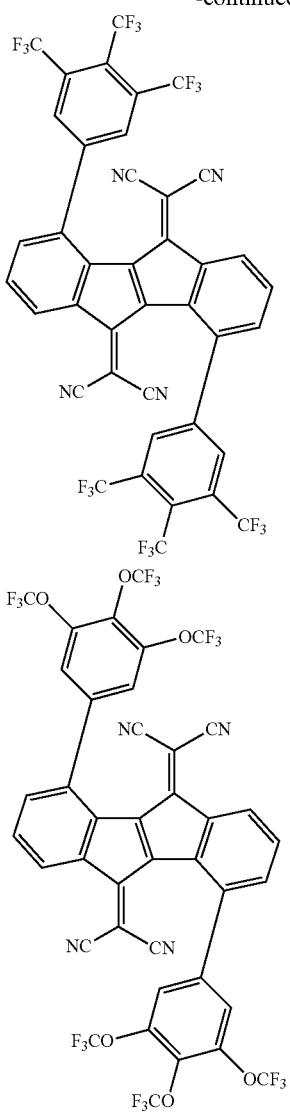
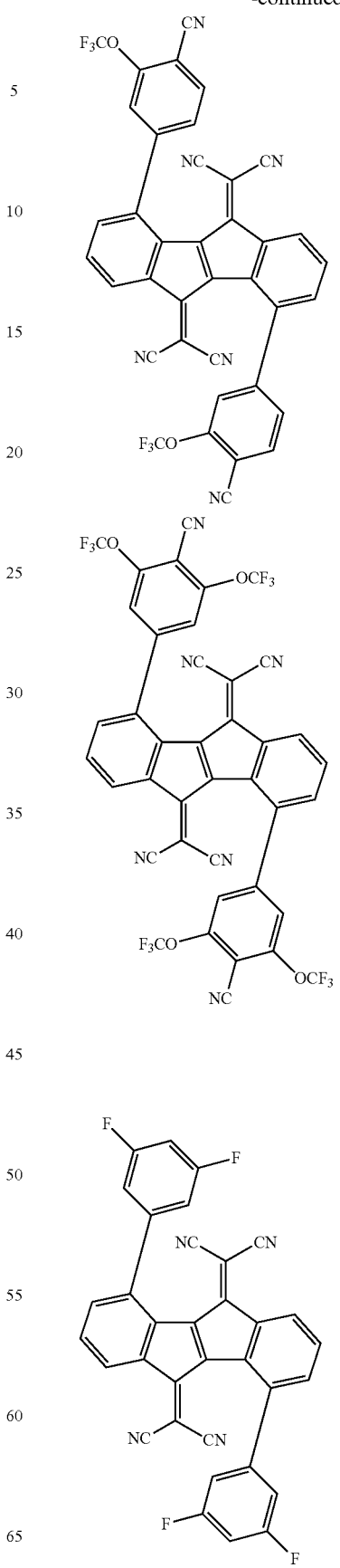

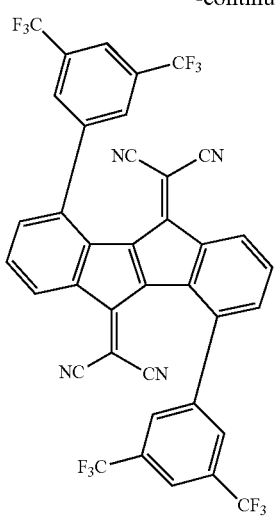
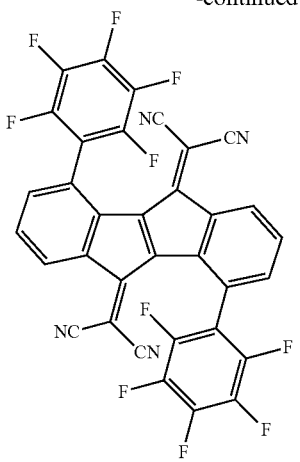
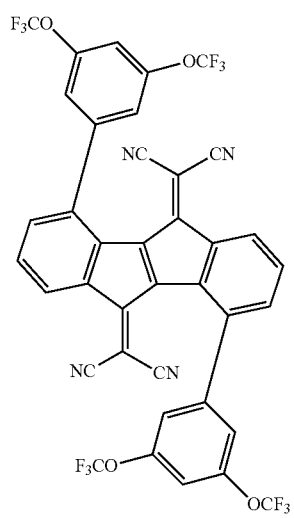
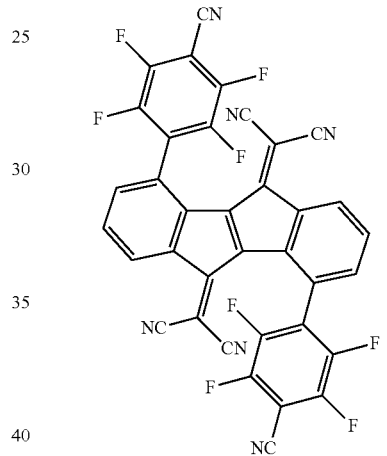
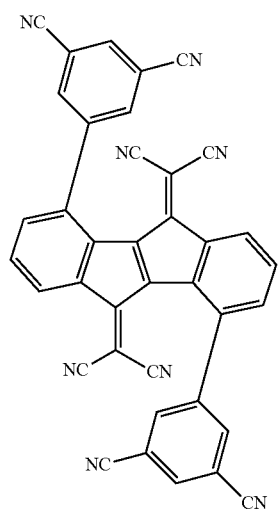
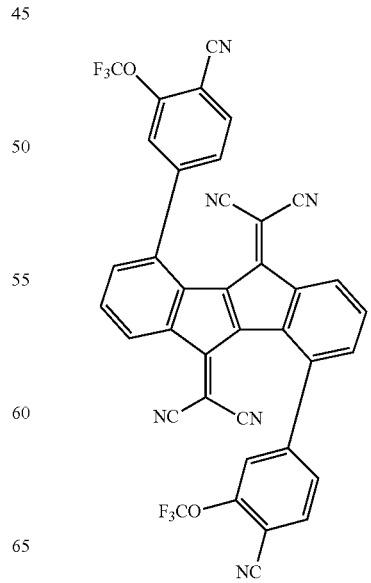

41
-continued
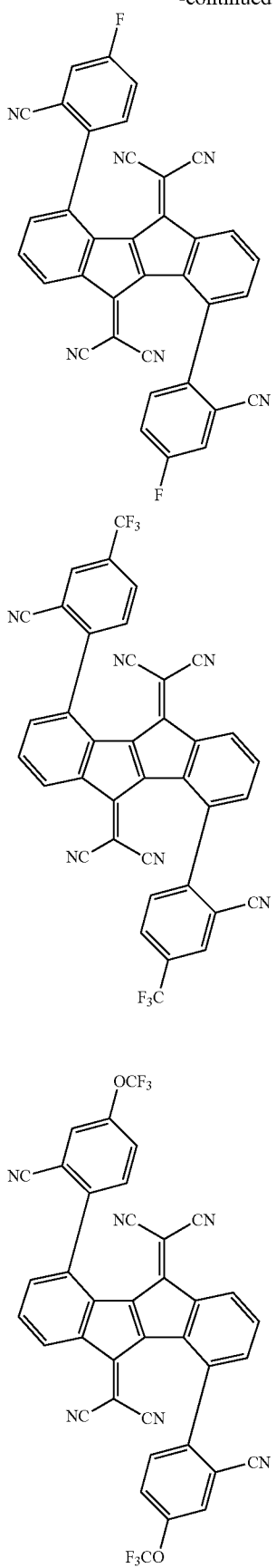
42
-continued
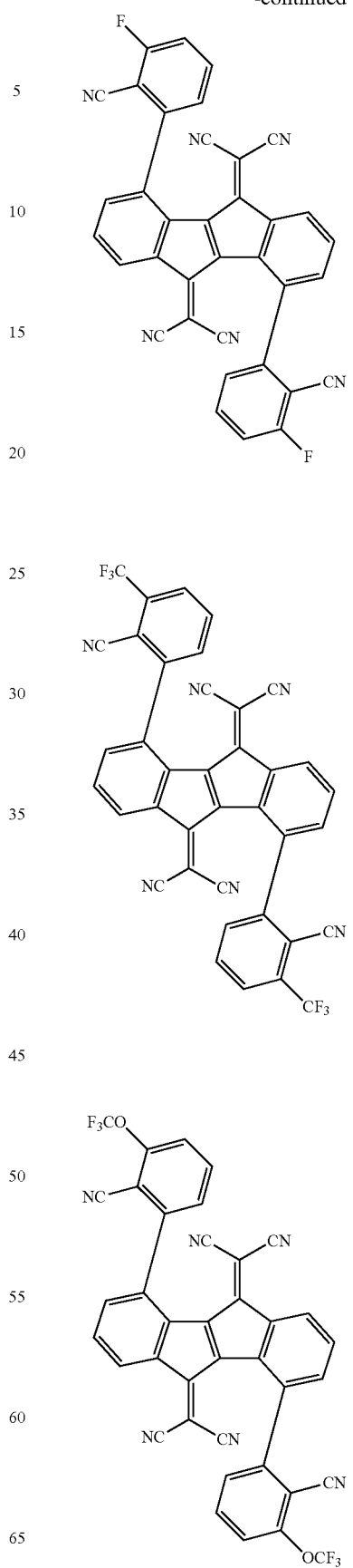

-continued
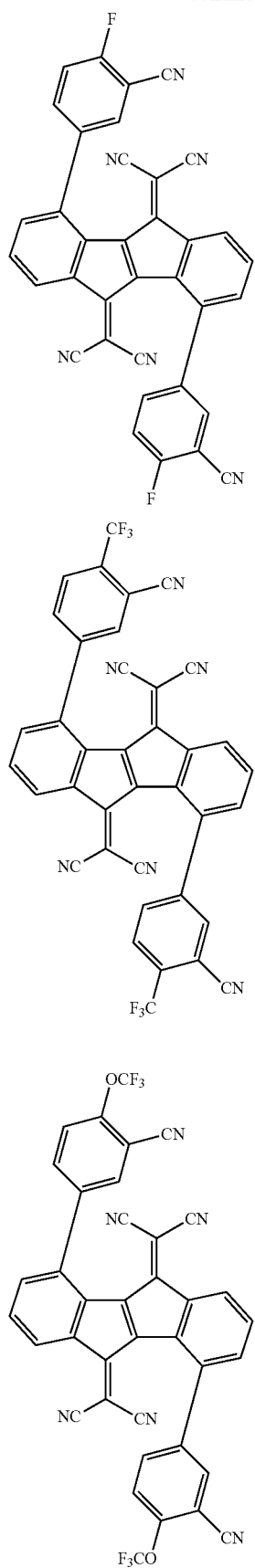
-continued
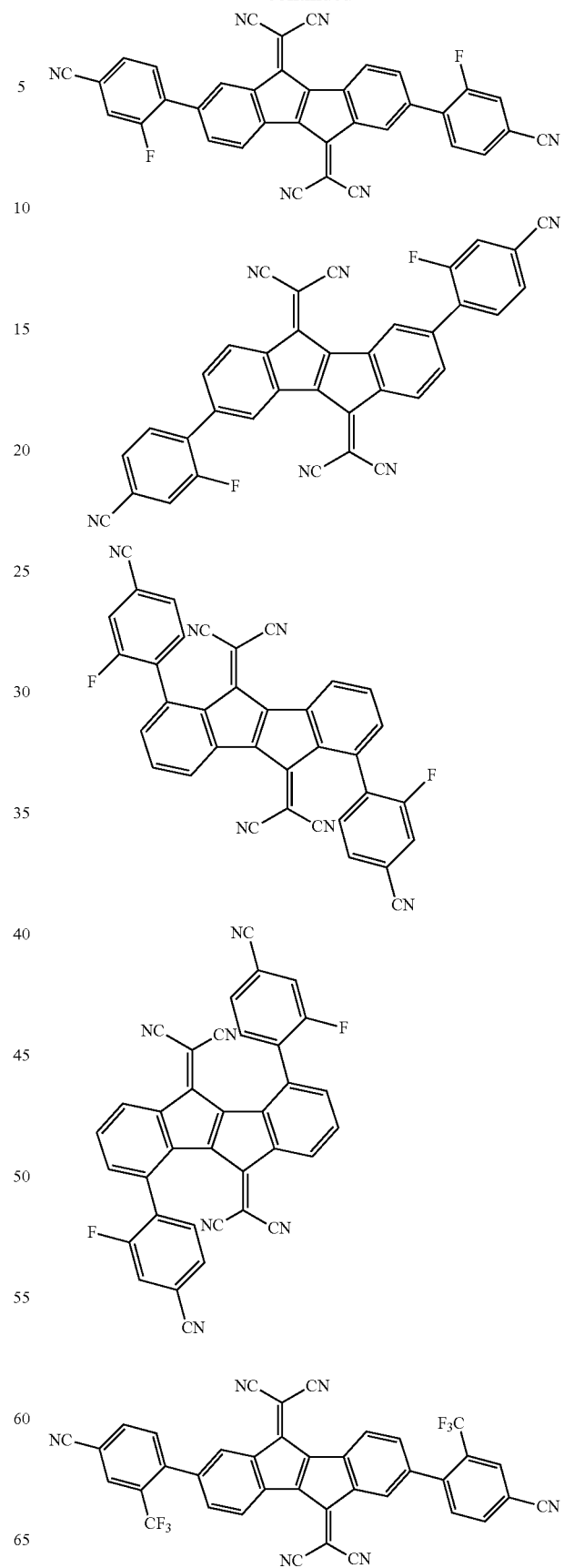

-continued
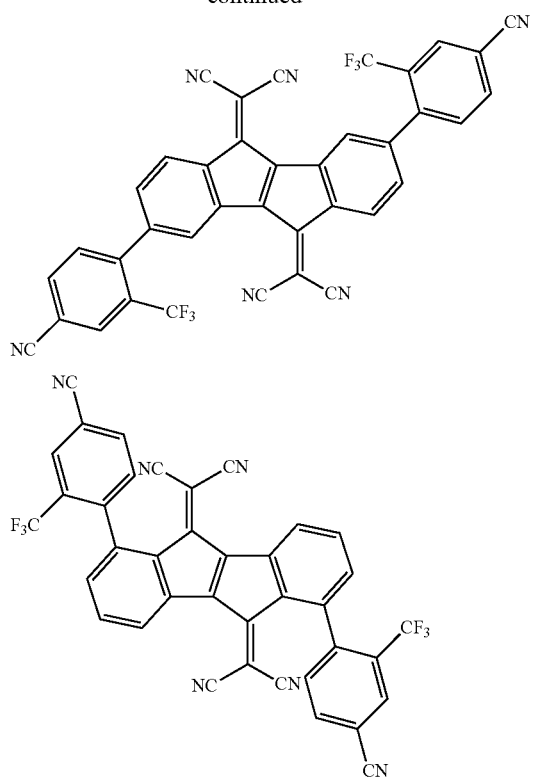
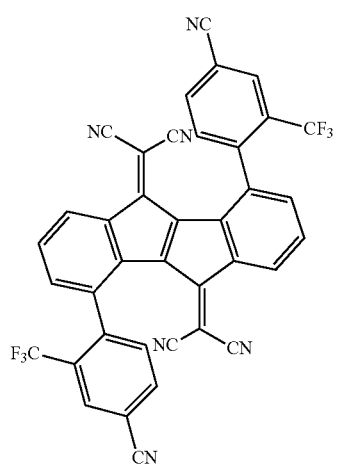
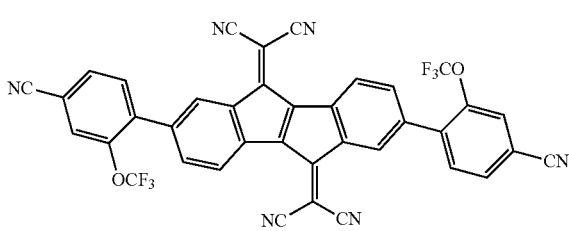
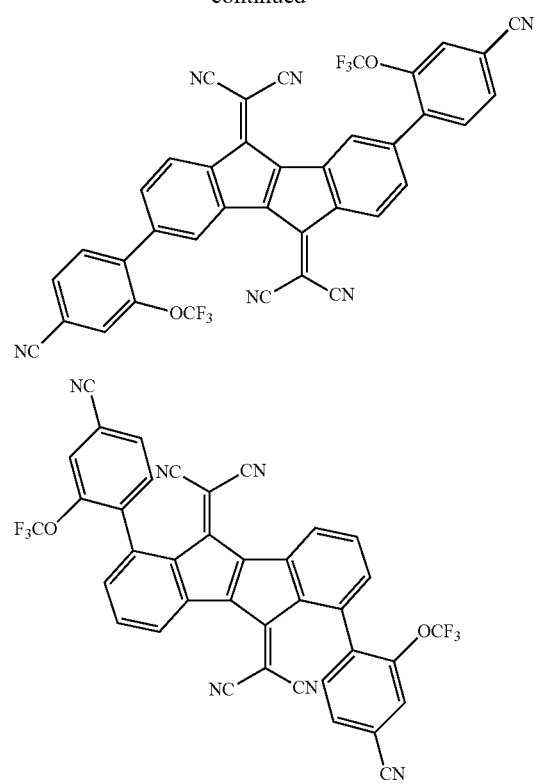
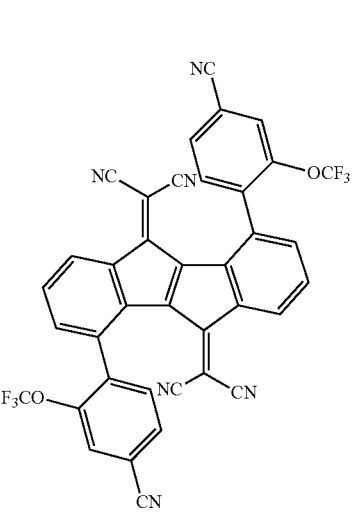
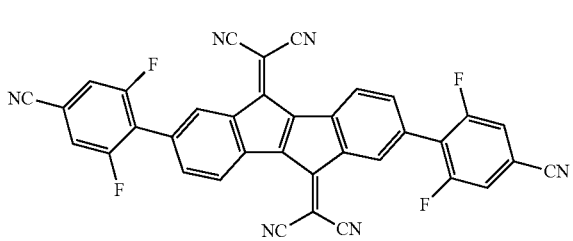

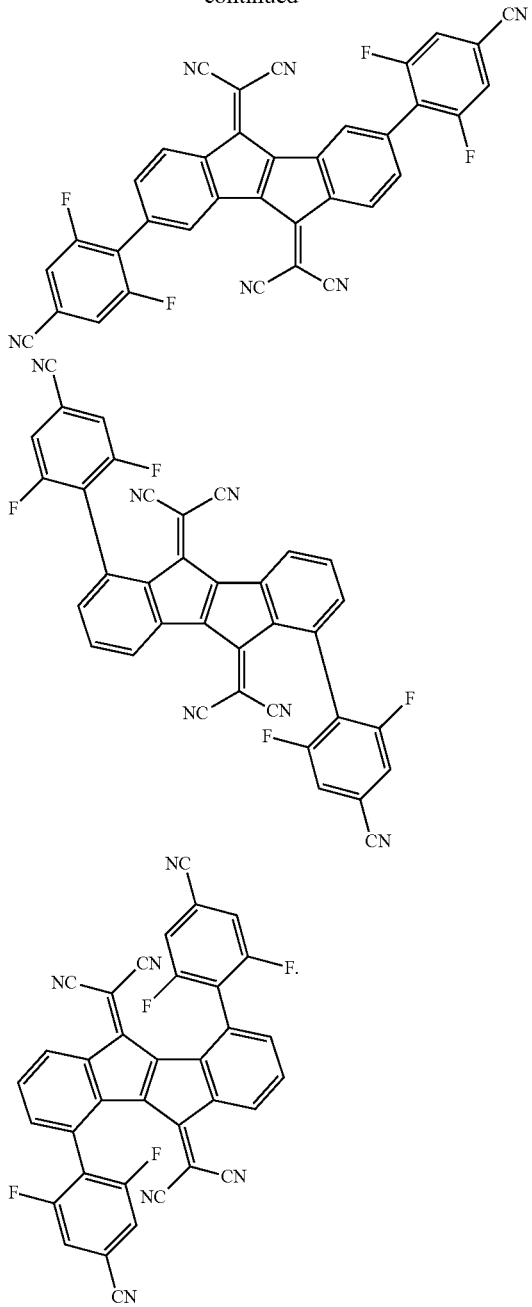

In addition, the present invention provides, as an example, a method for preparing a compound of Chemical Formula 1 as shown in the following Reaction Scheme 1.

Reaction Scheme 1

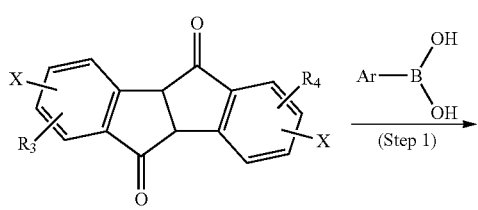

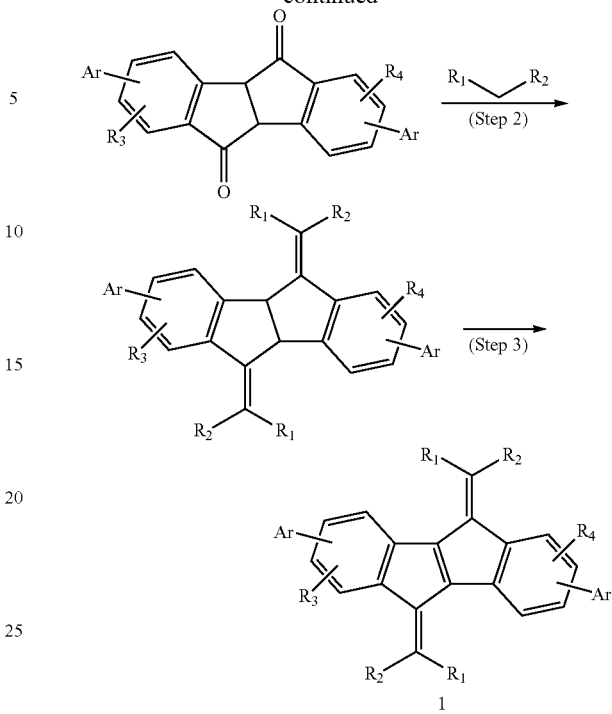

In Reaction Scheme 1, the remaining definitions excluding X are the same as defined above, and X is halogen and more preferably bromo or chloro.

Step 1 is a Suzuki coupling reaction, which is preferably carried out in the presence of a palladium catalyst and a base, and a reactive group for the Suzuki coupling reaction can be modified as known in the art. Step 2 is a Knoevenagel condensation reaction, which is preferably carried out in the presence of a base. Step 3 is a dehydrogenation reaction, which is preferably carried out in the presence of N-bromosuccinimide. The above preparation method will be more specifically described in the Preparation Examples described hereinafter.

In another embodiment of the invention, there is provided an organic light emitting device including a compound of Chemical Formula 1 described above. As an example, there is provided an organic light emitting device including a first electrode; a second electrode that is disposed opposite to the first electrode; and one or more organic material layers that are disposed between the first electrode and the second electrode, wherein one or more layers of the organic material layers include the compound of Chemical Formula 1.

The organic material layer of the organic light emitting device of the present invention can have a single-layer structure, or it can have a multilayered structure in which two or more organic material layers are stacked. For example, the organic light emitting device of the present invention can have a structure comprising a hole injection layer, a hole transport layer, a light emitting layer, an electron transport layer, an electron injection layer and the like as the organic material layer. However, the structure of the organic light emitting device is not limited thereto, and it can include a smaller number of organic layers.

Further, the organic material layer can include a hole injection layer, a hole transport layer, or a layer for simultaneously performing hole injection and transport, wherein the hole injection layer, the hole transport layer, or the layer for simultaneously performing hole injection and transport include the compound of Chemical Formula 1. For example, the organic material layer includes a hole injection layer, wherein the hole injection layer is formed of the compound alone or is formed by doping the compound. Further, the organic material layer can include a doped hole transport layer, wherein the doped hole transport layer is formed by doping the hole transport material with the compound.

Further, the organic material layer can include a light emitting layer, wherein the light emitting layer includes the compound of Chemical Formula 1. In particular, the compound according to the present invention can be used as a dopant of the light emitting layer.

Further, the organic material layer can include an electron transport layer, or an electron injection layer, wherein the electron transport layer, or the electron injection layer includes the compound of Chemical Formula 1.

Further, the electron transport layer, the electron injection layer, or the layer for simultaneously performing electron transport and electron injection include the compound of Chemical Formula 1.

Further, the organic material layer includes a light emitting layer and an electron transport layer, wherein the electron transport layer can include a compound of Chemical Formula 1.

Further, the organic light emitting device according to the present invention can be a normal type organic light emitting device in which an anode, one or more organic material layers and a cathode are sequentially stacked on a substrate. Further, the organic light emitting device according to the present invention can be an inverted type organic light emitting device in which a cathode, one or more organic material layers and an anode are sequentially stacked on a substrate. For example, the structure of an organic light emitting device according to an embodiment of the present invention is illustrated in FIGS. 1 to 3.

FIG. 1 shows an example of an organic light emitting device comprising a substrate 1, an anode 2, a light emitting layer 3, and a cathode 4. In such a structure, the compound of Chemical Formula 1 can be included in the light emitting layer.

FIG. 2 shows an example of an organic light emitting device comprising a substrate 1, an anode 2, a hole injection layer 5, a hole transport layer 6, a light emitting layer 7, an electron transport layer 8 and a cathode 4. In such a structure, the compound of Chemical Formula 1 can be included in one or more layers of the hole injection layer, the hole transport layer, the light emitting layer and the electron transport layer.

FIG. 3 shows an example of an organic light emitting device comprising a substrate 1, an anode 2, a hole injection layer 5, a hole transport layer 6, an electron blocking layer 9, a light emitting layer 7, an electron transport layer 8, an electron injection layer 10 and a cathode 4. In such a structure, the compound of Chemical Formula 1 can be included in one or more layers of the hole injection layer, the hole transport layer, the light emitting layer, the electron transport layer and the electron injection layer.

Further, a first stack emitting light of a first color, a second stack emitting light of a second color, and a charge generating layer that uniformly controls charges between the first stack and the second stack are formed between the first electrode and the second electrode, wherein the charge generating layer includes a N-type charge generating layer disposed adjacent to the first stack and a P-type charge generating layer disposed adjacent to the second stack, wherein the organic material layer constitutes the P-type charge generating layer, and wherein the P-type charge generating layer can be formed of the compound alone or can be formed by doping the compound.

Further, a first stack emitting light of a first color, a second stack emitting light of a second color, and a charge generating layer that uniformly controls charges between the first stack and the second stack are formed between the first electrode and the second electrode, wherein the charge generating layer includes a N-type charge generating layer disposed adjacent to the first stack and a P-type charge generating layer disposed adjacent to the second stack, wherein the organic material layer constitutes the P-type charge generating layer, and wherein the P-type charge generating layer can be formed by doping the hole transport material with the compound.

Figure 4:
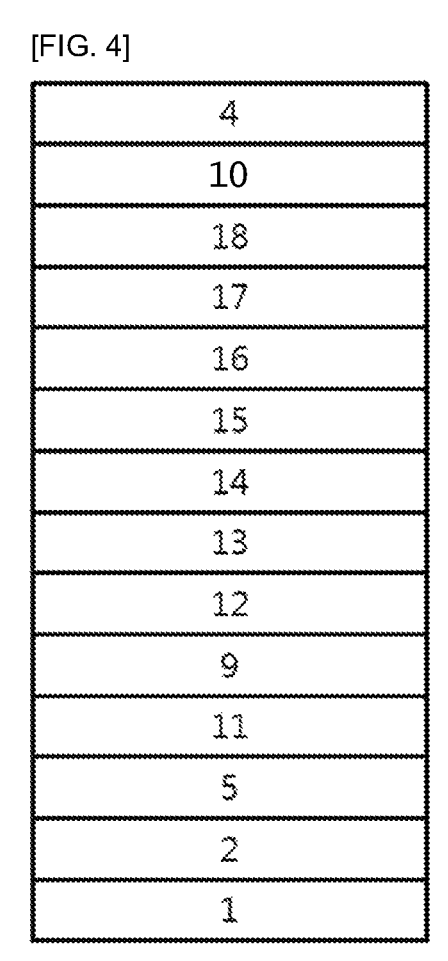

The above example is shown in FIG. 4. FIG. 4 shows an example of an organic light emitting device comprising a substrate 1, an anode 2, a hole injection layer 5, a first hole transport layer 11, an electron blocking layer 9, a first light emitting layer 12, a first electron transport layer 13, a N-type charge generating layer 14, a P-type charge generating layer 15, a second hole transport layer 16, a second light emitting layer 17, a second electron transport layer 18, an electron injection layer 10 and a cathode 4.

Further, the organic light emitting device can further include one layer or two or more layers selected from the group consisting of a hole injection layer, a hole transport layer, a light emitting layer, an electron transport layer, an electron injection layer, an electron blocking layer, and a hole blocking layer.

The organic light emitting device according to the present invention can be manufactured by materials and methods known in the art, except that one or more layers of the organic material layers include the compound of Chemical Formula 1. Moreover, when the organic light emitting device includes a plurality of organic material layers, the organic material layers can be formed of the same material or different materials.

For example, the organic light emitting device according to the present invention can be manufactured by sequentially stacking a first electrode, an organic material layer and a second electrode on a substrate. In this case, the organic light emitting device can be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer and the electron transport layer thereon, and then depositing a material that can be used as the cathode thereon. In addition to such a method, the organic light emitting device can be manufactured by sequentially depositing a cathode material, an organic material layer and an anode material on a substrate.

Further, the compound of Chemical Formula 1 can be formed into an organic layer by a solution coating method as well as a vacuum deposition method at the time of manufacturing an organic light emitting device. Herein, the solution coating method means a spin coating, a dip coating, a doctor blading, an inkjet printing, a screen printing, a spray method, a roll coating, or the like, but is not limited thereto.

In addition to such a method, the organic light emitting device can be manufactured by sequentially depositing a cathode material, an organic material layer and an anode material on a substrate (International Publication WO2003/012890). However, the manufacturing method is not limited thereto.

As an example, the first electrode is an anode, and the second electrode is a cathode, or alternatively, the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or SnO$_2$:Sb, conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or LiO$_2$/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole-injecting effect to the light emitting layer or the light emitting material, prevents excitons produced in the light emitting layer from moving to an electron injection layer or the electron injection material, and is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which can receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The light emitting material is preferably a material which can receive holes and electrons transported from a hole transport layer and an electron transport layer, respectively, and combine the holes and the electrons to emit light in a visible ray region, and has good quantum efficiency to fluorescence or phosphorescence. Specific examples thereof include an 8-hydroxy-quinoline aluminum complex (Alq$_3$), a carbazole-based compound; a dimerized styryl compound; BAlq; a 10-hydroxybenzoquinoline-metal compound; a benzoxazole, benzothiazole and benzimidazole-based compound; a poly(p-phenylene-vinylene)(PPV)-based polymer; a spiro compound; polyfluorene, rubrene, and the like, but are not limited thereto.

The light emitting layer can include a host material and a dopant material. The host material can be a fused aromatic ring derivative, a heterocyclic-containing compound or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto.

The dopant material can be an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene and the like, which have an arylamino group. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

The electron transport layer is a layer which receives electrons from an electron injection layer and transports the electrons to a light emitting layer, and an electron transport material is suitably a material which can receive electrons well from a cathode and transfer the electrons to a light emitting layer and has large mobility for electrons. Specific examples thereof include: an Al complex of 8-hydroxyquinoline; a complex including Alq$_3$; an organic radical compound; a hydroxyflavone-metal complex, and the like, but are not limited thereto. The electron transport layer can be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylene-tetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8- quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present invention can be a front side emission type, a backside emission type, or a double-sided emission type according to the used material.

In addition, the compound of Chemical Formula 1 can be included in an organic solar cell or an organic transistor in addition to an organic light emitting device.

EXAMPLE

Example 1

Preparation of Compound

Step 1) Preparation of Compound 1-1

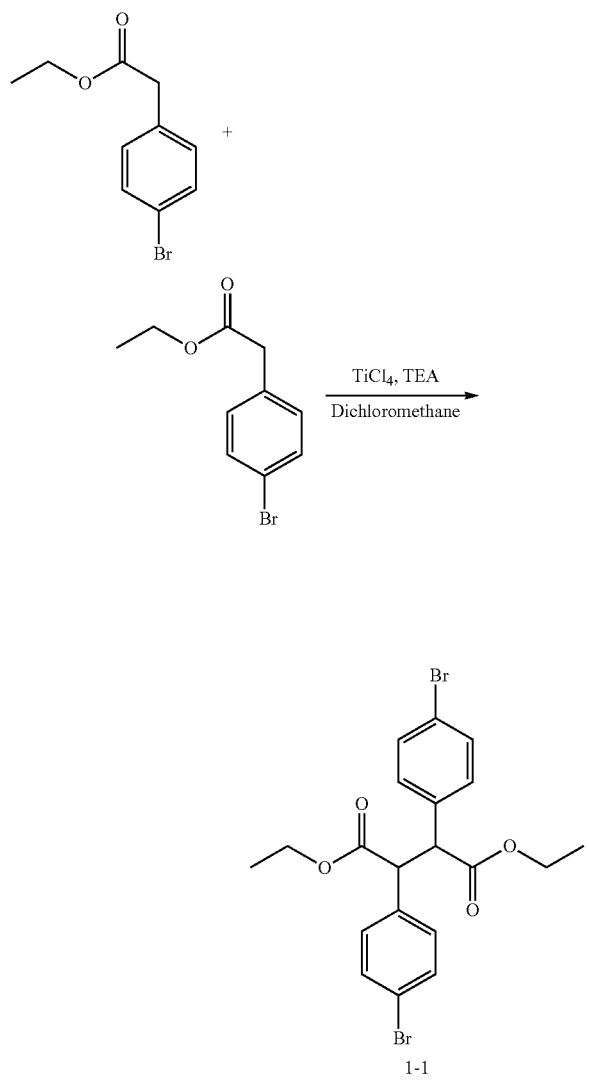

Ethyl 2-(4-bromophenyl)acetate (30.00 g, 12.34 mmol) was completely dissolved in dichloromethane (40 mL) in a 500 mL round bottom flask, and then cooled to 0° C. and stirred. After stirring for 10 minutes, titanium chloride(IV) (33.8 mL, 30.85 mmol) was slowly added dropwise. After stirring for about 30 minutes, triethylamine (43 mL, 30.85 mmol) was slowly added dropwise thereto. After completion of the reaction, an aqueous ammonium chloride solution was added thereto and then stirred for about 15 minutes. The temperature was raised to room temperature, the organic layer was extracted, dehydrated with anhydrous magnesium sulfate, filtered and then concentrated under reduced pressure. A small amount of anhydrous ethanol was added to the concentrate, stirred for 10 minutes, and then filtered to give Compound 1-1 (29.00 g, yield: 90.00%).

MS:$[M+H]^+$=484

Step 2) Preparation of Compound 1-2

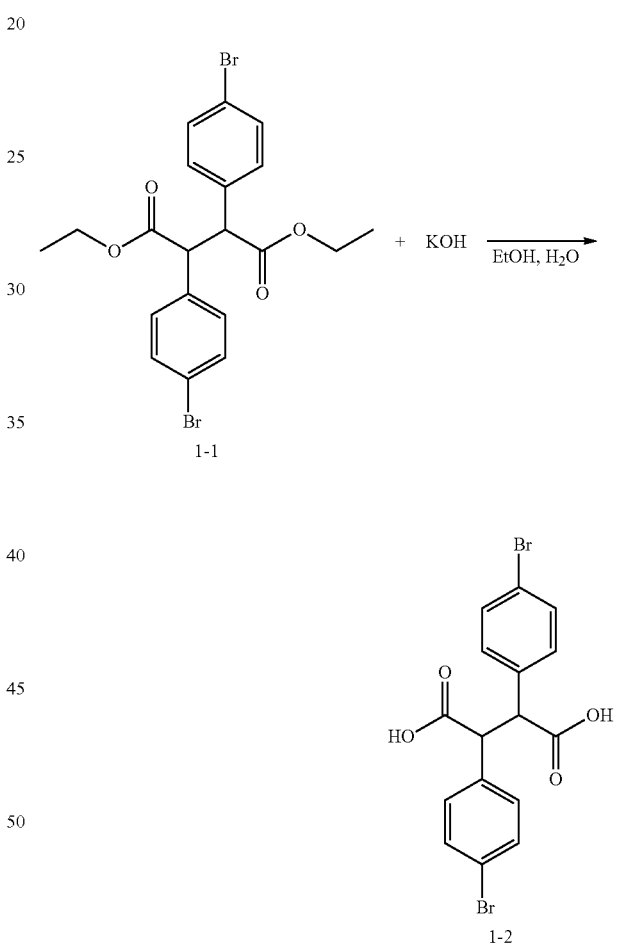

Compound 1-1 (29 g, 5.989 mmol), potassium hydroxide (16.8 g, 29.94 mmol) and a (1:1) mixed solution of anhydrous ethanol and water (580 mL) were added to a 1000 mL round bottom flask at room temperature and the mixture was stirred at 80° C. for 4 hours. After completion of the reaction, the reaction mixture was cooled to 0° C. and neutralized with HCl, which was then filtered. The resulting solid was washed with excess water to give Compound 1-2 (24.4 g, yield: 99%).

MS:$[M+H]^+$=428

Step 3) Preparation of Compound 1-3

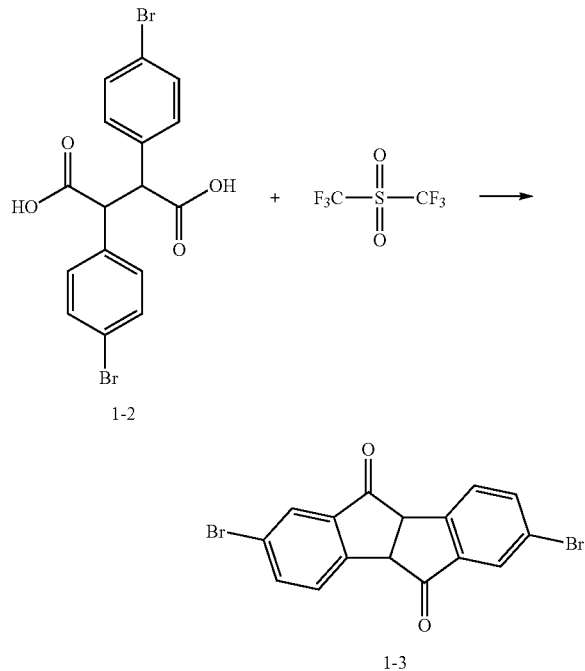

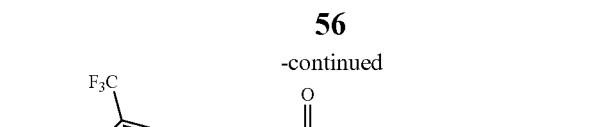

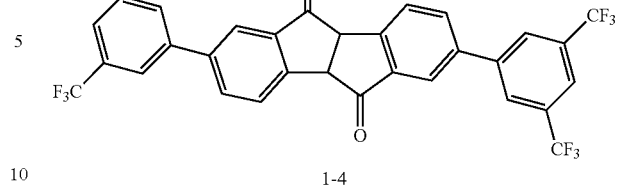

Compound 1-2 (24.00 g, 5.606 mmol) was heated and stirred together with triflic acid (168 g, 112.12 mmol) in a 1000 mL round bottom flask at 90° C. for 14 hours. After completion of the reaction, the reaction mixture was cooled to 0° C., and water (336 mL) was slowly added dropwise. The resulting solid was filtered, diluted with chloroform, dehydrated with anhydrous magnesium sulfate, filtered and then concentrated under reduced pressure. The concentrate was precipitated with anhydrous ethanol to give Compound 1-3 (13.2 g, yield: 60.00%).

MS:[M+H]$^+$=392

Step 4) Preparation of Compound 1-4

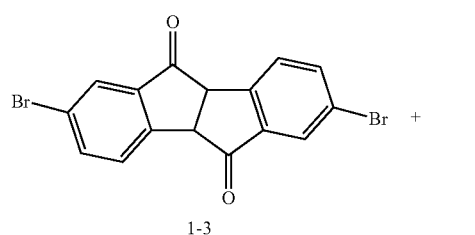

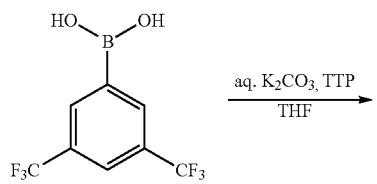

Compound 1-3 (10 g, 2.55 mmol), (3,5-bis (trifluoromethyl)phenyl)boronic acid (13.8 g, 5.356 mmol), tetrakis (triphenylphosphine)palladium(0) (0.3 g, 0.0255 mmol) and 25% aqueous potassium carbonate solution (1.05 g, 7.65 mmol) were completely dissolved in tetrahydrofuran (130 mL) in a 500 mL round bottom flask, and then heated and stirred. After completion of the reaction, the reaction mixture was cooled to room temperature, filtered, and the organic solvent layers were collected and concentrated under reduced pressure. The concentrate was precipitated with anhydrous ethanol to give Compound 1-4 (10 g, yield: 60.00%).

MS:[M+H]$^+$=658

Step 5) Preparation of Compound 1-5

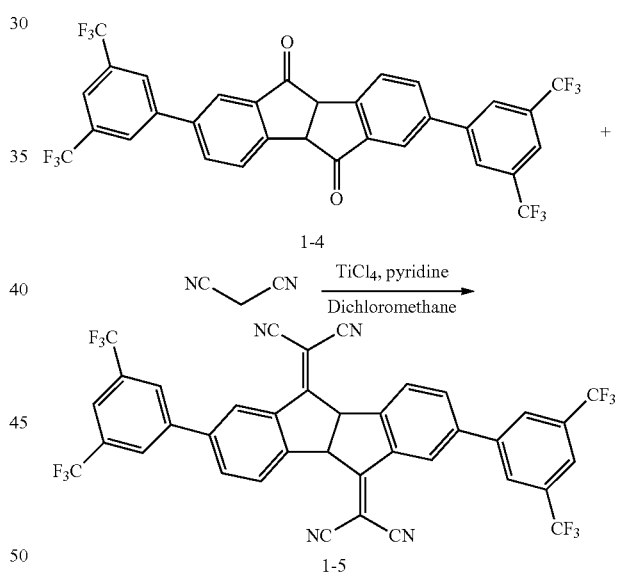

Compound 1-4 (5.00 g, 0.759 mmol) was completely dissolved in dichloromethane (150 mL) in a 250 mL round bottom flask, and then stirred at room temperature. Malononitrile (3 g, 4.556 mmol) was added to the reaction solution and then stirred at 0° C. for 10 minutes. Then, titanium chloride(IV) and pyridine were added, and stirred at room temperature for 1 hour. After completion of the reaction, water was added, the mixture was stirred for 10 minutes, then the organic layers were collected, dehydrated with anhydrous magnesium sulfate, filtered, and concentrated under reduced pressure. The concentrate was precipitated with methyl tert-butyl ester to give Compound 1-5 (3 g, yield: 52.00%).

MS:[M+H]$^+$=754

Step 6) Preparation of Compound 1

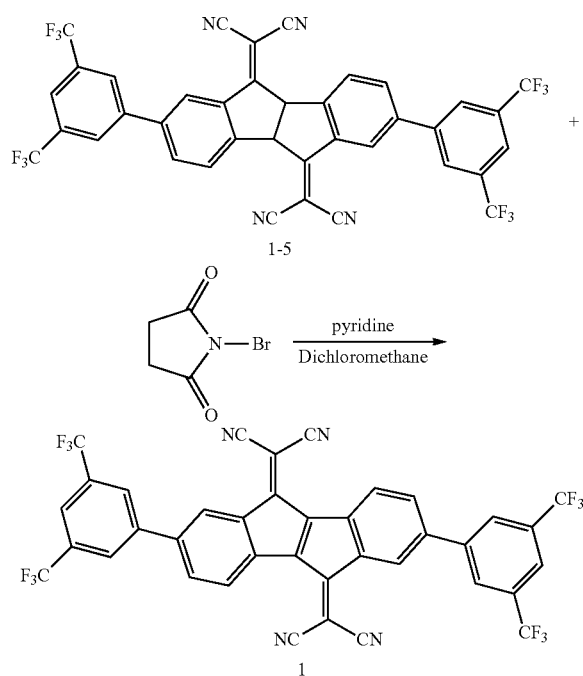

Compound 1-5 (3.00 g, 0.397 mmol) was completely dissolved in dichloromethane (90 mL) in a 250 mL round bottom flask, and then stirred at room temperature. 1-Bromo-2,5-pyrrolidinedione (1.77 g, 0.994 mmol) was added to the reaction solution and then stirred for 1 hour. After completion of the reaction, the reaction mixture was filtered and washed with water and methyl tert-butyl ester to give Compound 1 (2.8 g, yield: 99%).

MS:[M+H]$^+$=752

Example 2

Preparation of Compound 2

Step 1) Preparation of Compound 2-1

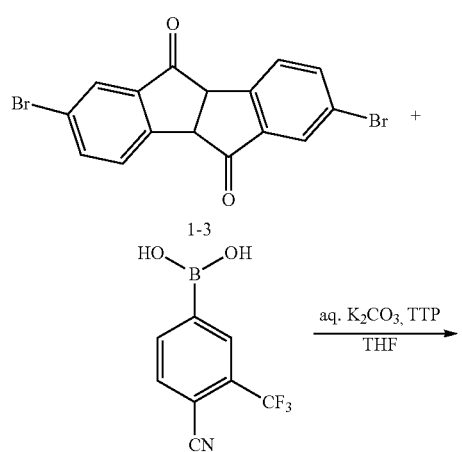

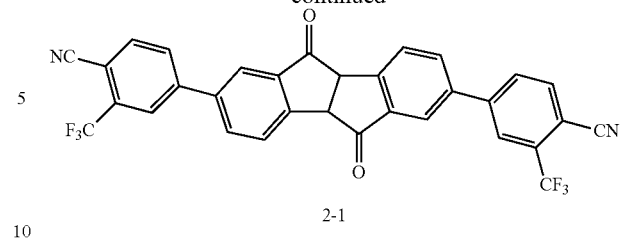

Compound 1-3 (10 g, 2.55 mmol), (4-cyano-3-(trifluoromethyl)phenyl)boronic acid (11.5 g, 5.355 mmol), tetrakis(triphenylphosphine)palladium(0) (0.3 g, 0.0255 mmol) and 25% aqueous potassium carbonate solution (1.05 g, 7.65 mmol) were completely dissolved in tetrahydrofuran (130 mL) in a 500 mL round bottom flask, and then heated and stirred. After completion of the reaction, the reaction mixture was cooled to room temperature, filtered, and the organic solvent layers were collected and concentrated under reduced pressure. The concentrate was precipitated with anhydrous ethanol to give Compound 2-1 (9 g, yield: 61.60%).

MS:[M+H]$^+$=572

Step 2) Preparation of Compound 2

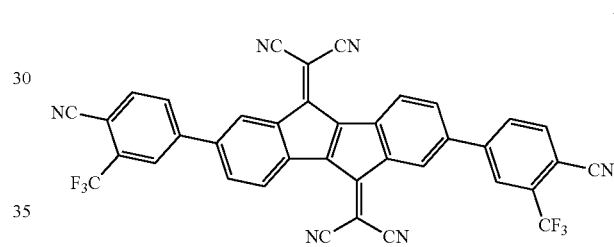

Compound 2 (2 g, yield: 96%) was prepared in the same manner as in steps 5 and 6 of Example 1, except that Compound 2-1 prepared above was used instead of Compound 1-4.

MS:[M+H]$^+$=666

Example 3

Preparation of Compound 3

Step 1) Preparation of Compound 3-1

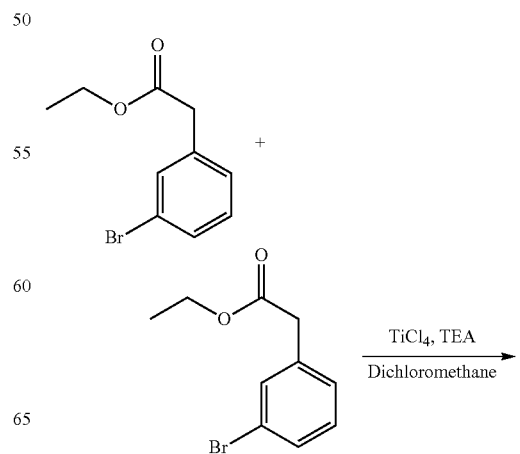

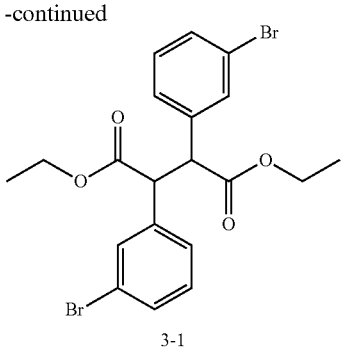

3-1

Ethyl 2-(3-bromophenyl)acetate (30.00 g, 12.34 mmol) was completely dissolved in dichloromethane (40 mL) in a 500 mL round bottom flask, and then cooled to 0° C. and stirred. After stirring for 10 minutes, titanium chloride(IV) (33.8 mL, 30.85 mmol) was slowly added dropwise thereto. After stirring for about 30 minutes, triethylamine (43 mL, 30.85 mmol) was slowly added dropwise. After completion of the reaction, an aqueous ammonium chloride solution was added thereto and then stirred for about 15 minutes. The temperature was raised to room temperature, the organic layer was extracted, dehydrated with anhydrous magnesium sulfate, filtered and then concentrated under reduced pressure. A small amount of anhydrous ethanol was added to the concentrate, stirred for 10 minutes, and then filtered to give Compound 3-1 (29.00 g, yield: 90.00%).

MS:[M+H]⁺=484

Step 2) Preparation of Compound 3-2

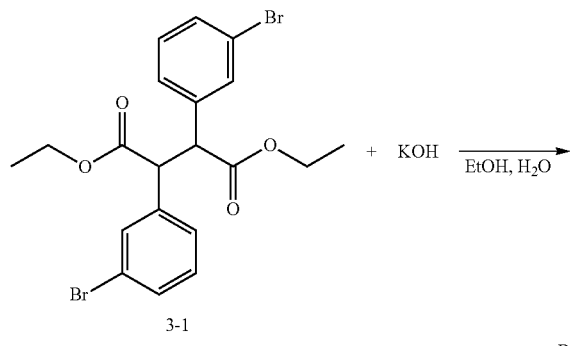

Compound 3-1 (29 g, 5.989 mmol), potassium hydroxide (16.8 g, 29.94 mmol) and a (1:1) mixed solution of anhydrous ethanol and water (580 mL) were added to a 1000 mL round bottom flask at room temperature and the mixture was stirred at 80° C. for 4 hours. After completion of the reaction, the reaction mixture was cooled to 0° C. and neutralized with HCl, which was then filtered. The resulting solid was washed with excess water to give Compound 3-2 (24.4 g, yield: 99%).

MS:[M+H]⁺=428

Step 3) Preparation of Compound 3-3

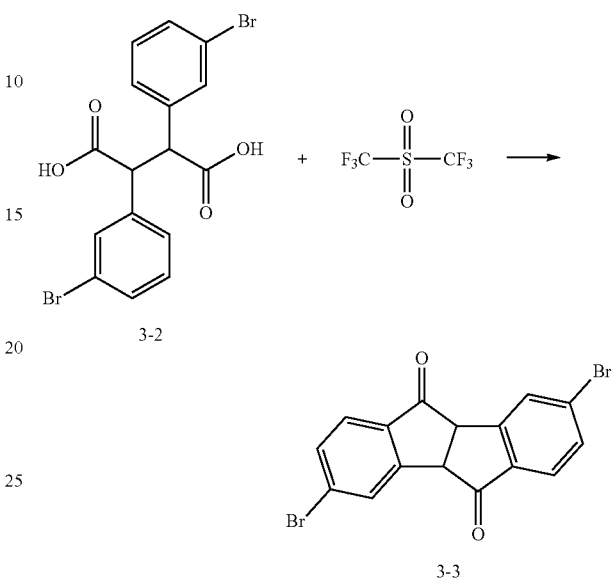

Compound 3-2 (24.00 g, 5.606 mmol) was heated and stirred together with triflic acid (168 g, 112.12 mmol) in a 1000 mL round bottom flask at 90° C. for 14 hours. After completion of the reaction, the reaction mixture was cooled to 0° C., and water (336 mL) was slowly added dropwise. The resulting solid was filtered, diluted with chloroform, dehydrated with anhydrous magnesium sulfate, filtered and then concentrated under reduced pressure. The concentrate was precipitated with anhydrous ethanol to give Compound 3-3 (13.2 g, yield: 60.00%).

MS: [M+H]⁺=392

Step 4) Preparation of Compound 3

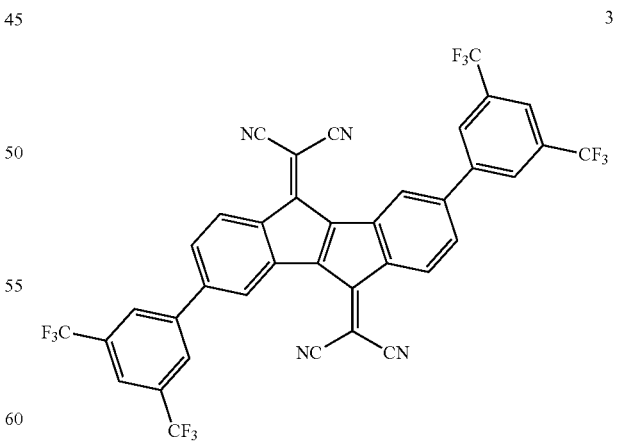

Compound 3 (2.5 g, yield: 99%) was prepared in the same manner as in steps 4 to 6 of Example 1, except that Compound 3-3 prepared above was used instead of Compound 1-3.

MS:[M+H]⁺=752

Example 4

Preparation of Compound 4

Step 1) Preparation of Compound 4-1

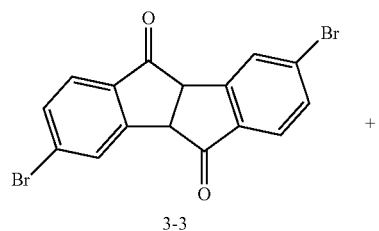

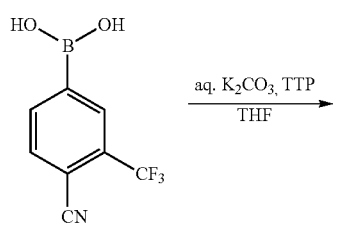

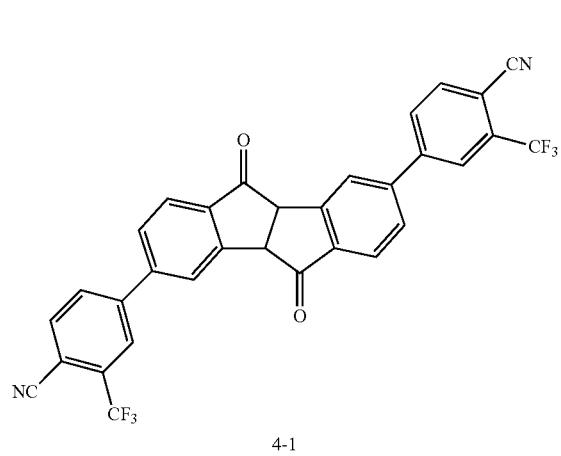

Compound 3-3 (10 g, 2.55 mmol), (4-cyano-3-(trifluoromethyl)phenyl)boronic acid (11.5 g, 5.355 mmol), tetrakis(triphenylphosphine)palladium(0) (0.3 g, 0.0255 mmol) and 25% aqueous potassium carbonate solution (1.05 g, 7.65 mmol) were completely dissolved in tetrahydrofuran (130 mL) in a 500 mL round bottom flask, and then heated and stirred. After completion of the reaction, the reaction mixture was cooled to room temperature, filtered, and the organic solvent layers were collected and concentrated under reduced pressure. The concentrate was precipitated with anhydrous ethanol to give Compound 4-1 (11 g, yield: 75.3%).

MS:[M+H]$^+$=572

Step 2) Preparation of Compound 4

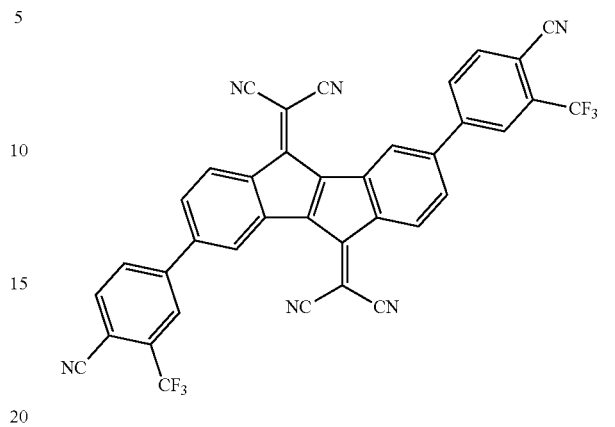

Compound 4 (3 g, yield: 96%) was prepared in the same manner as in steps 5 and 6 of Example 1, except that Compound 4-1 prepared above was used instead of Compound 1-4.

MS:[M+H]$^+$=666

Example 5

Preparation of Compound 5

Step 1) Preparation of Compound 5-1

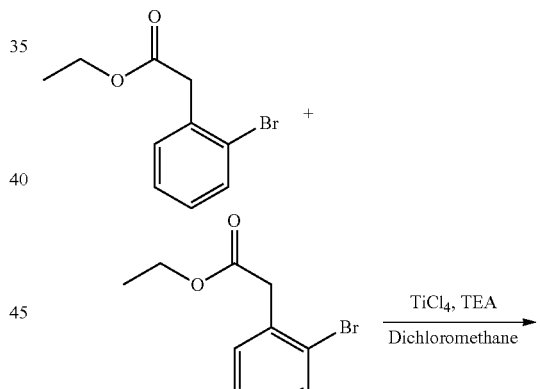

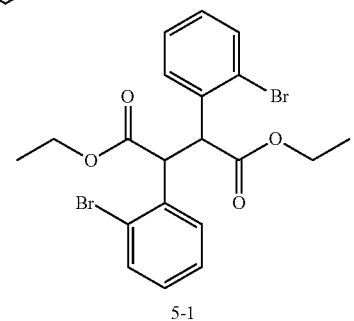

Ethyl 2-(2-bromophenyl)acetate (30.00 g, 12.34 mmol) was completely dissolved in dichloromethane (40 mL) in a 500 mL round bottom flask, and then cooled to 0° C. and stirred. After stirring for 10 minutes, titanium chloride(IV) (33.8 mL, 30.85 mmol) was slowly added dropwise thereto.

After stirring for about 30 minutes, triethylamine (43 mL, 30.85 mmol) was slowly added dropwise. After completion of the reaction, an aqueous ammonium chloride solution was added thereto and then stirred for about 15 minutes. The temperature was raised to room temperature, the organic layer was extracted, dehydrated with anhydrous magnesium sulfate, filtered and then concentrated under reduced pressure. A small amount of anhydrous ethanol was added to the concentrate, stirred for 10 minutes, and then filtered to give Compound 5-1 (20.00 g, yield: 60.00%).

MS:[M+H]$^+$=484

Step 2) Preparation of Compound 5-2

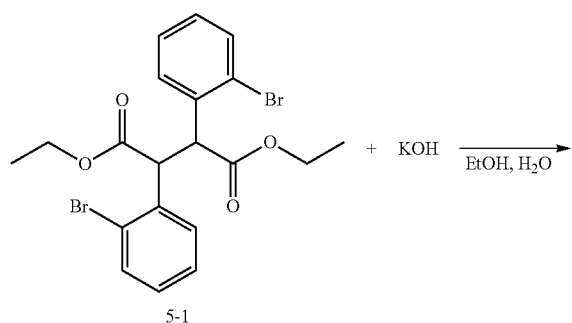

Compound 5-1 (20 g, 4.130 mmol), potassium hydroxide (11.59 g, 20.65 mmol) and a (1:1) mixed solution of anhydrous ethanol and water (580 mL) were added to a 1000 mL round bottom flask at room temperature and the mixture was stirred at 80° C. for 4 hours. After completion of the reaction, the mixture was cooled to 0° C. and neutralized with HCl, which was then filtered. The resulting solid was washed with excess water to give Compound 5-2 (17.0 g, yield: 91%).

MS:[M+H]$^+$=428

Step 3) Preparation of Compound 5-3

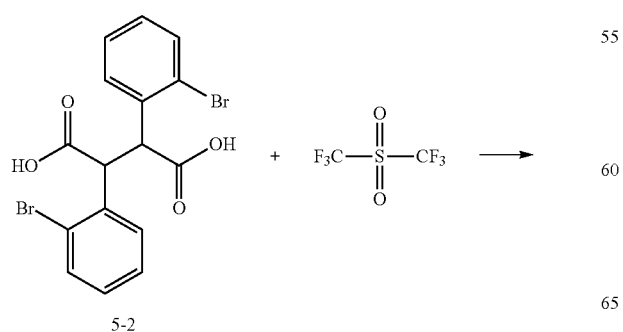

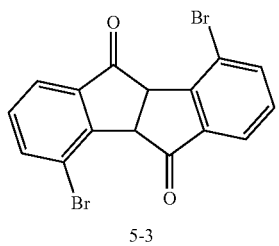

Compound 5-2 (17.00 g, 3.971 mmol) was heated and stirred together with triflic acid (119 g, 79.29 mmol) in a 1000 mL round bottom flask at 90° C. for 14 hours. After completion of the reaction, the reaction mixture was cooled to 0° C., and water (336 mL) was slowly added dropwise. The resulting solid was filtered, diluted with chloroform and dehydrated with anhydrous magnesium sulfate, filtered and then concentrated under reduced pressure. The concentrate was precipitated with anhydrous ethanol to give Compound 5-3 (10 g, yield: 64.00%).

MS: [M+H]$^+$=392

Step 4) Preparation of Compound 5

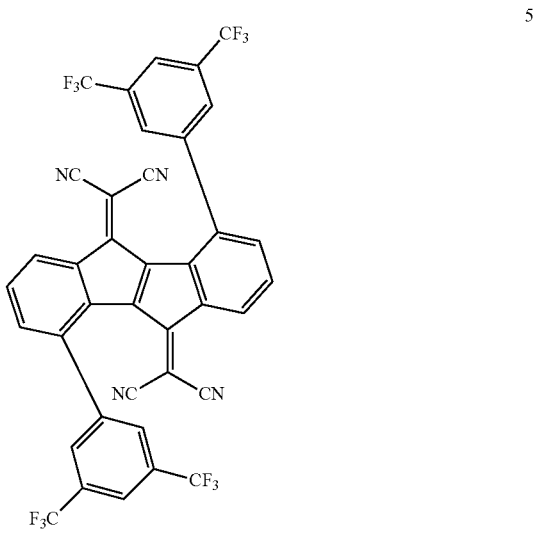 [SMILES: N#CC(C#N)=C1C2=C(C(=C(C#N)C#N)c3cccc(-c4cc(C(F)(F)F)cc(C(F)(F)F)c4)c32)c2c1cccc2-c1cc(C(F)(F)F)cc(C(F)(F)F)c1]

Compound 5 (2.6 g, yield: 99%) was prepared in the same manner as in steps 4 to 6 of Example 1, except that Compound 5-3 prepared above was used instead of Compound 1-3.

MS:[M+H]$^+$=752

Example 6

Preparation of Compound 6

Step 1) Preparation of Compound 6-1

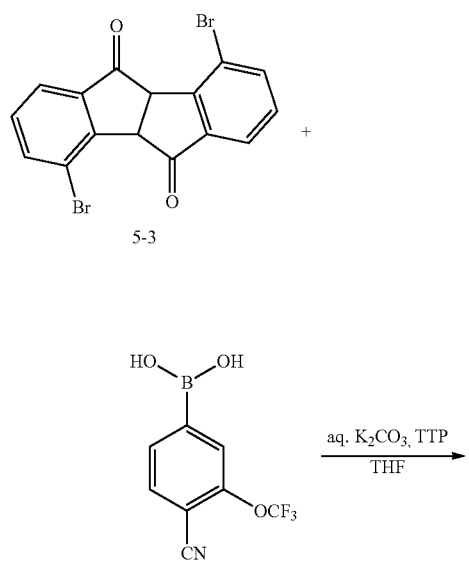

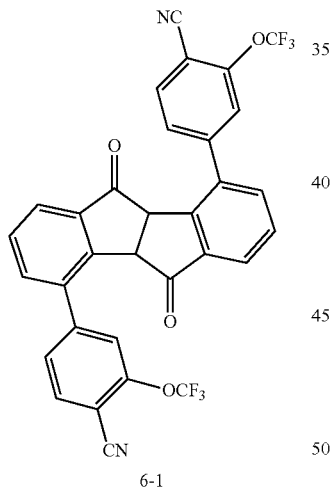

Compound 5-3 (10 g, 2.55 mmol), (4-cyano-3-(trifluoromethoxy)phenyl)boronic acid (12.37 g, 5.357 mmol), tetrakis(triphenylphosphine)palladium(0) (0.3 g, 0.0255 mmol) and 25% aqueous potassium carbonate solution (1.05 g, 7.65 mmol) were completely dissolved in tetrahydrofuran (130 mL) in a 500 mL round bottom flask, and then heated and stirred. After completion of the reaction, the reaction mixture was cooled to room temperature, filtered, and the organic solvent layers were collected and concentrated under reduced pressure. The concentrate was precipitated with anhydrous ethanol to give Compound 6-1 (7 g, yield: 45.4%).

MS:[M+H]$^+$=604

Step 2) Preparation of Compound 6

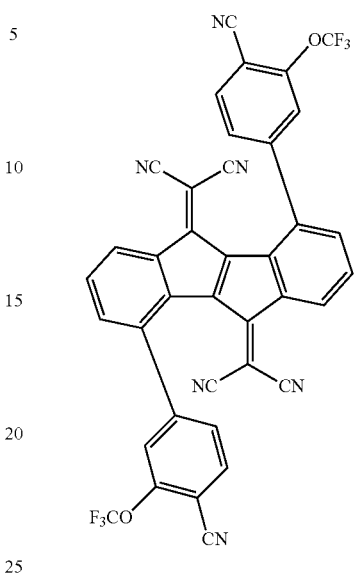

Compound 6 (2.2 g, yield: 95%) was prepared in the same manner as in steps 5 and 6 of Example 1, except that Compound 6-1 prepared above was used instead of Compound 1-4.

MS:[M+H]$^+$=698

EXPERIMENTAL EXAMPLE

Experimental Example 1-1

A glass substrate on which ITO (indium tin oxide) was coated as a thin film to a thickness of 1,400 Å was put into distilled water in which a detergent was dissolved, and ultrasonically cleaned. A Decon™ CON705 product available at Fischer Co. was used as the detergent, and as the distilled water, distilled water filtered twice using a 0.22 um sterilizing filter manufactured by Millipore Co. was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone and methanol for 10 minutes, respectively, dried, and then transferred to a plasma cleaner. The substrate was cleaned for 5 minutes using oxygen plasma and then transferred to a vacuum depositor.

On the ITO transparent electrode thus prepared, the compound HT-A shown below and the compound 1 prepared in the previous Example were thermally vacuum-deposited at a weight ratio of 95:5 to a thickness of 100 Å to form a hole injection layer. Only the compound HT-A shown below was deposited in a thickness of 1100 Å on the hole injection layer to form a hole transport layer. The compound EB-A shown below was thermally vacuum-deposited in a thickness of 50 Å on the hole transport layer to form an electron blocking layer. The compound BH-A shown below and the compound BD-A shown below were vacuum-deposited at a weight ratio of 96:4 to a thickness of 200 Å on the electron blocking layer to form a light emitting layer. The compound ET-A shown below and the compound Liq shown below were thermally vacuum-deposited at a weight ratio of 1:1 to a thickness of 360 Å on the light emitting layer to form an electron transport layer. The compound Liq shown below was vacuum-deposited in a thickness of 5 Å on the electron transport layer to form an electron injection layer. Magnesium and silver (mixed in a weight ratio of 10:1) in a thickness of 220 Å and aluminum in a thickness of 1000 Å was sequentially deposited on the electron injection layer to form a cathode, thereby completing the manufacture of an organic light emitting device.

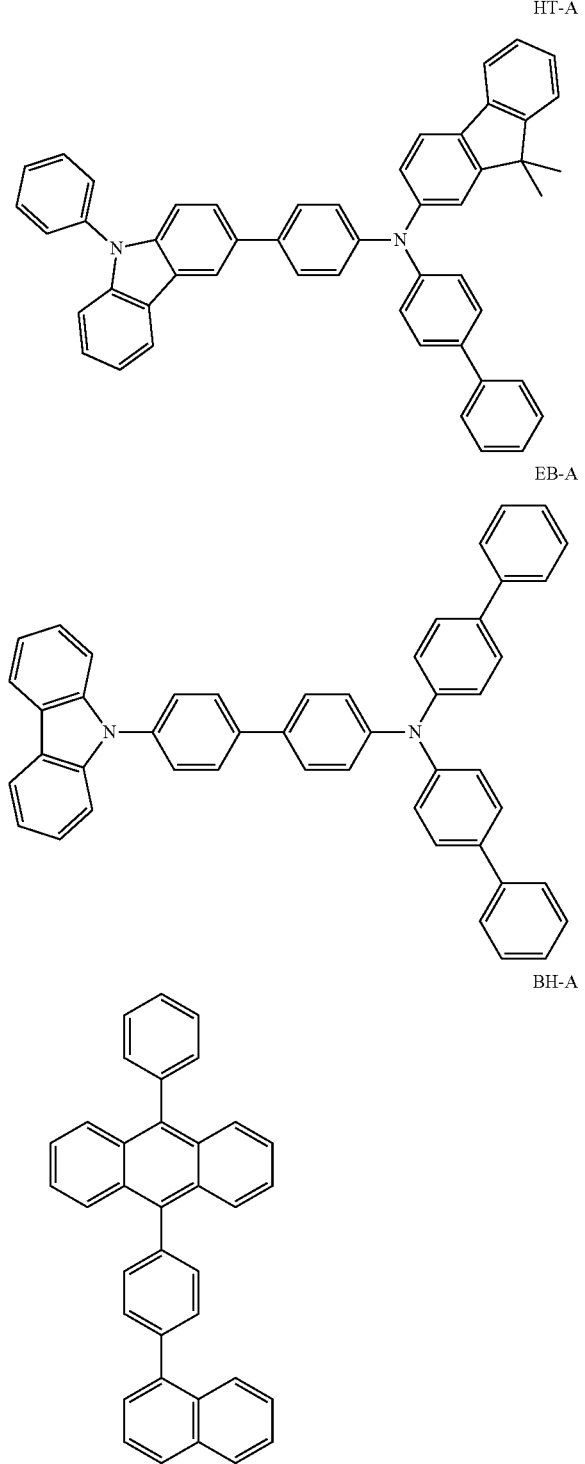

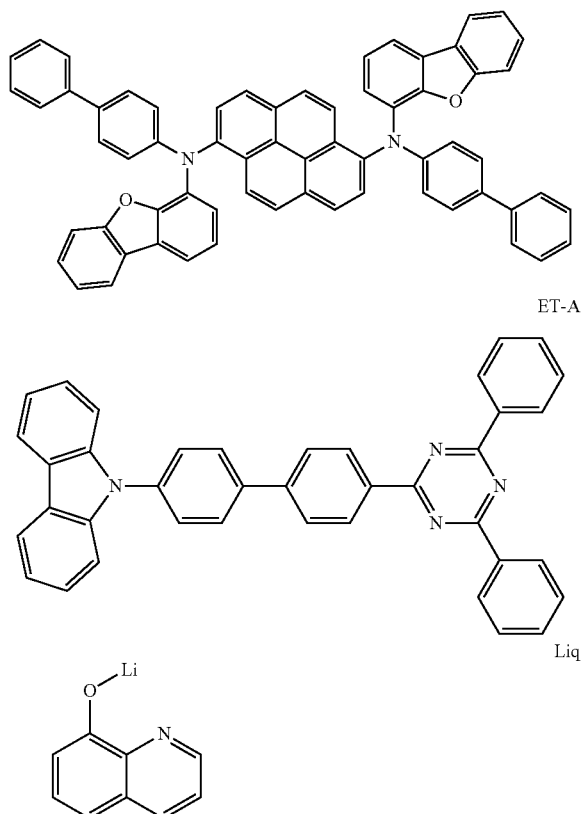

Experimental Examples 1-2 to 1-6

The organic light emitting devices were manufactured in the same manner as in Experimental Example 1-1, except that the compounds shown in Table 1 below were used instead of Compound 1-1 in Experimental Example 1-1.

Comparative Experimental Example 1-1

An organic light emitting device was manufactured in the same manner as in Experimental Example 1-1, except that only a compound HAT-CN shown below was used as the hole injection layer in Experimental Example 1-1.

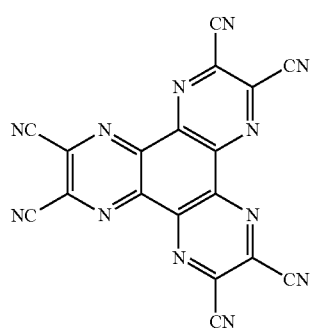

Comparative Experimental Example 1-2

An organic light emitting device was manufactured in the same manner as in Experimental Example 1-1, except that a hole injection layer was formed without any doping instead of Compound 1 in Experimental Example 1-1.

Comparative Experimental Example 1-3

An organic light emitting device was manufactured in the same manner as in Experimental Example 1-1, except that a compound A shown below was used instead of Compound 1 in Experimental Example 1-1.

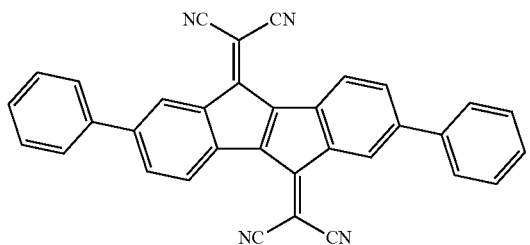

A

Comparative Experimental Example 1-4

An organic light emitting device was manufactured in the same manner as in Experimental Example 1-1, except that a compound B shown below was used instead of Compound 1 in Experimental Example 1-1.

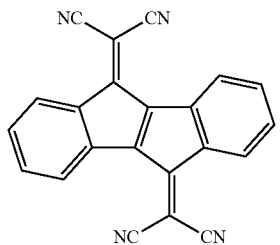

B

The driving voltages and efficiencies of the organic light emitting devices manufactured in Experimental Examples 1-1 to 1-6 and Comparative Experimental Examples 1-1 to 1-4 are shown in Table 1 below. At this time, the driving voltage and efficiency were measured by applying a current density of 10 mA/cm$^2$.

TABLE 1

|  | Hole injection layer Doping material | Voltage (V) | Efficiency (cd/A) |
|---|---|---|---|
| Experimental Example 1-1 | Compound 1 | 4.24 | 6.41 |
| Experimental Example 1-2 | Compound 2 | 4.22 | 6.49 |
| Experimental Example 1-3 | Compound 3 | 4.25 | 6.42 |
| Experimental Example 1-4 | Compound 4 | 4.23 | 6.49 |
| Experimental Example 1-5 | Compound 5 | 4.25 | 6.47 |
| Experimental Example 1-6 | Compound 6 | 4.22 | 6.46 |
| Comparative Experimental Example 1-1 | HAT-CN | 4.73 | 4.88 |
| Comparative Experimental Example 1-2 | — | 7.52 | 2.13 |
| Comparative Experimental Example 1-3 | Compound A | 5.45 | 3.62 |
| Comparative Experimental Example 1-4 | Compound B | 8.27 | 1.88 |

Experimental Example 2-1

A glass substrate on which ITO (indium tin oxide) was coated as a thin film to a thickness of 1,000 Å was put into distilled water in which a detergent was dissolved, and ultrasonically cleaned. A product manufactured by Fischer Co. was used as the detergent, and as the distilled water, distilled water filtered twice using a filter manufactured by Millipore Co. was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, dried, and then transferred to a plasma cleaner. The substrate was cleaned for 5 minutes using oxygen plasma and then transferred to a vacuum depositor.

On the ITO transparent electrode thus prepared, the compound HAT-CN shown below was thermally vacuum-deposited in a thickness of 50 Å to form a hole injection layer. The compound NPB shown below was vacuum-deposited in a thickness of 100 Å on the hole injection layer to form a first hole transport layer. The compound EB-B shown below was vacuum-deposited in a thickness of 100 Å on the first hole transport layer to form the first electron blocking layer. The compound YGH-A shown below, the compound YGH-B shown below, and the compound YGD shown below were vacuum-deposited at a weight ratio of 2:2:1 to a thickness of 400 Å on the first electron blocking layer to form a first light emitting layer. The compound ET-B shown below was vacuum-deposited in a thickness of 250 Å on the first light emitting layer to form a first electron transport layer. The compound NCG shown below and Li (lithium) were vacuum-deposited at a weight ratio of 50:1 to a thickness of 100 Å on the first electron transport layer to form a N-type charge generating layer. The compound HT-A shown below was formed in a thickness of 100 Å on the N-type charge generating layer, in which Compound 1 was doped at a doping concentration of 30 wt % to form a P-type charge generating layer. Only the compound HT-A shown below was vacuum-deposited in a thickness of 800 Å on the P-type charge generating layer to form a second hole transport layer. The compound BH-B shown below and the compound BD-B shown below were vacuum-deposited at a weight ratio of 96:4 to a thickness of 250 Å on the second hole transport layer to form a second light emitting layer. The compound ET-A shown below and a compound Liq shown below were thermally vacuum-deposited at a weight ratio of 1:1 to a thickness of 300 Å on the second light emitting layer to form a second electron transport layer. LiF (lithium fluoride) in a thickness of 10 Å and aluminum in a thickness of 800 Å were deposited on the electron transport layer to form a cathode, thereby completing the manufacture of an organic light emitting device.

NPB
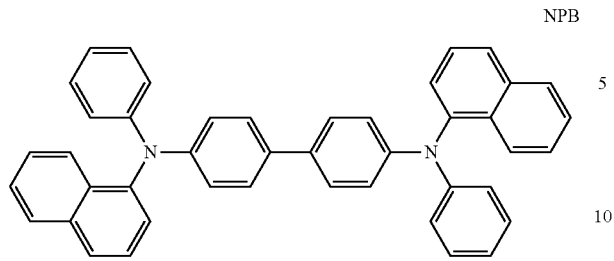
EB-B
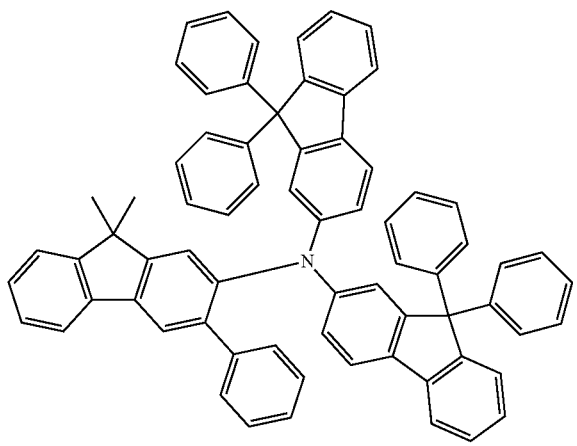
YGH-A
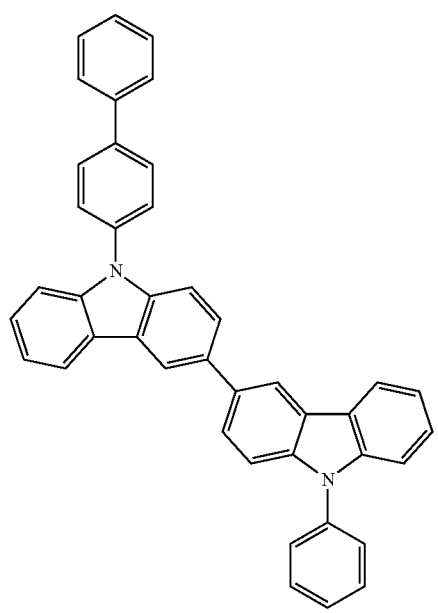
YGH-B
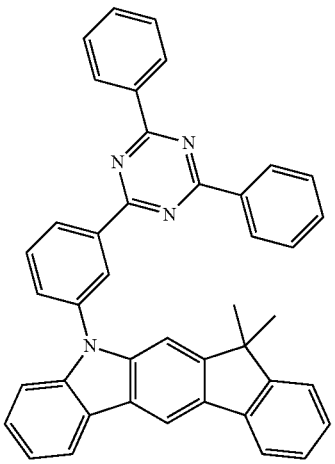
YGD
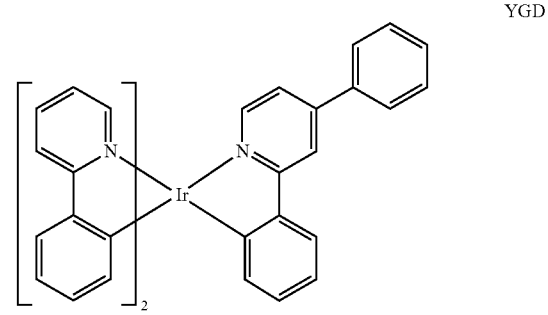
ET-B
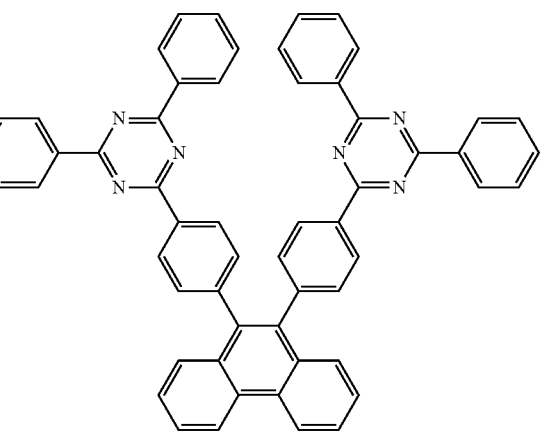
NCG
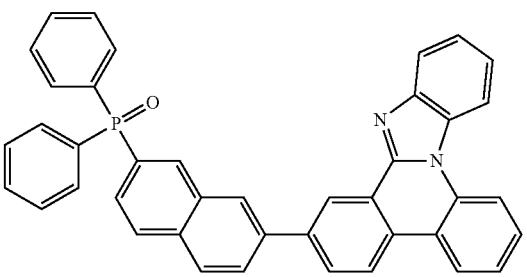

BH-B

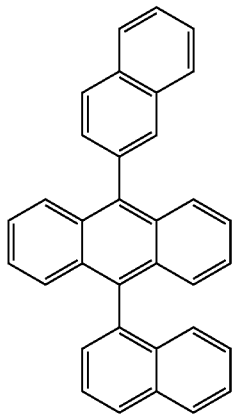

BD-B

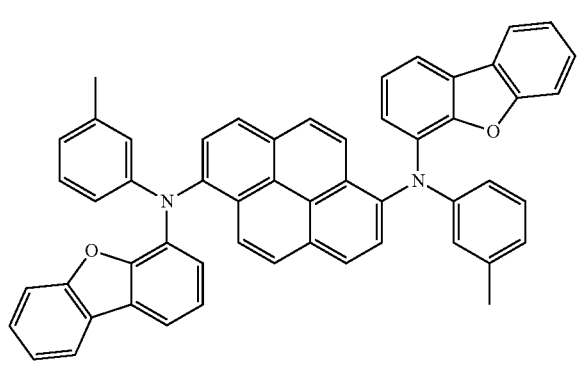

Experimental Examples 2-2 to 2-6

The organic light emitting devices were manufactured in the same manner as in Experimental Example 2-1, except that the compounds shown in Table 2 below were used instead of Compound 1 in Experimental Example 2-1.

Comparative Experimental Examples 2-1 to 2-3

The organic light emitting devices was manufactured in the same manner as in Experimental Example 2-1, except that the compounds shown in Table 2 below were used instead of Compound 1 in Experimental Example 2-1. The compound HAT-CN, the compound A, and the compound B which are the compounds shown in Table 2 below are the same as the compounds shown in Table 1 above.

The driving voltages and efficiencies of the organic light emitting devices manufactured in Experimental Examples 2-1 to 2-6 and Comparative Experimental Examples 2-1 to 2-3 are shown in Table 2 below. At this time, the driving voltage and efficiency were measured by applying a current density of 10 mA/cm$^2$.

TABLE 2

| | P-type charge generating layer Doping material | Voltage (V) | Efficiency (cd/A) |
|---|---|---|---|
| Experimental Example 2-1 | Compound 1 | 8.02 | 65.42 |
| Experimental Example 2-2 | Compound 2 | 8.05 | 66.01 |
| Experimental Example 2-3 | Compound 3 | 8.02 | 65.38 |
| Experimental Example 2-4 | Compound 4 | 7.99 | 65.98 |
| Experimental Example 2-5 | Compound 5 | 8.05 | 65.23 |
| Experimental Example 2-6 | Compound 6 | 8.01 | 65.77 |
| Comparative Experimental Example 2-1 | HAT-CN | 9.10 | 59.41 |
| Comparative Experimental Example 2-2 | Compound A | 10.30 | 48.23 |
| Comparative Experimental Example 2-3 | Compound B | 13.12 | 32.15 |

EXPLANATION OF SYMBOLS

| | | | |
|---|---|---|---|
| 1: | substrate | 2: | anode |
| 3: | light emitting layer | 4: | cathode |
| 5: | hole injection layer | 6: | hole transport layer |
| 7: | light emitting layer | 8: | electron transport layer |
| 9: | electron blocking layer | 10: | electron injection layer |
| 11: | first hole transport layer | 12: | first light emitting layer |
| 13: | first electron transport layer | 14: | N-type charge generating layer |
| 15: | P-type charge generating layer | 16: | second hole transport layer |
| 17: | second light emitting layer | 18: | second electron transport layer |

The invention claimed is:
1. A compound of Chemical Formula 1:

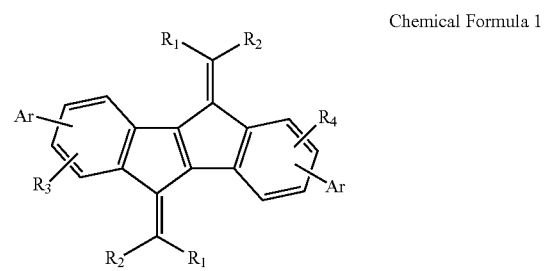

Chemical Formula 1 wherein, in Chemical Formula 1;

$R_1$ and $R_2$ are each independently hydrogen, a substituted or unsubstituted $C_{1-60}$ alkyl, a substituted or unsubstituted $C_{1-60}$ alkoxy, a substituted or unsubstituted $C_{1-60}$ haloalkyl, a substituted or unsubstituted $C_{1-60}$ haloalkoxy, halogen, cyano, tri($C_{1-60}$ alkyl)silyl, a substituted or unsubstituted $C_{6-60}$ aryl, or a substituted or unsubstituted $C_{2-60}$ heteroaryl containing at least one of O, N, Si and S;

$R_3$ and $R_4$ are each independently hydrogen, deuterium, a substituted or unsubstituted $C_{1-60}$ alkyl, a substituted or unsubstituted $C_{1-60}$ alkoxy, a substituted or unsubstituted $C_{1-60}$ haloalkyl, a substituted or unsubstituted $C_{1-60}$ haloalkoxy, halogen, cyano, tri($C_{1-60}$ or a substituted or unsubstituted $C_{2-60}$ heteroaryl containing at least one of O, N, Si and S; and Ar is $C_{6-60}$ aryl, or $C_{2-60}$ heteroaryl containing at least one of O, N, Si and S, wherein the $C_{6-60}$ aryl, or $C_{2-60}$ heteroaryl is substituted with 1 to 5 substituents each selected from the group consisting of a substituted or unsubstituted $C_{1-60}$ alkyl, a substituted or unsubstituted $C_{1-60}$ alkoxy, a substituted or unsubstituted $C_{1-60}$ haloalkyl, a substituted or unsubstituted $C_{1-60}$ haloalkoxy, halogen, cyano, and tri($C_{1-60}$ alkyl)silyl.

2. The compound according to claim 1, wherein:
$R_1$ and $R_2$ are each independently cyano or 2,3,5,6-tetrafluoro-4-cyanophenyl.

3. The compound according to claim 1, wherein:
$R_3$ and $R_4$ are each independently hydrogen or deuterium.

4. The compound according to claim 1, wherein:
the compound of Chemical Formula 1 is one of the following Chemical Formulas 1-1, 1-2, 1-3, or 1-4:

Chemical Formula 1-1

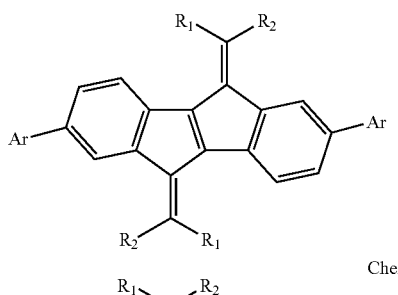

Chemical Formula 1-2

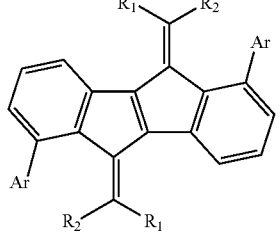

Chemical Formula 1-3

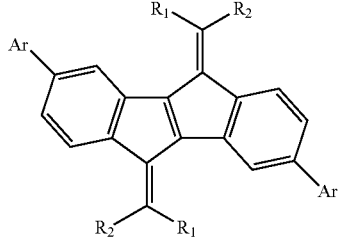

Chemical Formula 1-4

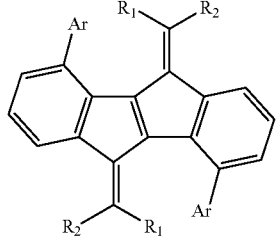

wherein, in Chemical Formulas 1-1, 1-2, 1-3 and 1-4:
$R_1$ and $R_2$ are each independently hydrogen, a substituted or unsubstituted $C_{1-60}$ alkyl, a substituted or unsubstituted $C_{1-60}$ alkoxy, a substituted or unsubstituted $C_{1-60}$ haloalkyl, a substituted or unsubstituted $C_{1-60}$ haloalkoxy, halogen, cyano, tri($C_{1-60}$ alkyl)silyl, a substituted or unsubstituted $C_{6-60}$ aryl, or a substituted or unsubstituted $C_{2-60}$ heteroaryl containing at least one of O, N, Si and S; and
Ar is $C_{6-60}$ aryl, or $C_{2-60}$ heteroaryl containing at least one of O, N, Si and S, wherein the $C_{6-60}$ aryl, or $C_{2-60}$ heteroaryl is substituted with 1 to 5 substituents each selected from the group consisting of a substituted or unsubstituted $C_{1-60}$ alkyl, a substituted or unsubstituted $C_{1-60}$ alkoxy, a substituted or unsubstituted $C_{1-60}$ haloalkyl, a substituted or unsubstituted $C_{1-60}$ haloalkoxy, halogen, cyano, and tri($C_{1-60}$ alkyl)silyl.

5. The compound according to claim 1, wherein:
Ar is phenyl, wherein said phenyl is substituted with 1 to 5 substituents each selected from the group consisting of a substituted or unsubstituted $C_{1-60}$ alkyl, a substituted or unsubstituted $C_{1-60}$ alkoxy, a substituted or unsubstituted $C_{1-60}$ haloalkyl, a substituted or unsubstituted $C_{1-60}$ haloalkoxy, halogen, cyano, and tri($C_{1-60}$ alkyl)silyl.

6. The compound according to claim 1, wherein:
Ar is phenyl, wherein said phenyl is substituted with 1 to 5 substituents each selected from the group consisting of fluoro, trifluoromethyl, trifluoromethoxy, and cyano.

7. The compound according to claim 1, wherein:
Ar is any one selected from the group consisting of the following:

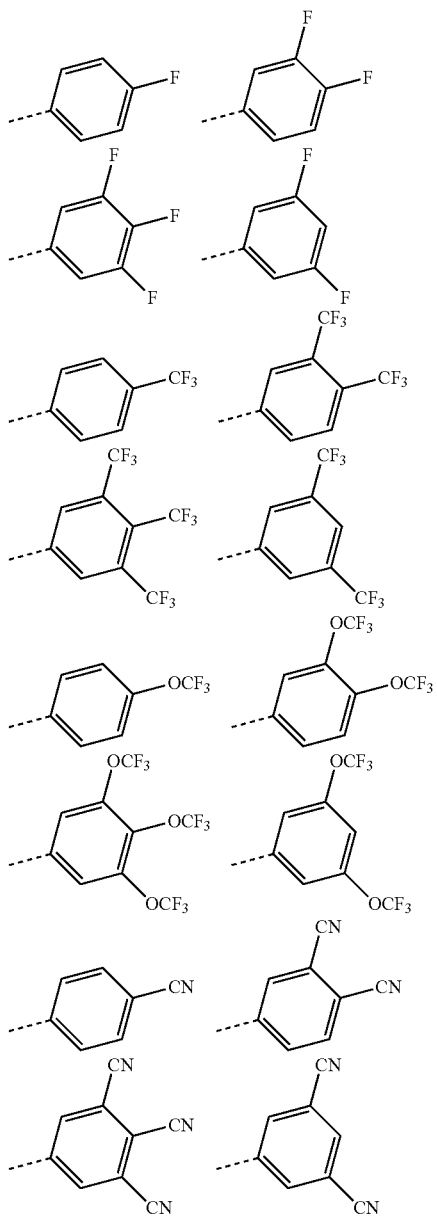

-continued
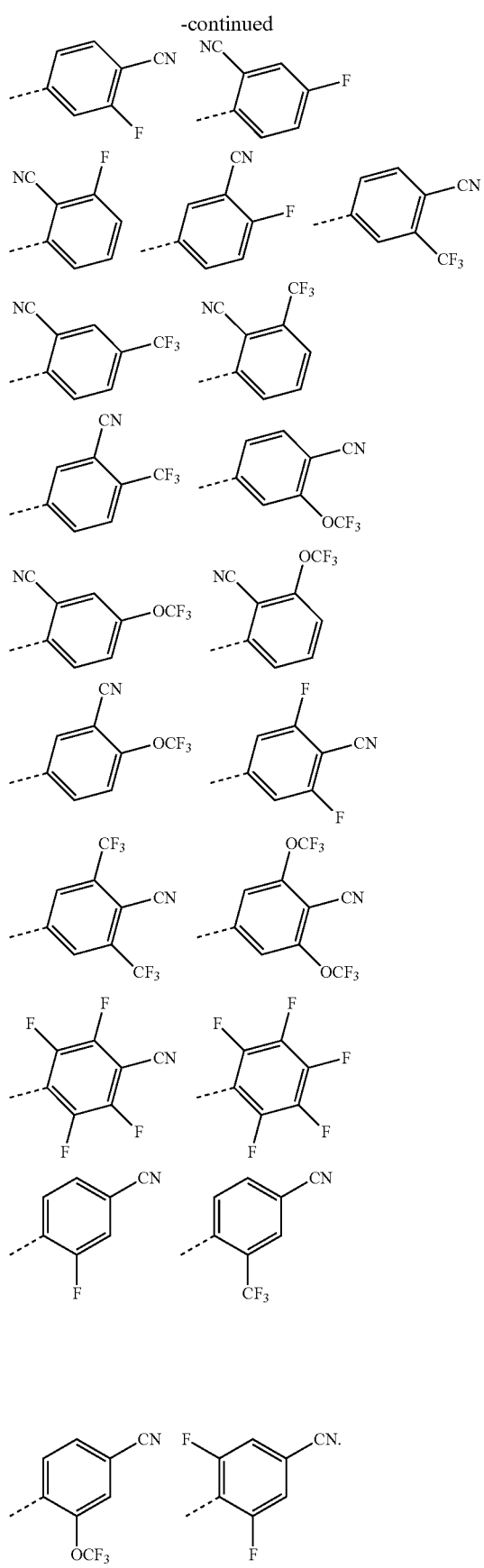
8. The compound according to claim 1, wherein:
the compound of Chemical Formula 1 is any one selected from the group consisting of the following:
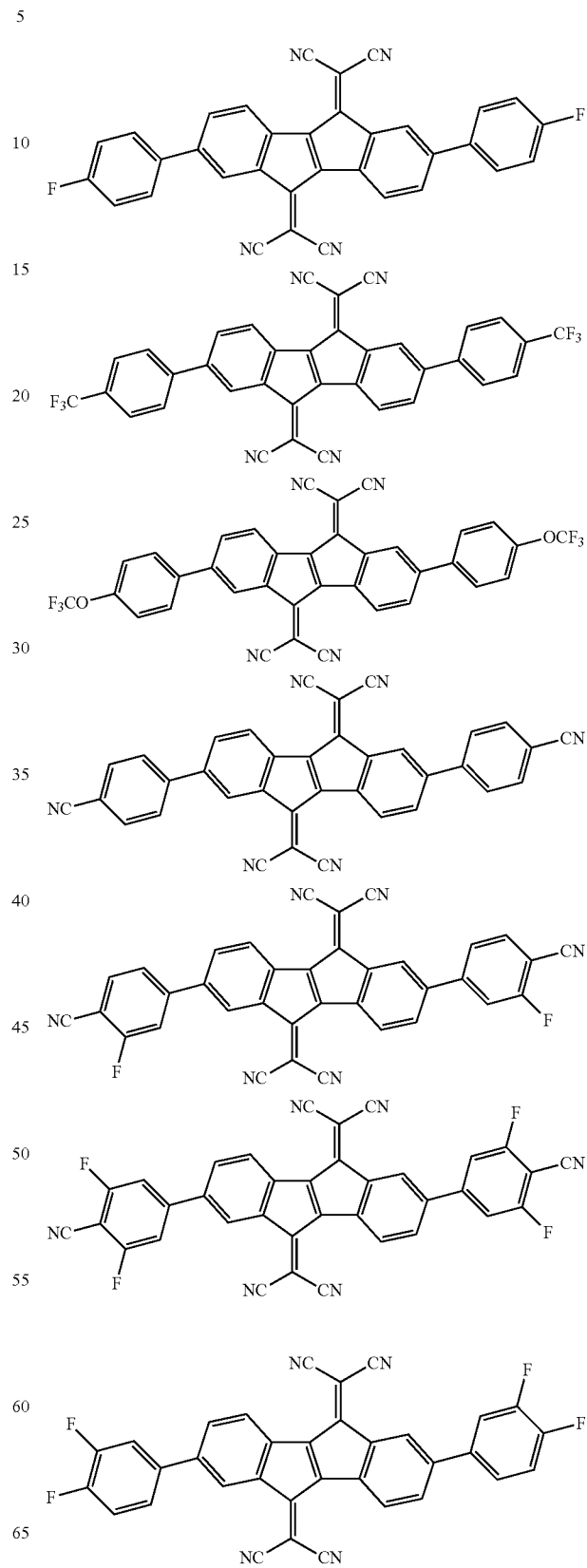

-continued
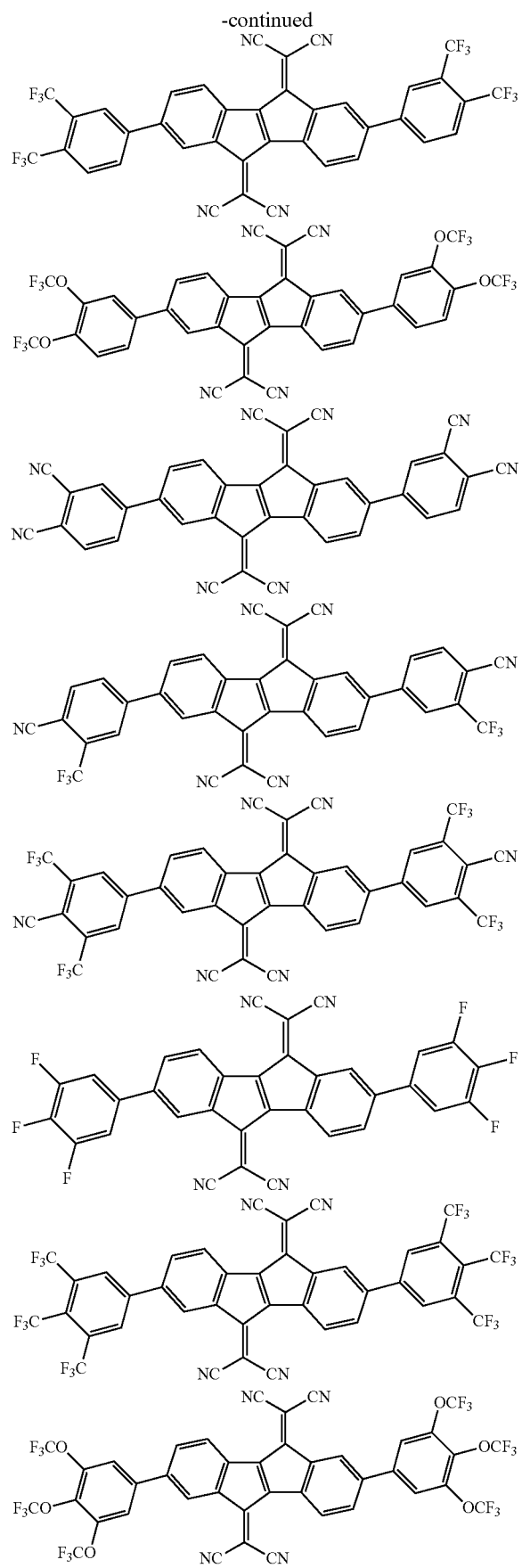
-continued
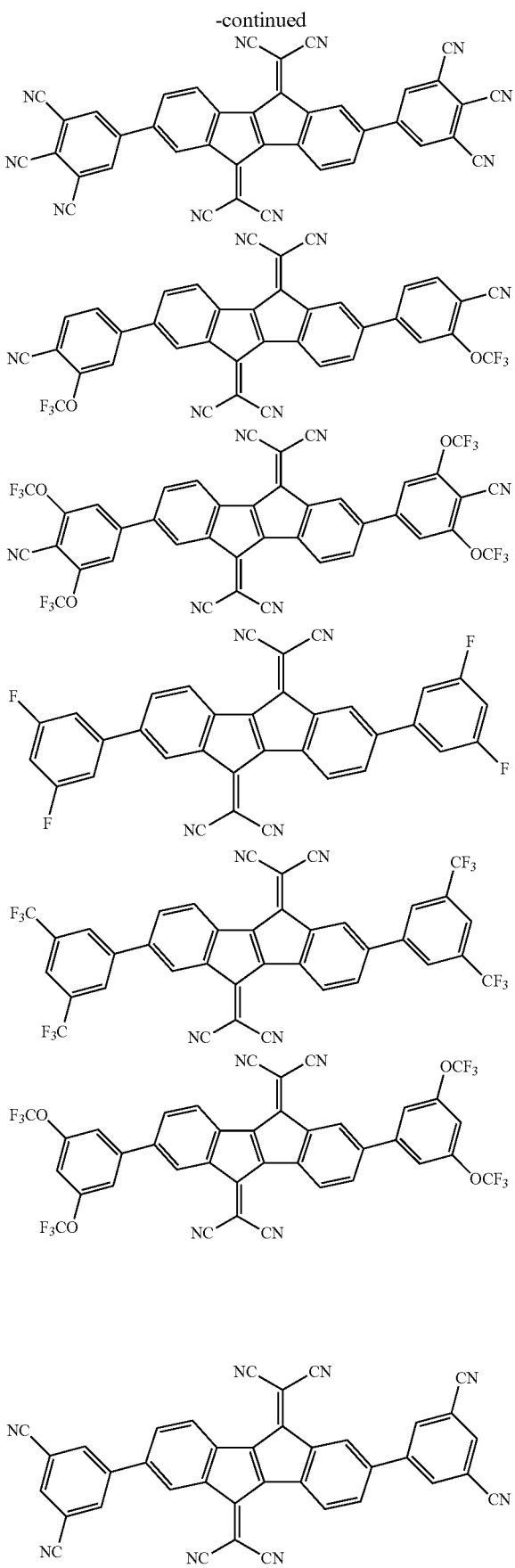

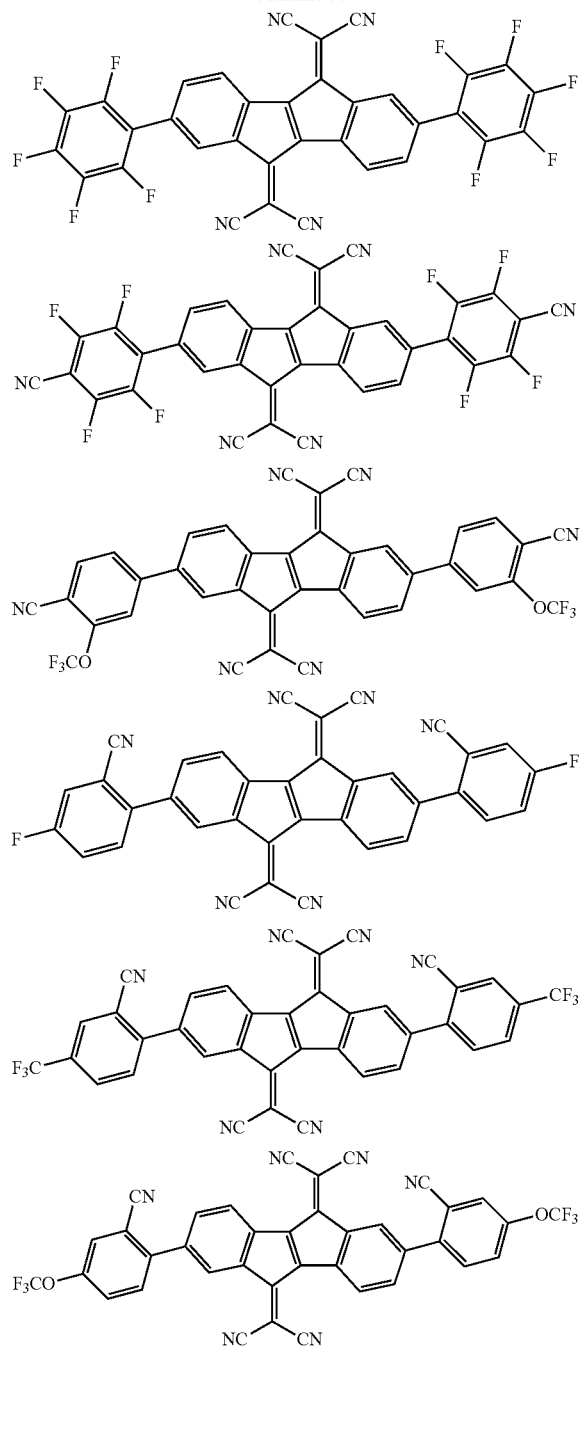
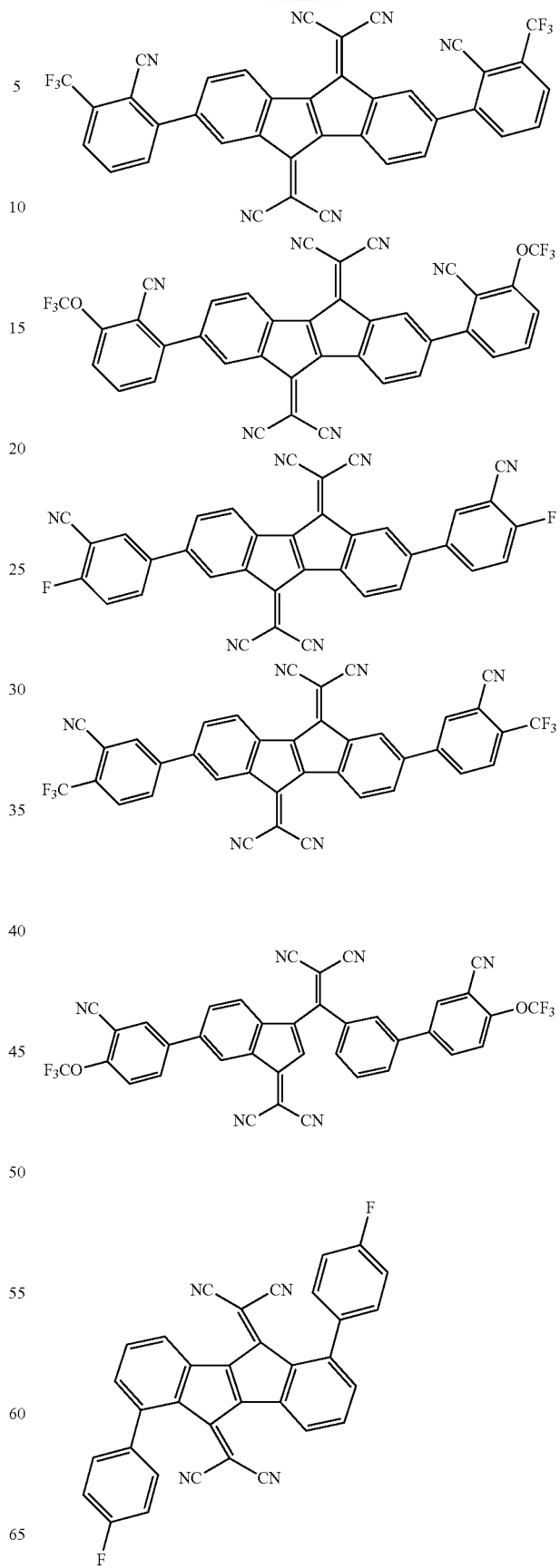

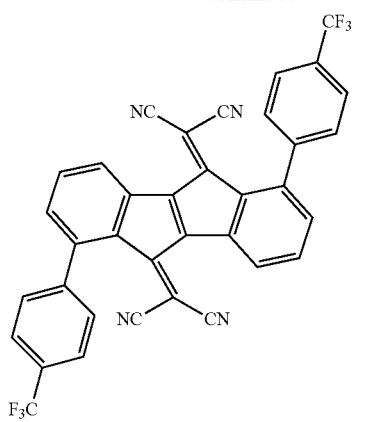
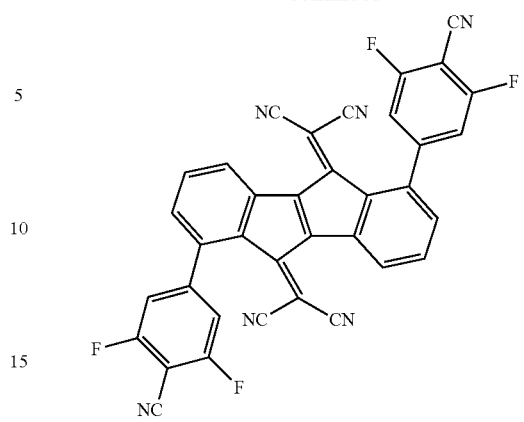
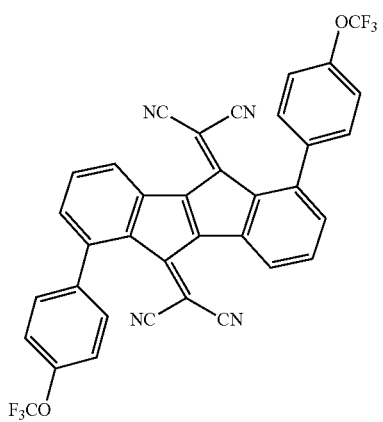
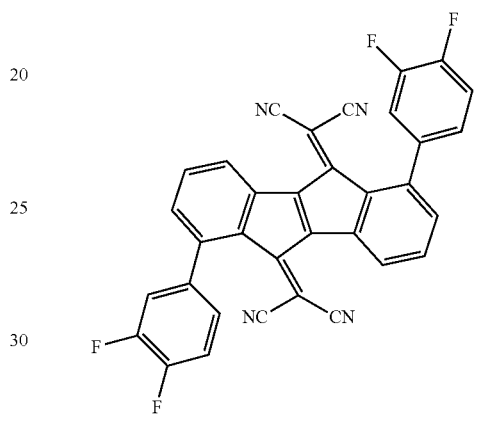
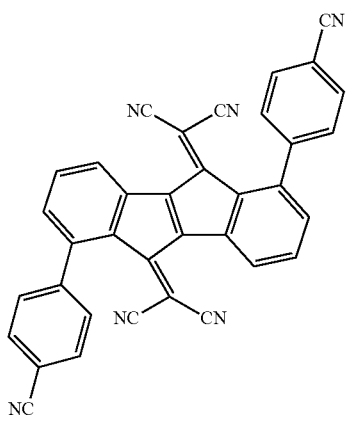
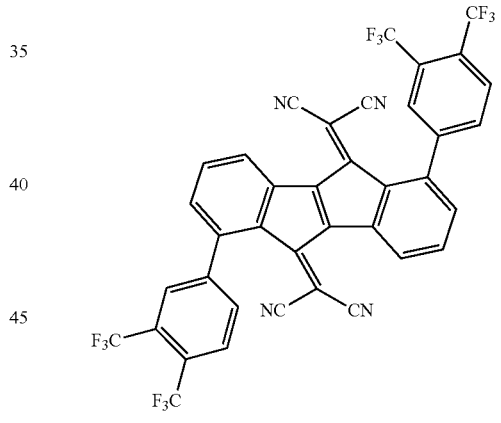
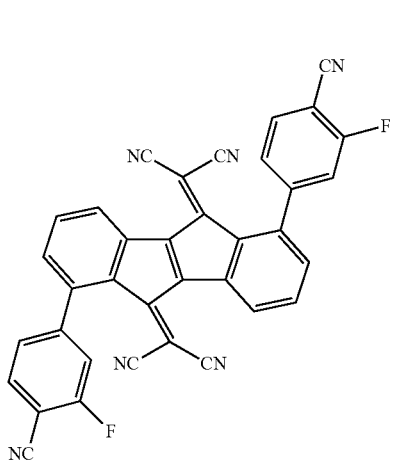
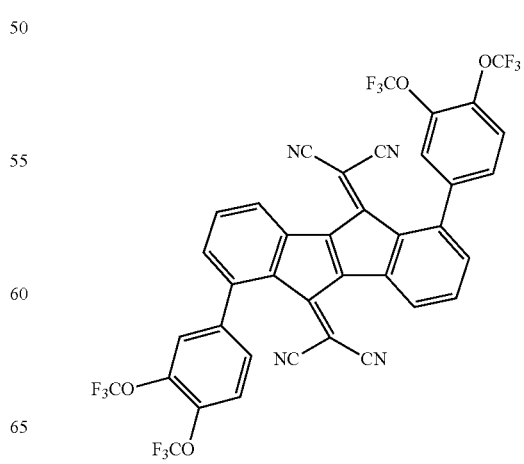

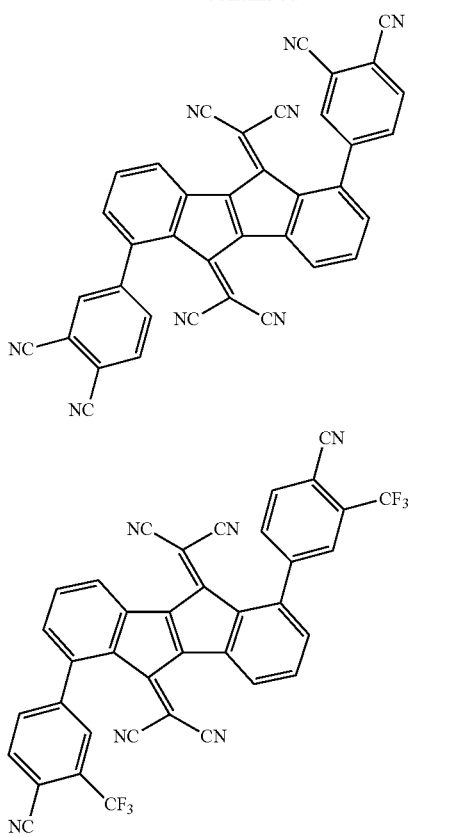
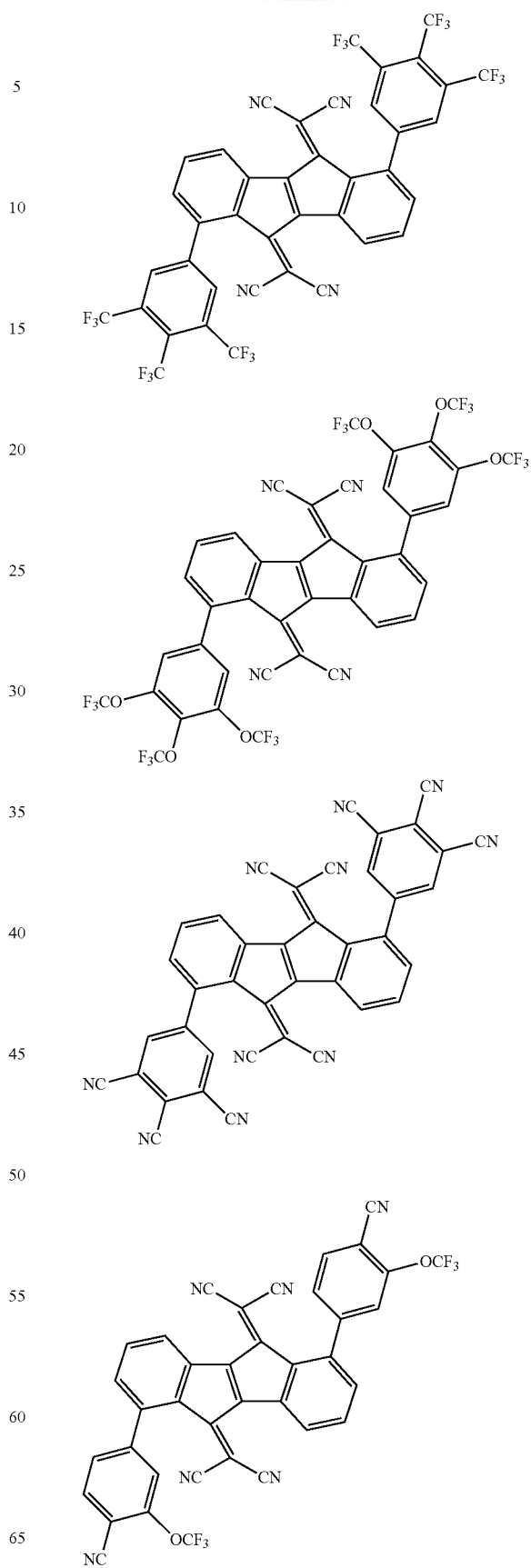

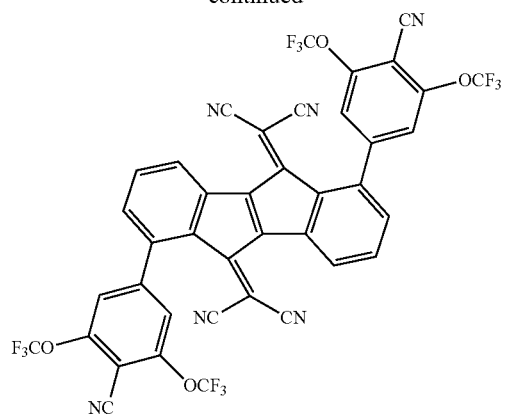
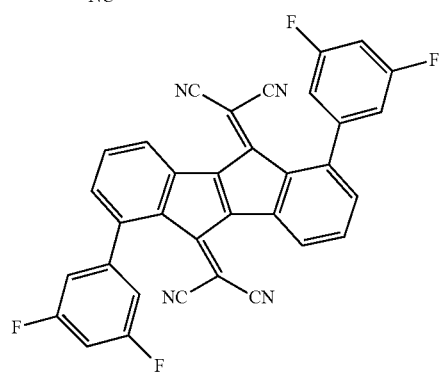
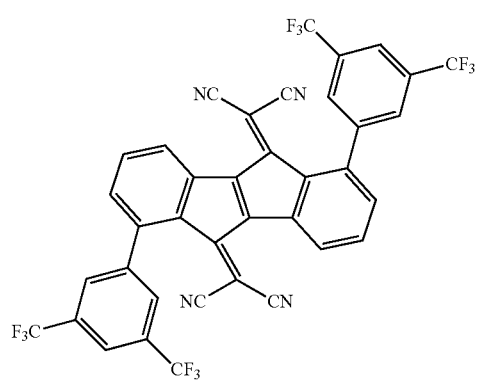
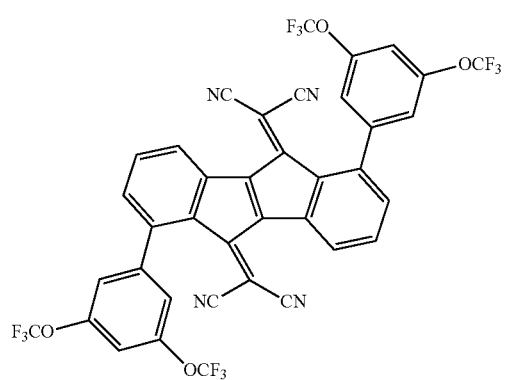
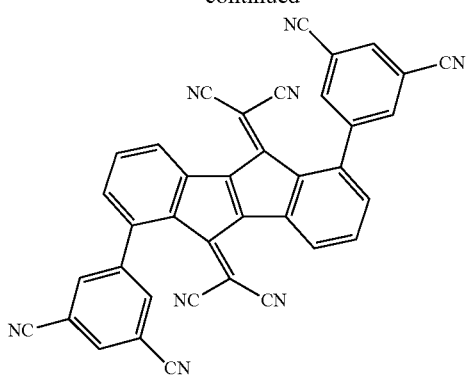
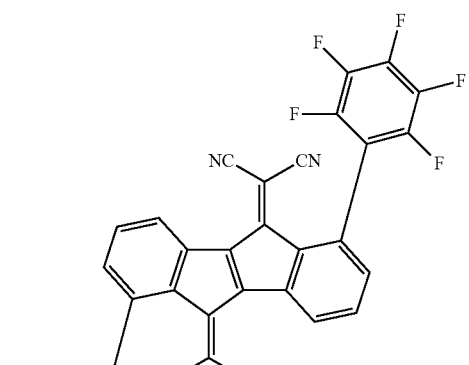
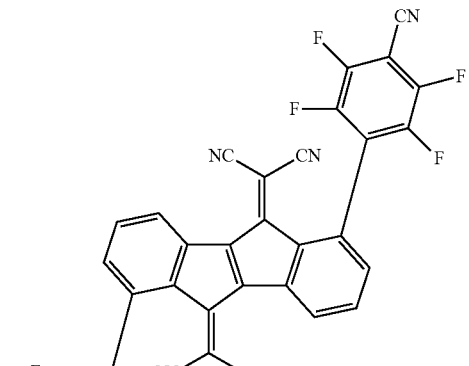

89
-continued
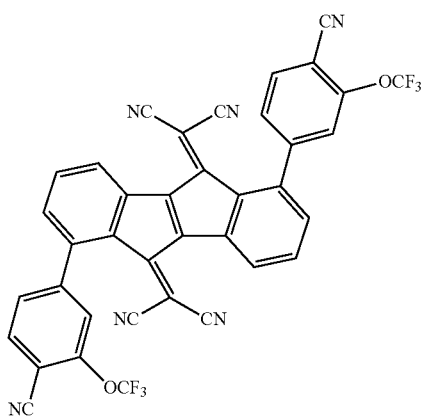
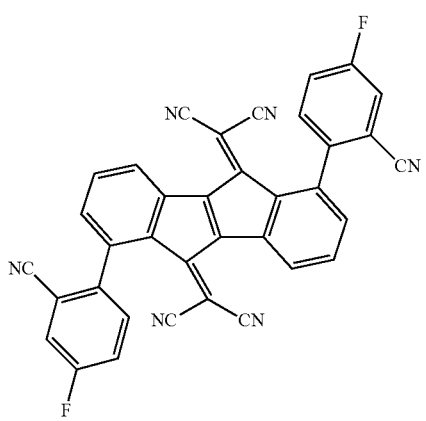
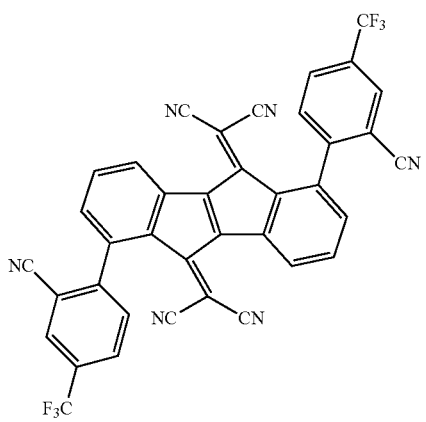
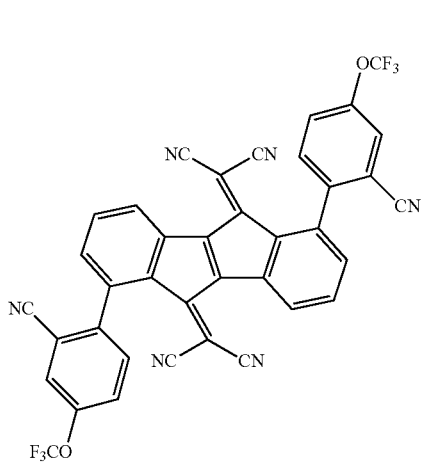
90
-continued
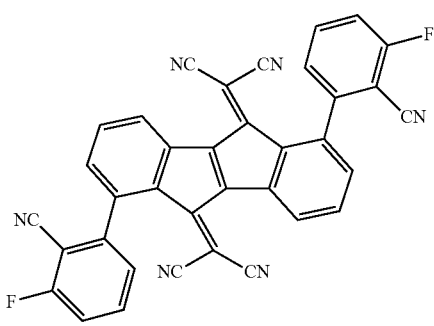
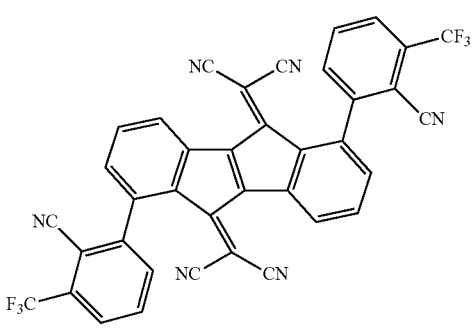

-continued
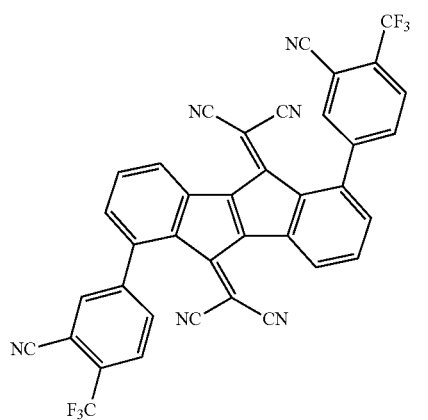
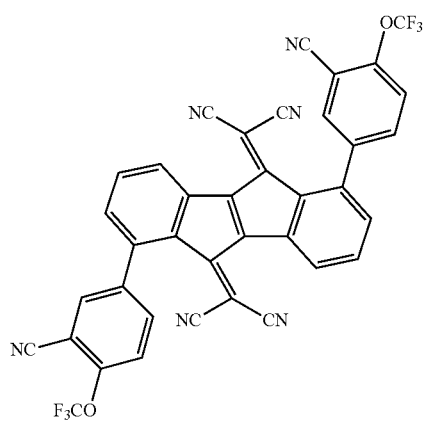
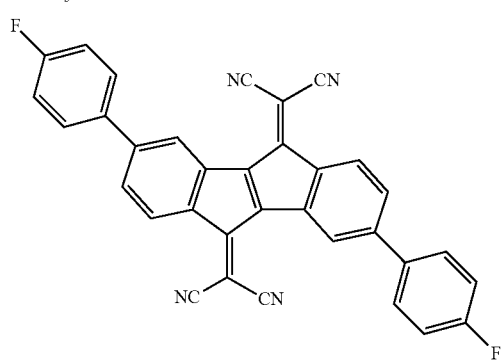
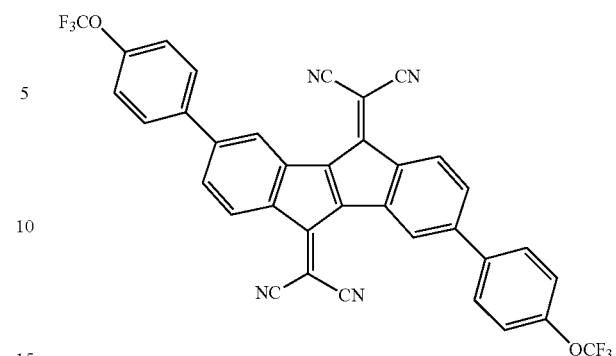
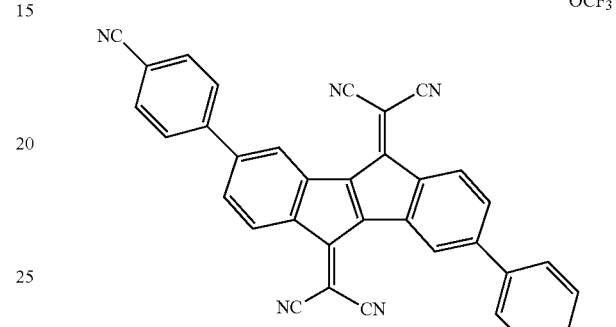
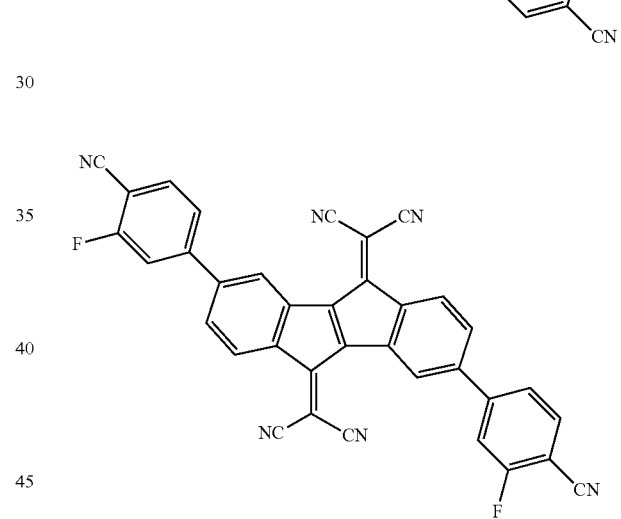
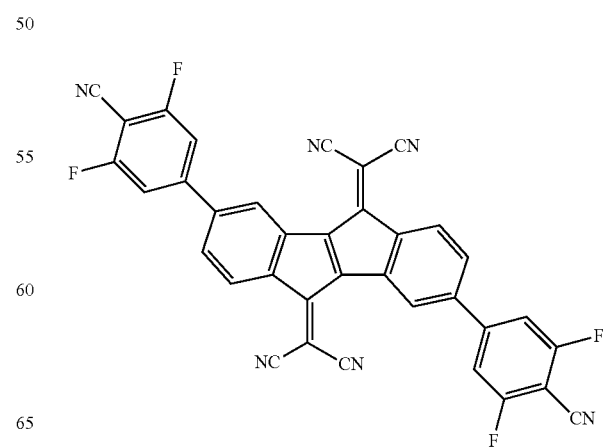

93
-continued
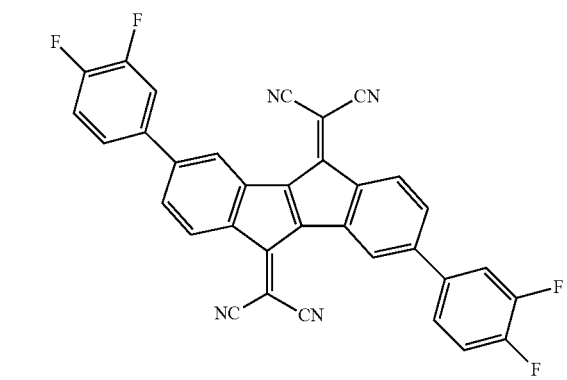
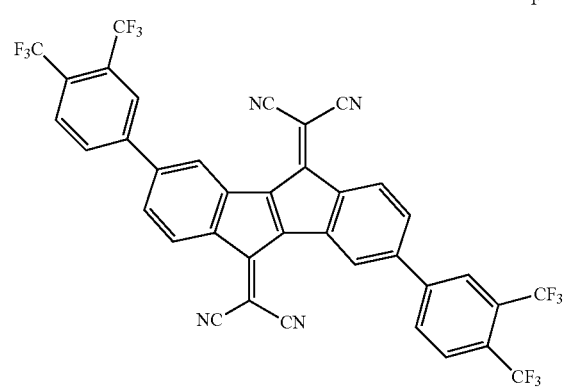
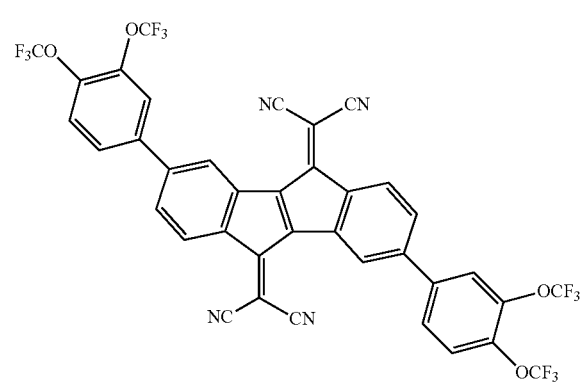
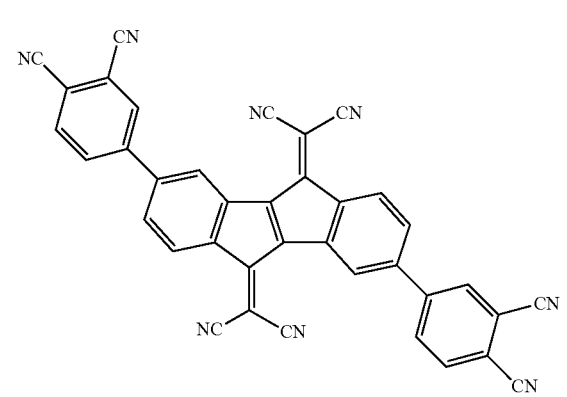
94
-continued
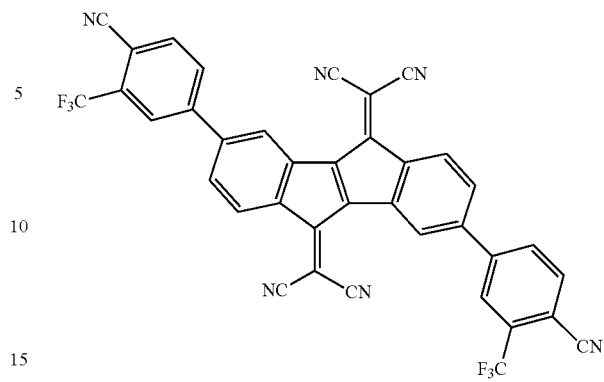
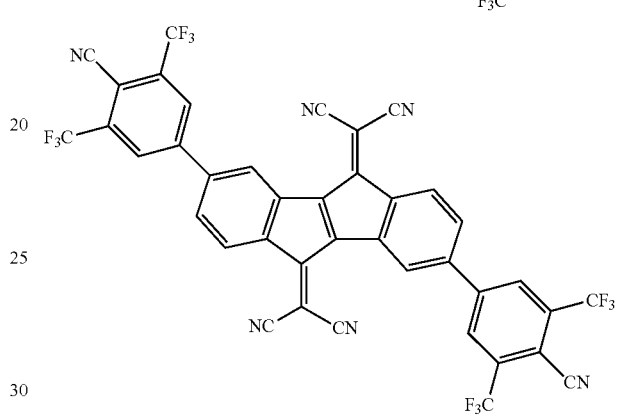
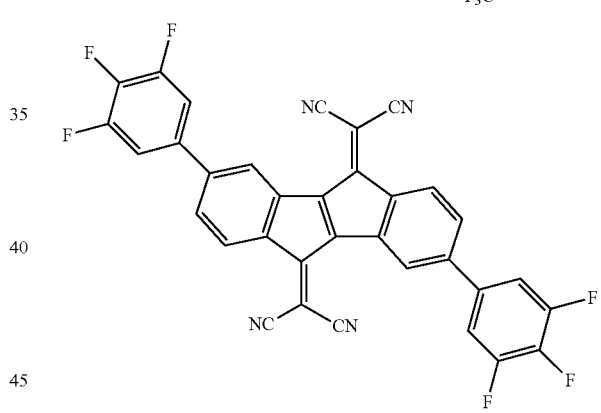
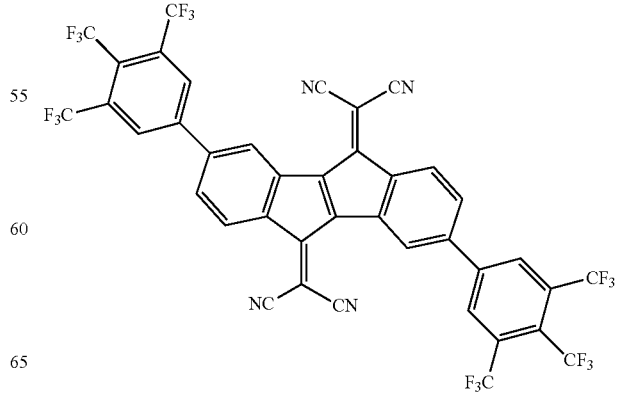

95
-continued
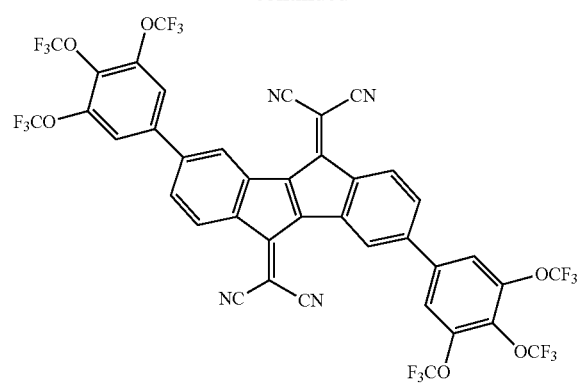
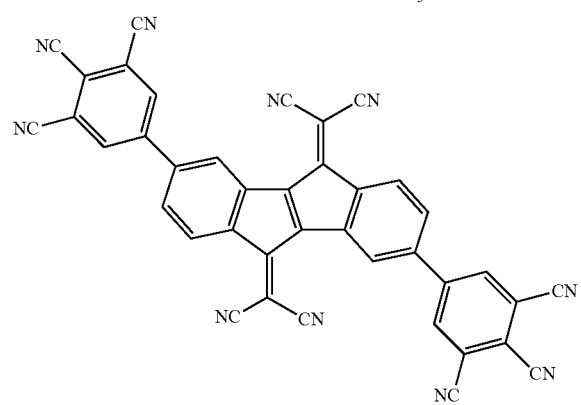
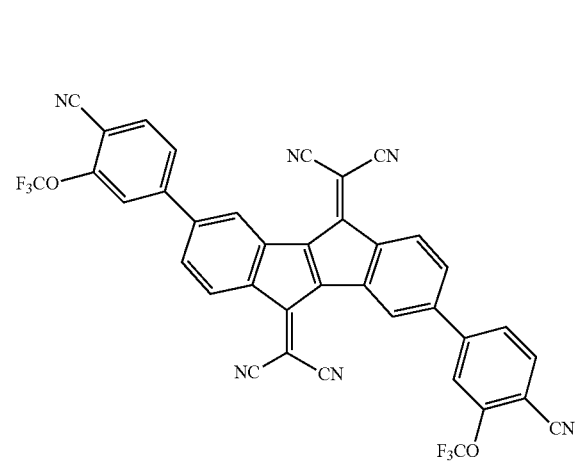
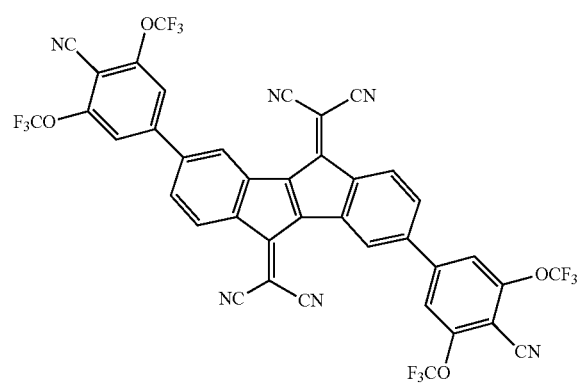
96
-continued
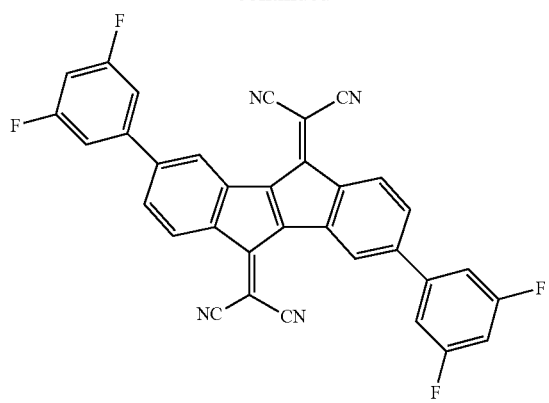
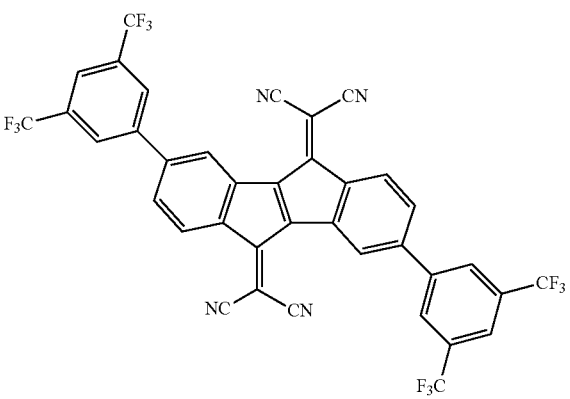
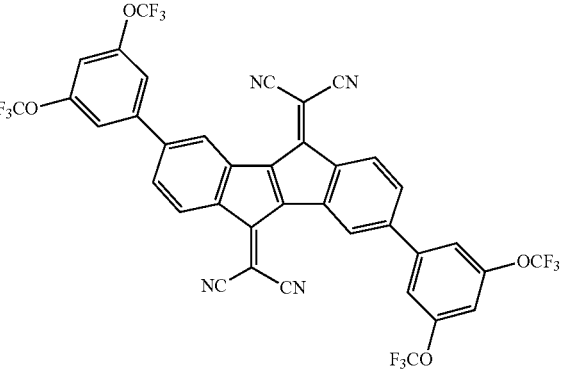
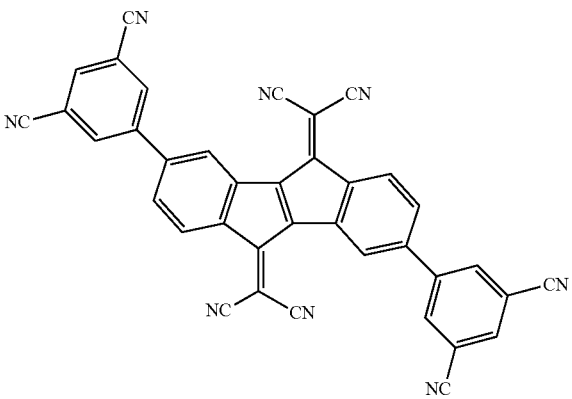

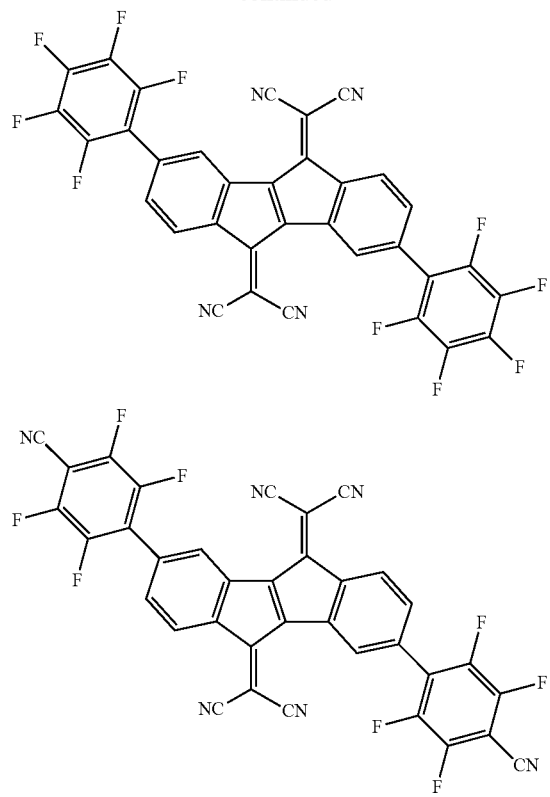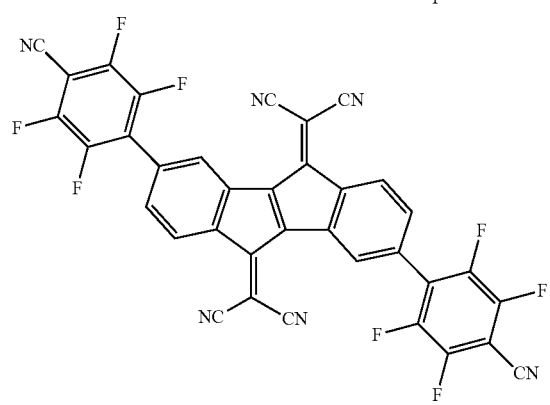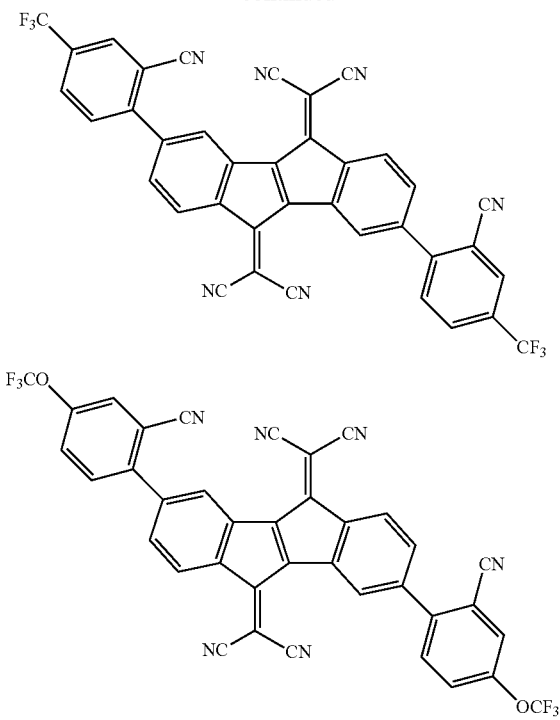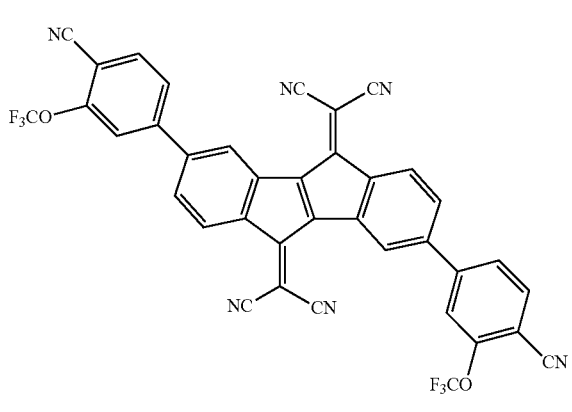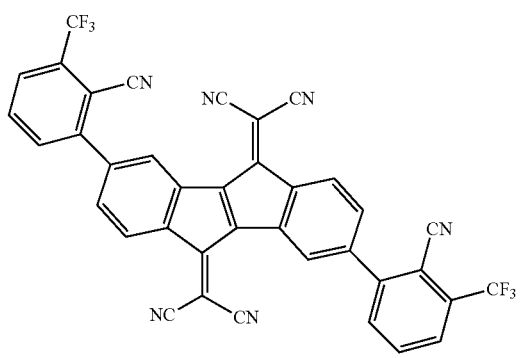

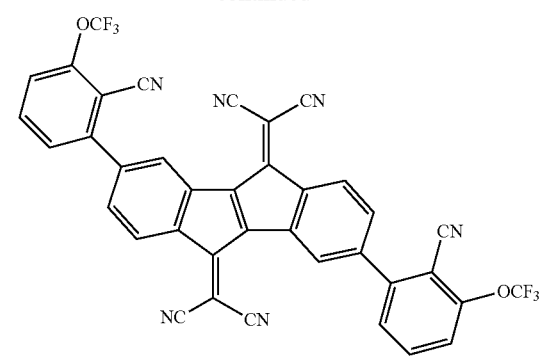
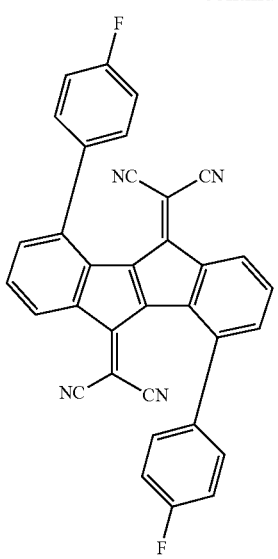
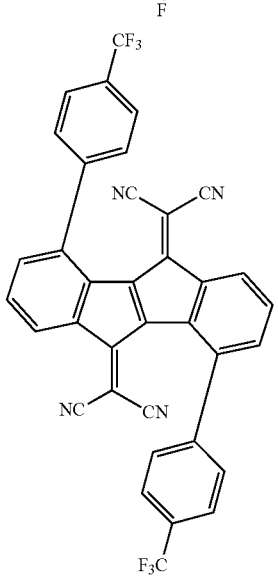
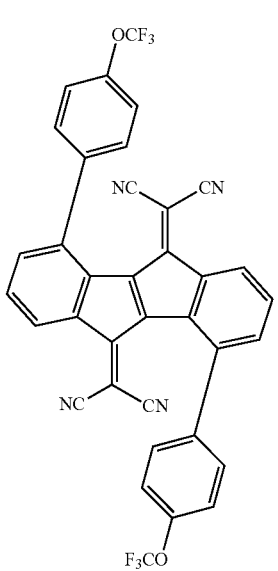

101
-continued
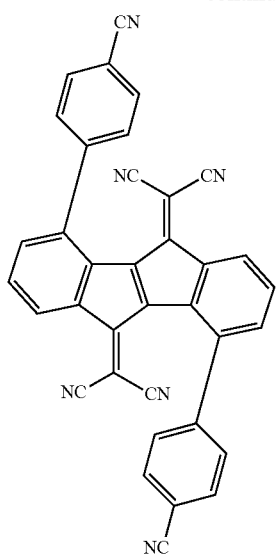
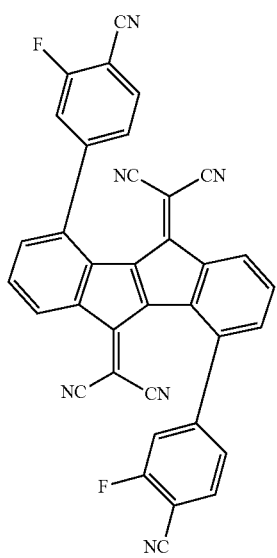
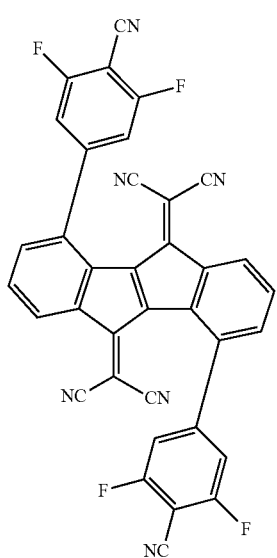
102
-continued
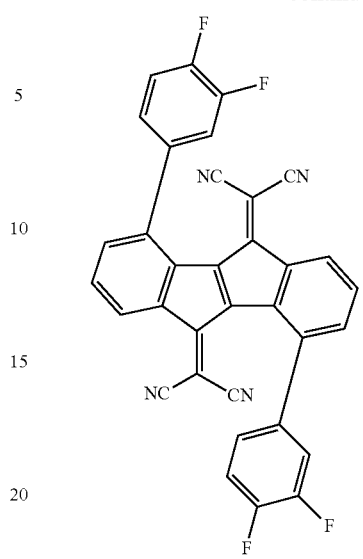
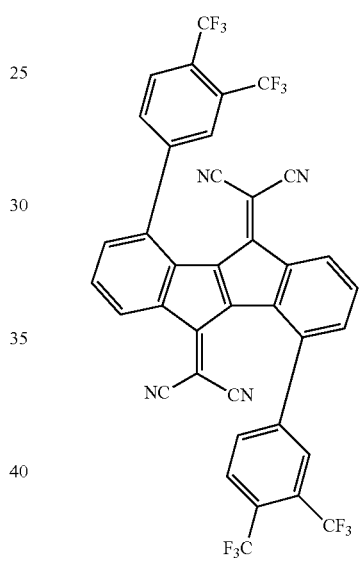
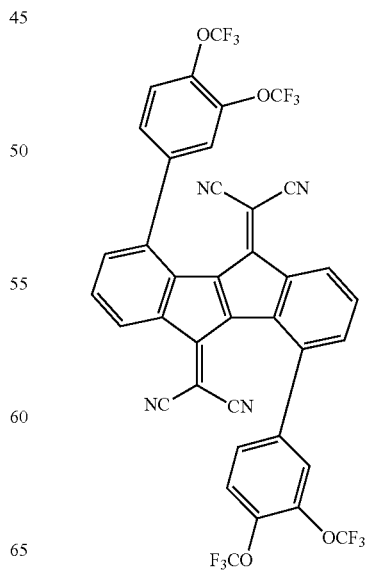

103
-continued
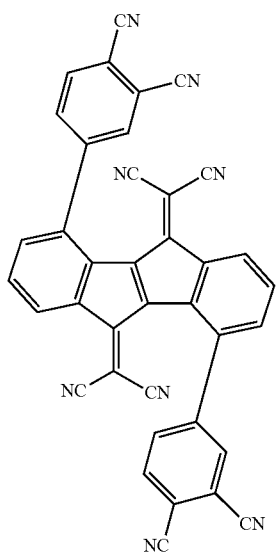
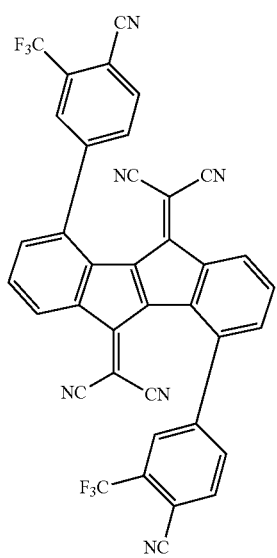
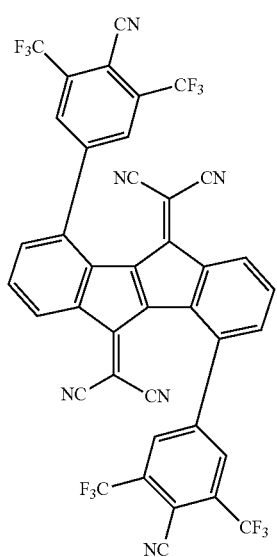
104
-continued
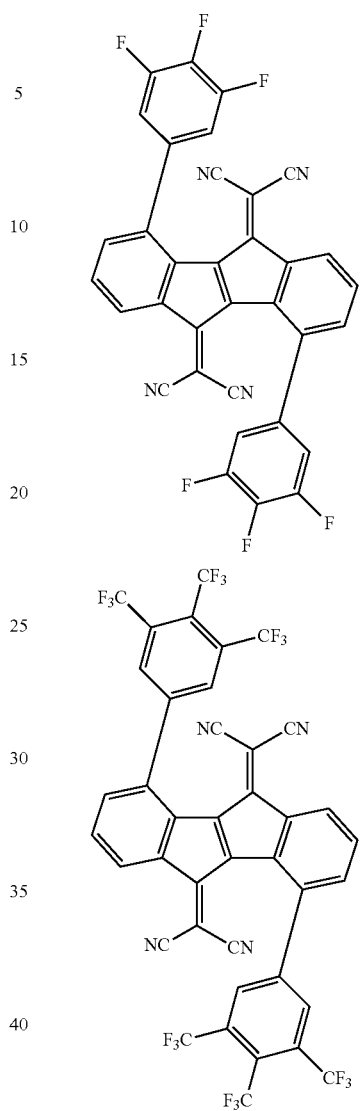
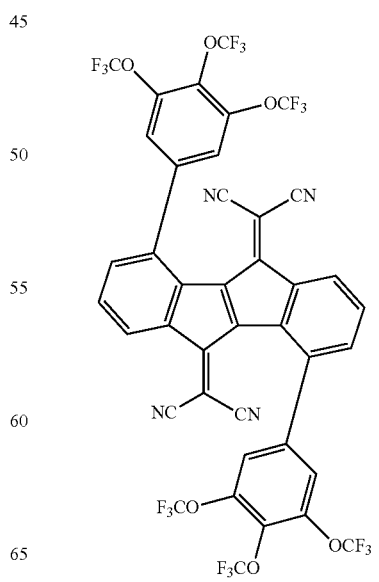

105
-continued
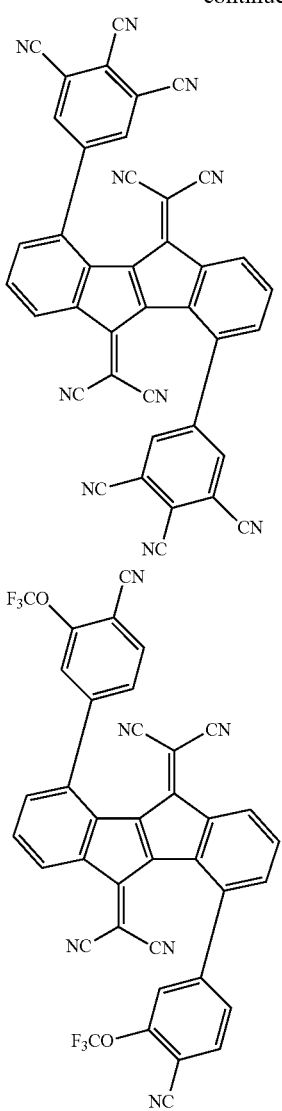
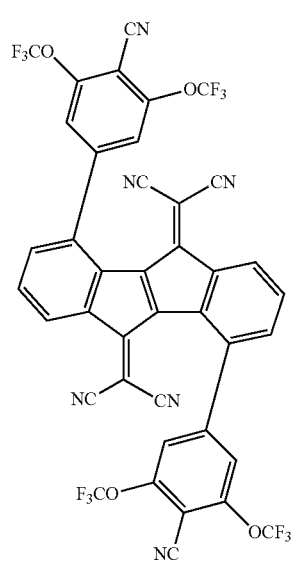
106
-continued
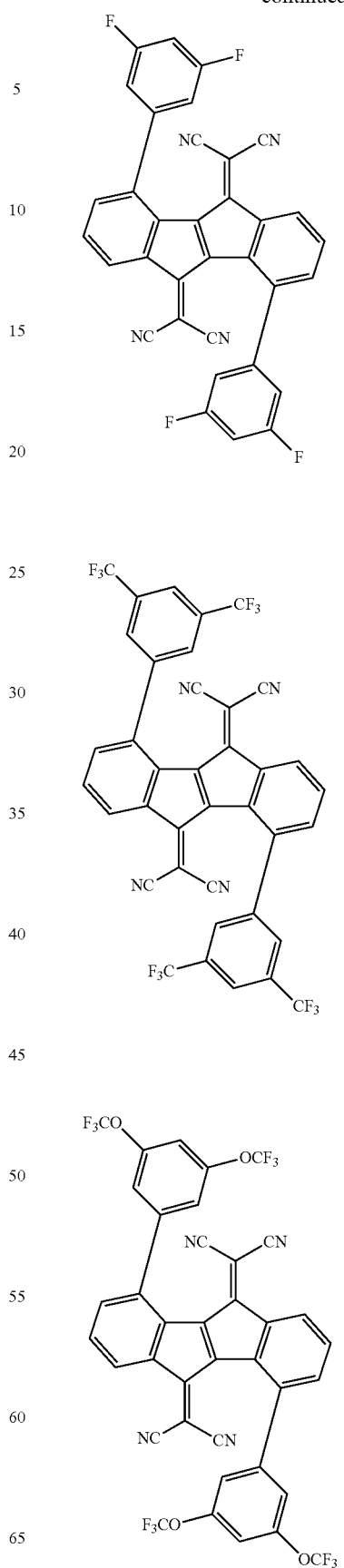

107
-continued
108
-continued
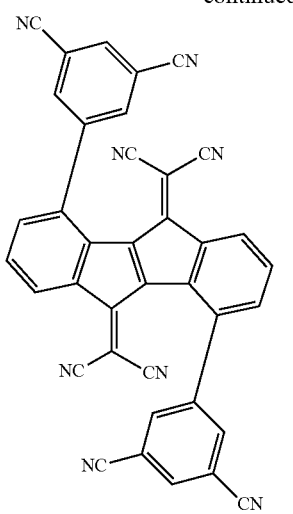
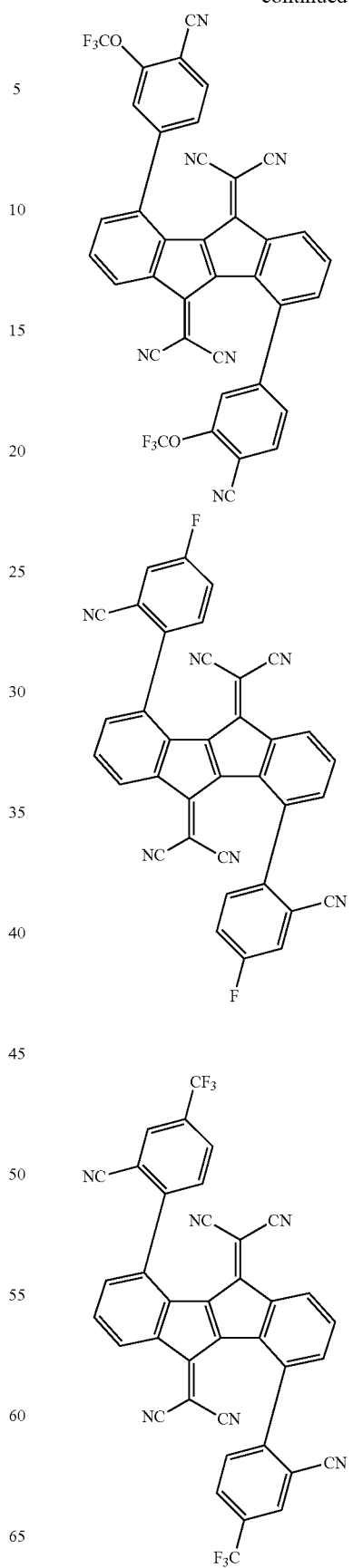

109
-continued
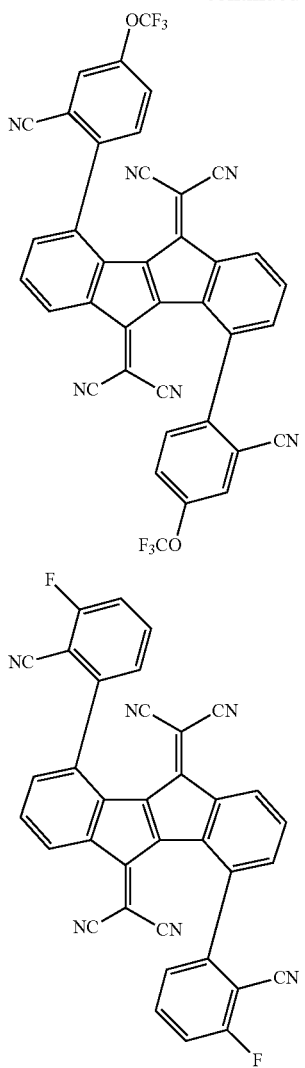
110
-continued
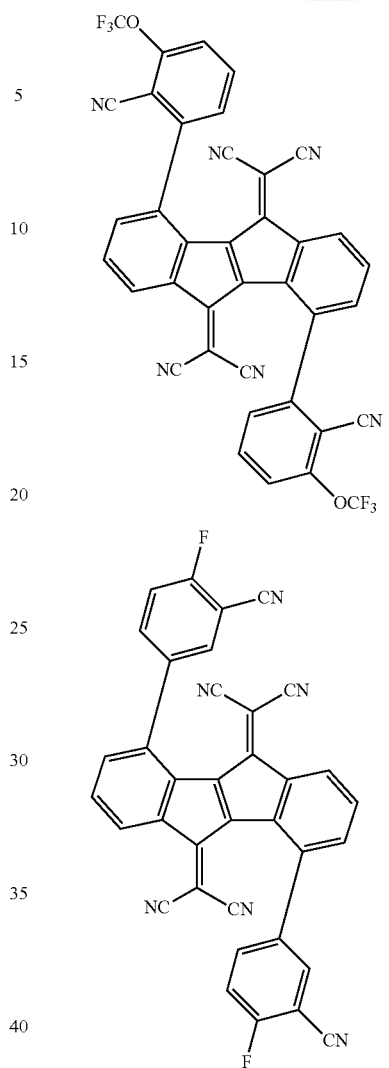
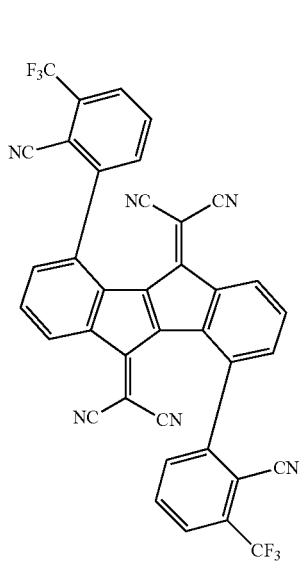
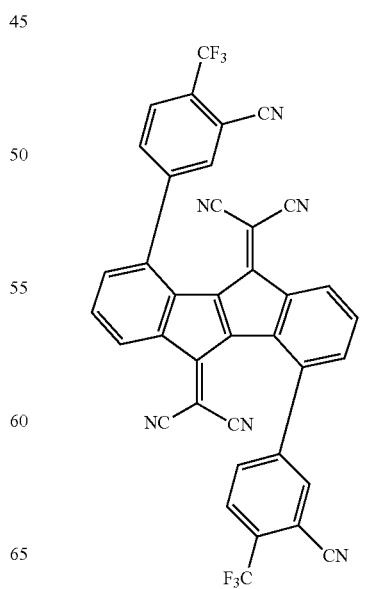

111
-continued
112
-continued
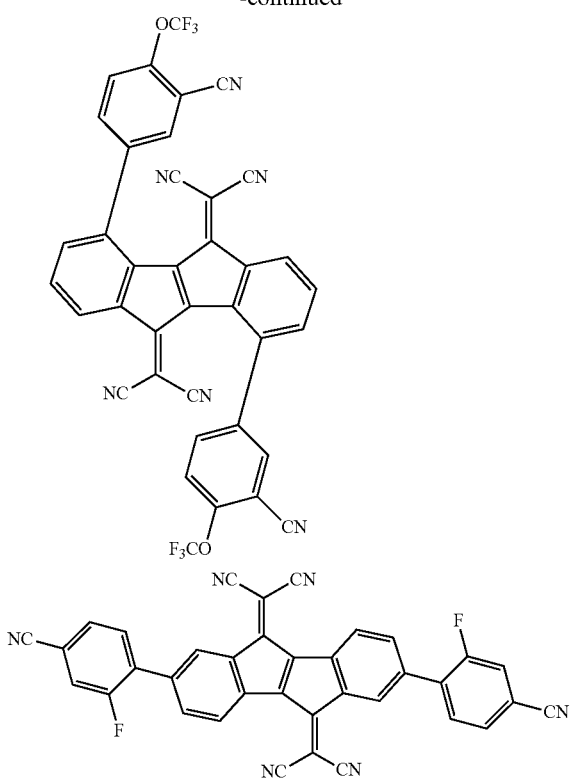
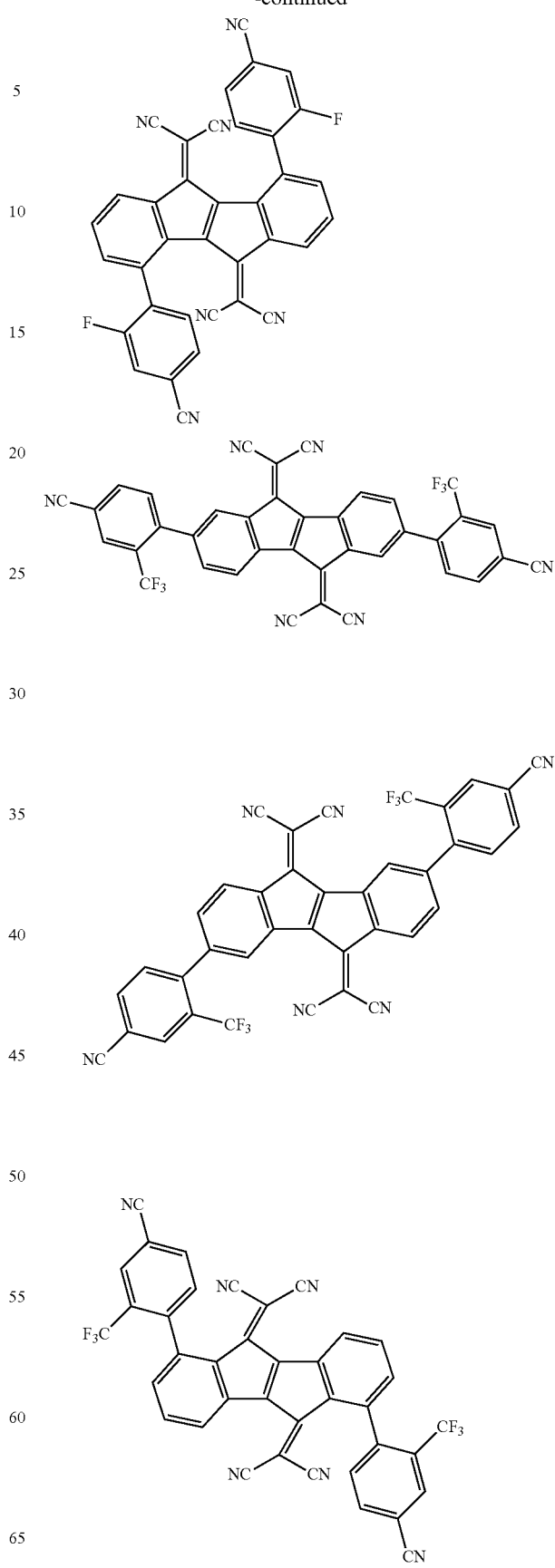

113
-continued
114
-continued
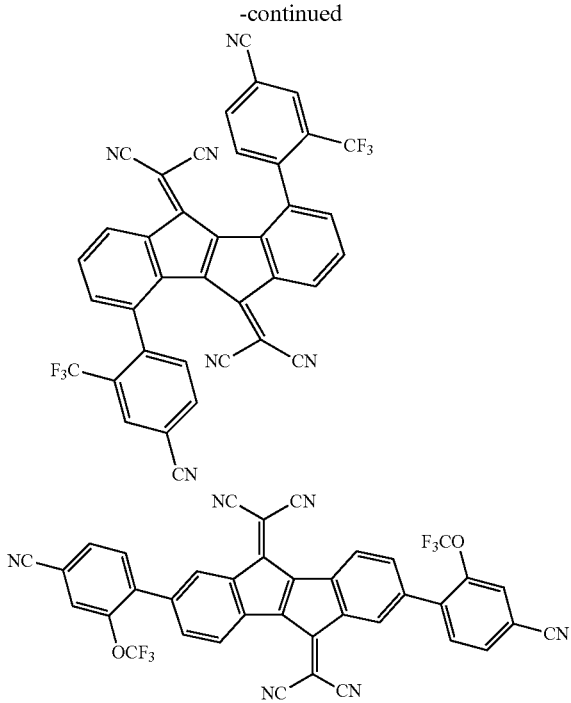
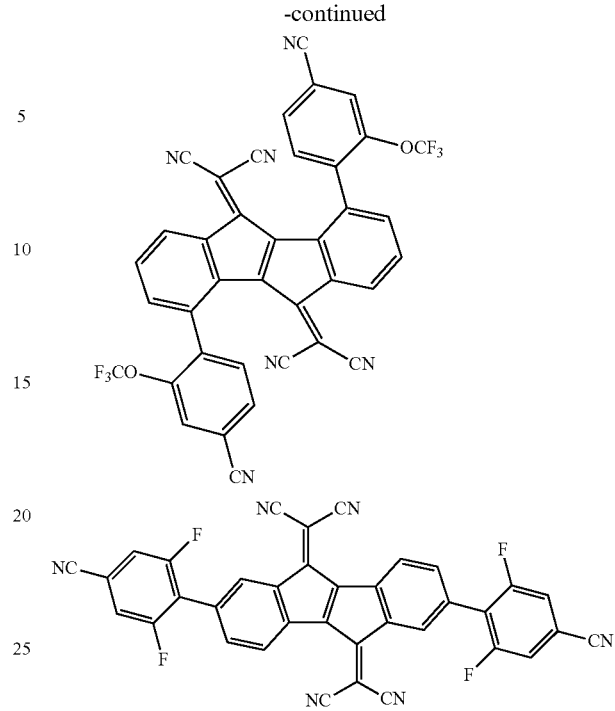
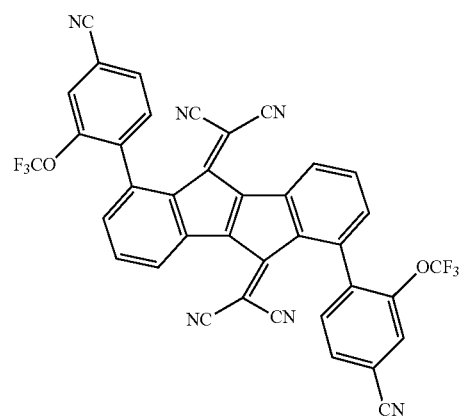
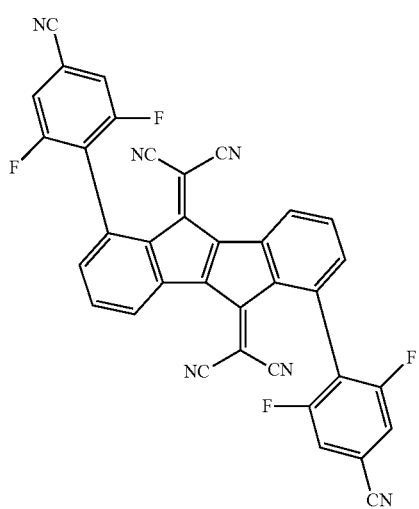

-continued

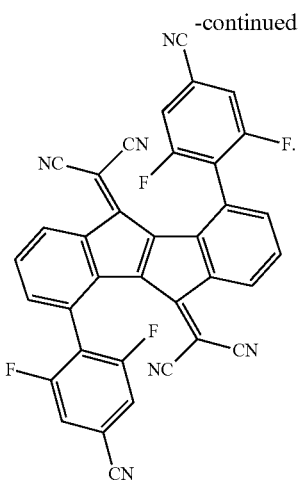

9. An organic light emitting device comprising:
a first electrode;
a second electrode that is disposed opposite to the first electrode; and
one or more organic material layers that are disposed between the first electrode and the second electrode, wherein one or more layers of the organic material layers include the compound of claim 1.

10. The organic light emitting device according to claim 9, wherein:
the organic material layer includes a hole injection layer, wherein the hole injection layer is formed of the compound alone or is formed by doping the compound.

11. The organic light emitting device according to claim 9, wherein:
the organic material layer includes a doped hole transport layer, wherein the doped hole transport layer is formed by doping the hole transport material with the compound.

12. The organic light emitting device according to claim 9, wherein:
a first stack emitting light of a first color, a second stack emitting light of a second color, and a charge generating layer that uniformly controls charges between the first stack and the second stack are formed between the first electrode and the second electrode,
wherein the charge generating layer includes a N-type charge generating layer disposed adjacent to the first stack and a P-type charge generating layer disposed adjacent to the second stack,
wherein the organic material layer constitutes the P-type charge generating layer, and wherein the P-type charge generating layer is formed of the compound alone or is formed by doping the compound.

13. The organic light emitting device according to claim 9, wherein:
a first stack emitting light of a first color, a second stack emitting light of a second color, and a charge generating layer that uniformly controls charges between the first stack and the second stack are formed between the first electrode and the second electrode,
wherein the charge generating layer includes a N-type charge generating layer disposed adjacent to the first stack and a P-type charge generating layer disposed adjacent to the second stack,
wherein the organic material layer constitutes the P-type charge generating layer, and wherein the P-type charge generating layer can be formed by doping the hole transport material with the compound.

14. The organic light emitting device according to claim 9, wherein:
the organic light emitting device further comprises one layer or two or more layers selected from the group consisting of a hole injection layer, a hole transport layer, a light emitting layer, an electron transport layer, an electron injection layer, an electron blocking layer, and a hole blocking layer.

* * * * *